(12) United States Patent
Gerlach et al.

(10) Patent No.: US 11,780,827 B2
(45) Date of Patent: Oct. 10, 2023

(54) SUBSTITUTED 3-PHENOXYAZETIDIN-1-YL-PYRAZINES

(71) Applicants: Boehringer Ingelheim International GmbH, Ingelheim am Rhein (DE); Arena Pharmaceuticals, Inc.

(72) Inventors: Kai Gerlach, Ingelheim am Rhein (DE); Graeme Semple, San Diego, CA (US); Yifeng Xiong, San Diego, CA (US); Barbara Bertani, Ingelheim am Rhein (DE); Marco Ferrara, Ingelheim am Rhein (DE); Giacomo Fossati, Ingelheim am Rhein (DE); Scott Hobson, Ingelheim am Rhein (DE); Uta Friederike Lessel, Ingelheim am Rhein (DE); Frank Runge, Ingelheim am Rhein (DE); Ursula Mueller-Vieira, Ingelheim am Rhein (DE); Julian Wippich, Ingelheim am Rhein (DE)

(73) Assignees: Boehringer Ingelheim International GmbH, Ingelheim am Rhein (DE); Arena Pharmaceuticals, Inc., San Diego, CA (US)

( * ) Notice: Subject to any disclaimer, the term of this patent is extended or adjusted under 35 U.S.C. 154(b) by 142 days.

(21) Appl. No.: 17/215,759

(22) Filed: Mar. 29, 2021

(65) Prior Publication Data

US 2022/0356172 A1    Nov. 10, 2022

Related U.S. Application Data

(60) Provisional application No. 63/001,640, filed on Mar. 30, 2020.

(51) Int. Cl.
*C07D 403/14* (2006.01)
(52) U.S. Cl.
CPC ................. *C07D 403/14* (2013.01)
(58) Field of Classification Search
CPC .................................................. C07D 403/14
See application file for complete search history.

(56) References Cited

FOREIGN PATENT DOCUMENTS

EP           2 253 618 A1    11/2010
WO     WO 2016/176571 A1    11/2016

OTHER PUBLICATIONS

International Search Report and Written Opinion dated May 19, 2021 for Application No. PCT/EP2021/058099.

*Primary Examiner* — Brian E McDowell
(74) *Attorney, Agent, or Firm* — Wolf, Greenfield & Sacks, P.C.

(57) ABSTRACT

The invention relates to substituted 3-phenoxyazetidin-1-yl-pyrazines of general formula (I) which are agonists of GPR52, useful in treating central nervous system diseases and other diseases. In addition, the invention relates to the 3-phenoxyazetidin-1-yl-pyrazines of general formula (I) for use as a medicament, pharmaceutical compositions comprising the 3-phenoxyazetidin-1-yl-pyrazines of general formula (I) and processes for preparing pharmaceutical compositions as well as processes for manufacture the compounds according to the invention.

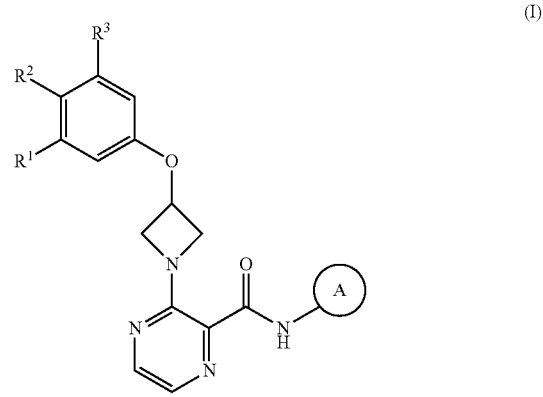

11 Claims, No Drawings

SUBSTITUTED 3-PHENOXYAZETIDIN-1-YL-PYRAZINES

CROSS REFERENCE TO RELATED APPLICATION

This application claims the benefit under 35 U.S.C. § 119(e) of the filing date of U.S. Provisional Application Ser. No. 63/001,640, filed Mar. 30, 2020, the entire contents of which is incorporated by reference herein.

FIELD OF THE INVENTION

The invention relates to substituted 3-phenoxyazetidin-1-yl-pyrazines of general formula (I) which are agonists of GPR52, useful in treating central nervous system diseases and other diseases. In addition, the invention relates to the 3-phenoxyazetidin-1-yl-pyrazines of general formula (I) for use as a medicament, pharmaceutical compositions comprising the 3-phenoxyazetidin-1-yl-pyrazines of general formula (I) and processes for preparing pharmaceutical compositions as well as processes for manufacture the compounds according to the invention.

BACKGROUND OF THE INVENTION

Human GPR52 is a G protein-coupled receptor (GPCR). The highest expression levels within the human central nervous system (CNS) are found in the striatum (WO2016/176571). Lower but significant expression levels are found in many other structures in the CNS, including the cortex. GPR52 co-localizes almost exclusively with the D2 receptor in the human and rodent striatum, and with the D1 receptor in the human and rodent cortex (WO2016/176571).

D1 receptors are generally Gs-coupled, and as such stimulate the production of the second messenger cAMP and the activity of PKA. In contrast, D2 receptors are generally Gi-coupled, and as such negatively regulate the production of cAMP and result in a decrease in PKA activity.

Since GPR52 co-localizes with the D1 receptor in the cortex and because both GPR52 and D1 receptors are Gs-coupled, a GPR52 agonist should functionally resemble a D1 agonist and therefore exhibit effects on cortical function and hypofrontality. Several compounds are known to function as D1 agonists in the cortex, where they increase cortical function and resolve hypofrontality.

The efficacy of existing antipsychotic agents is reportedly mediated by D2 antagonist activity on medium spiny neurons (MSNs) in the striatum. However, D2 antagonists produce side effects, such as motor symptoms and hyperprolactinemia. Since GPR52 co-localizes almost exclusively with the D2 receptor in the striatum and because GPR52 is Gs-coupled and D2 is Gi-coupled, a GPR52 agonist should functionally resemble a D2 antagonist and therefore exhibit antipsychotic efficacy. Further, because many of the side effects associated with D2 antagonists are mediated by the D2 receptor, GPR52 agonists could avoid the side effects associated with existing D2 antagonists.

Based on the expression pattern, co-localization, intracellular signaling, and functional properties, it is suggested that GPR52 is a significant modulator of brain function with relevance for the treatment of several neurological and psychiatric disorders, including those described below:

(1) Hypofrontality

Decreased blood flow in the prefrontal cortex (hypofrontality) is symptomatic of several neurological conditions, including the cognitive and negative symptoms associated with schizophrenia, attention deficit hyperactivity disorder (ADHD), bipolar disorder, major depressive disorder, and hypofrontality associated with substance abuse. Dopaminergic transmission in the prefrontal cortex is mainly mediated by D1 receptors, and D1 dysfunction has been linked to cognitive impairment and negative symptoms in schizophrenia (Goldman-Rakic P S, Castner S A, Svensson T H, Siever U, Williams G V (2004) *Targeting the dopamine D1 receptor in schizophrenia: insights for cognitive dysfunction. Psychopharmacology* 174, 3-16). Increasing function in the prefrontal cortex with a GPR52 agonist is therefore useful for the treatment of symptoms associated with hypofrontality.

(2) Movement Disorders

The striatum is involved in the control of movement. Pathology of the striatum is associated with many movement disorders, including hyperkinetic movement disorders characterized by excessive abnormal involuntary movements (known as hyperkinesias). Examples of hyperkinetic movement disorders include tremors, dystonia, chorea, ballism, athetosis, tics/Tourette's syndrome, Huntington's disease, myoclonus and startle syndromes, stereotypies, and akathisia.

In the striatum, GPR52 is almost exclusively expressed on neurons of the indirect striatal pathway. Hyperkinesias are associated with the dysfunction of inhibitory, D2-expressing neurons of this pathway. This dysfunction leads to the inability to inhibit movement, resulting in tics, chorea, vocalizations, tremors, and other hyperkinetic symptoms. For example, early hyperkinetic motor symptoms in Huntington's disease are the result of selective damage to the indirect, D2-containing pathway (Albin R L, Reiner A, Anderson K D, Penney J B, Young A B. (1990) *Striatal and nigral neuron subpopulations in rigid Huntington's disease: implications for the functional anatomy of chorea and rigidity-akinesia. Ann Neurol.* 27, 357-365). Further, D2 receptor binding in striatum is associated with the severity of Tourette syndrome symptoms (Wolf S S, Jones D W, Enable M B, Gorey J G, Lee K S, Hyde T M, Coppola R, Weinberger D R (1996) *Tourette syndrome: prediction of phenotypic variation in monozygotic twins by caudate nucleus D2 receptor binding. Science* 273, 1225-1227).

The stimulation of GPR52 with agonists activates the indirect striatal pathway, leading to more inhibitory control over movement and the resolution of hyperkinetic symptoms. The GPR52 agonists disclosed herein are therefore useful for the treatment of such symptoms.

(3) Psychotic Disorders

The psychotic symptoms of schizophrenia result from overactive presynaptic dopamine activity in the striatum (Howes O D, Kapur S (2009) *The dopamine hypothesis of schizophrenia: version III—the final common pathway. Schizophr Bull.* 35, 549-562). The clinical efficacy of existing antipsychotic drugs for treating psychotic symptoms is dependent on blockade of the D2 receptor. All known antipsychotic drugs with efficacy for the treatment of psychosis are either antagonists or partial agonists at the dopamine D2 receptor (Remington G, Kapur S (2010) *Antipsychotic dosing: how much but also how often? Schizophr Bull.* 36, 900-903). While these antipsychotic drugs can treat the positive (or psychotic) symptoms of schizophrenia, they do not treat other aspects of schizophrenia, such as the negative symptoms or cognitive impairment. Based on the co-expression of the GPR52 and the dopamine D2 receptor, GPR52 agonists should treat the psychotic symptoms associated with schizophrenia. Additionally, since the mechanism of action of GPR52 agonists is unique to known D2 receptor associated antipsychotic drugs, it would be anticipated that GPR52 agonists augment the anti-psychotic efficacy of known neuroleptics. This should result not only in improved anti-psychotic efficacy but could be used to lower the dose of anti-psychotic drugs, thereby lowering their associated side effects. Increased serum prolactin levels is one of the prominent side effect profiles of known D2R antagonist anti-psychotics, whereas GPR52 agonists have been demonstrated to lower serum prolactin levels, therefore, co-application of GPR52 agonists with D2R antagonist anti-psychotics may normalize serum prolactin levels, thereby lowering the side effects associated with the D2R antagonist anti-psychotic. In addition, GPR52 agonists should treat the psychotic symptoms associated with various psychiatric indications, including schizoaffective disorder, schizotypal disorder, schizophreniform disorder, treatment resistant schizophrenia, drug-induced psychotic disorder, bipolar disorder, autism-spectrum disorder, and attenuated psychosis syndrome. Furthermore, GPR52 agonists should treat the psychotic and neuropsychiatric symptoms associated with various neurodegenerative indications, including Parkinson's disease, Alzheimer's disease, Frontotemporal dementia, Vascular cognitive impairment and Dementia with Lewy Bodies. These antipsychotic drugs are also associated with significant side effect profiles, including weight gain, metabolic syndrome, diabetes, hyperlipidemia, hyperglycemia, insulin resistance, extrapyramidal symptoms, hyperprolactinemia, and tardive dyskinesia. Because GPR52 agonists should functionally resemble D2 antagonists, the GPR52 agonists disclosed herein are useful for the treatment of psychotic disorders.

(4) Other D1-Related Disorders

Several neurological and psychiatric drugs are known to function as D1 agonists, including A-86929, dinapsoline, doxanthrine, SKF-81297, SKF-82958, SKF-38393, fenoldopam, 6-Br-APB, and stepholoidine. Because GPR52 agonists should functionally resemble D1 agonists (and are co-localized), the GPR52 agonists disclosed herein are useful for the treatment of disorders treatable by D1 agonists, including but not limited to addiction (e.g., cocaine addiction), hypertension, restless leg syndrome, Parkinson's disease, and depression. Furthermore, based on its expression pattern and functional coupling, GPR52 agonists are useful for the treatment of the cognitive deficits associated with schizophrenia, schizoaffective, schizophreniform and schizotypal disorders, treatment resistant schizophrenia, attenuated psychosis syndrome and autism-spectrum disorder, bipolar disease, Alzheimer's disease, Parkinson's disease, Frontotemporal dementia (Pick's disease), Lewy-body dementia, Vascular dementia, post-stroke dementia, and Creutzfeldt-Jakob disease.

(5) Other D2-Related Disorders

Several neurological and psychiatric drugs are known to function as D2 antagonists, including atypical antipsychotics (e.g., aripiprazole, clozapine, olanzapine, and ziprasidone), domperidone, eticlopride, fallypride, desmethoxyfallypride, L-741,626, raclopride, hydroxyzine, itopride, SV 293, typical antipsychotics, yohimibine, amisulpride, and UH-232. Because GPR52 agonists should functionally resemble D2 antagonists, the GPR52 agonists disclosed herein are useful for the treatment of disorders treatable by D2 antagonists, including but not limited to psychotic disorders, detachment, anxiety, anxiety/tension associated with psychoneurosis, acute mania, agitation, mania in bipolar disorder, dysthymia, nausea, vomiting, gastrointestinal conditions, dyspepsia, and addiction (e.g., cocaine addiction, amphetamine addiction, etc.).

Therefore it is believed that GPR52 agonists are promising candidates for improving diseases of the central nervous system.

GPR52 modulating compounds have already been disclosed in WO2009/157196; WO2009/107391, WO2011/078360, WO2011/093352, WO2011/145735, WO2012/020738 as well as WO2016/176571.

AIM OF THE INVENTION

It has now been found that compounds of the present invention according to general formula (I) are effective agonists of GPR52.

In addition to the agonistic property toward GPR52 and other properties like a low to moderate hERG channel inhibition the compounds of the present invention are also especially useful as medicaments because they are metabolized in an aldehyde oxidase-mediated metabolism, which contributes to a diversified overall metabolism and subsequently leads to a reduced risk for pharmacokinetic drug-drug interactions via Cytochrome P450 enzymes.

The term drug-drug interaction refers to the influence of one drug upon another, typically occurring if a drug affects the function or expression of a metabolic enzyme or a transporter. The most serious pharmacokinetic interactions are those in which the second drug changes the clearance of the first one. An example is the inhibition of metabolism of one drug by a co-administered drug: there will be an increase in the plasma concentration of the first drug that could result in a clinically relevant increase of the therapeutic response or increased toxicity.

Drug metabolism primarily occurs in the liver and intestine. These organs express a wide variety of drug metabolizing enzymes and are responsible for the biotransformation of many drugs. Phase I oxidative metabolism occurs primarily through the cytochrome P450 (CYP) family of enzymes located in the hepatic endoplasmic reticulum but can also be mediated by non-CYP enzymes such as aldehyde oxidase. These functionalizing reactions are often followed by conjugation reactions (Phase II) in order to increase the excretability of the xenobiotic.

Cytochrome P450 (CYP) enzymes are considered the major enzyme family capable of catalyzing oxidative biotransformation (phase 1 metabolism) of most drugs and other lipophilic xenobiotics (Zanger U M, Schwab M. (2013) *Cytochrome P450 enzymes in drug metabolism: regulation of gene expression, enzyme activities, and impact of genetic variation. Pharmacol Ther. Apr;* 138(1): 103-41), whereas metabolism mediated through aldehyde oxidase in marketed drugs remains scarce to date (Scerny, M A. (2016) *Prevalence of Non-Cytochrome P450-Mediated Metabolism in Food and Drug Administration-Approved Oral and Intravenous Drugs:* 2006-2015. *Drug Metab. Dispos.* 44(8), 1246-1252).

It is therefore advantageous to extend a drug's metabolism to non-CYP metabolic pathways, such as aldehyde oxidase-mediated metabolism, in order to reduce the risk of adverse drug-drug interactions with the far more common CYP-interacting medications.

In clinical psychiatry, combination pharmacotherapy is commonly used to treat patients with comorbid psychiatric or physical illnesses, to control the side effects of a specific drug or to augment a medication effect. However, said polypharmacy approaches involve a high risk for CYP-mediated drug-drug interactions. Therefore, the use of drugs with low potential for drug interactions is desirable, especially for elderly patients who are more likely to take multiple medications concurrently (Spina E, de Leon, J. (2007) *Metabolic Drug Interactions with Newer Antipsychotics: A Comparative Review. Basic Clin. Pharmacol. Toxicol.* 100, 4-22).

Therefore, the involvement of an additional, non-CYP-dependent oxidative metabolic pathway, i.e. via aldehyde oxidase, which results in a more diversified metabolism and subsequently to a reduced risk for drug-drug interactions, is highly desirable.

In addition to their agonistic property towards GPR52, compounds of the present invention are metabolized by aldehyde oxidase-mediated oxidative biotransformations as significant part of their overall oxidative metabolism. Consequently, compounds of the present invention are more viable for human therapy.

Inhibition of the hERG channel and subsequent delayed cardiac repolarization is associated with an increased risk for a specific polymorphic ventricular tachyarrhythmia, torsade de pointes, as established by Sanguinetti et al. (1995, Cell, 81 (2): 299-307) and subsequent evidence. To minimize this risk, screening against hERG channel inhibition in an in vitro system using heterologous expression of the hERG channel is common practice and an important part of later preclinical profiling as recommended by the ICH guideline S 7 B (International Conference on Harmonization (2005): ICH Topic S 7 B; The nonclinical Evaluation of the Potential for delayed Ventricular Repolarization (QT Interval Prolongation) by Human Pharmaceuticals). Therefore, low hERG channel inhibition or interaction, such as shown by the compounds of the present invention, is highly desirable. Consequently, compounds of the present invention are more viable for human therapy. Accordingly, one aspect of the invention refers to compounds according to formula (I), or salts thereof as agonists of GPR52.

Accordingly, one aspect of the invention refers to compounds according to formula (I), or pharmaceutically acceptable salts thereof as agonists of GPR52.

Another aspect of the invention refers to compounds according to formula (I), or pharmaceutically acceptable salts thereof as agonists of GPR52 with more diversified metabolism including non-CYP enzyme dependent metabolic pathways and subsequently reduced risk for CYP mediated drug-drug-interactions.

Another aspect of the invention refers to compounds according to formula (I), or pharmaceutically acceptable salts thereof as agonists of GPR52 with more diversified metabolism including non-CYP enzyme dependent metabolic pathways and subsequently reduced risk for CYP mediated drug-drug-interactions and low to moderate hERG channel inhibition.

In a further aspect this invention relates to pharmaceutical compositions, containing at least one compound according to formula (I), or pharmaceutically acceptable salts thereof, optionally together with one or more inert carriers and/or diluents.

A further aspect of the present invention relates to compounds according to formula (I), or pharmaceutically acceptable salts thereof or pharmaceutical compositions comprising compounds according to formula (I), or pharmaceutically acceptable salts thereof for the use in the prevention and/or treatment of disorders related to insufficient GPR52 activity.

Another aspect of the invention relates to processes of manufacture of the compounds of the present invention.

A further aspect of the present invention relates to compounds according to formula (I), or pharmaceutically acceptable salts thereof or pharmaceutical compositions comprising compounds according to formula (I), or pharmaceutically acceptable salts thereof for the use in the prevention and/or treatment of diseases or conditions which can be influenced by activation of GPR52, such as Schizophrenia; Positive symptoms associated with schizophrenia, schizoaffective, schizophreniform and schizotypal disorders, treatment resistant schizophrenia, attenuated psychosis syndrome and autism-spectrum disorder; Augmentation treatment of the positive symptoms associated with schizophrenia; Augmentation of antipsychotics to improve the treatment of the positive symptoms associated with schizophrenia or to lower the dose, and thereby side effects, of antipsychotics; Negative symptoms associated with schizophrenia, schizoaffective, schizophreniform and schizotypal disorders, treatment resistant schizophrenia, attenuated psychosis syndrome and autism-spectrum disorder; Cognitive impairment associated with schizophrenia (CIAS), schizoaffective, schizophreniform and schizotypal disorders, treatment resistant schizophrenia, attenuated psychosis syndrome and autism-spectrum disorder; Treatment resistant schizophrenia; Schizoaffective disorder; Schizophreniform disorder; Schizotypal disorder; Drug-induced psychosis; Bipolar disorder; Attenuated psychosis syndrome and the Neuropsychiatric symptoms associated with Alzheimer's Disease, Parkinson's Disease, Vascular dementia, and Frontotemporal dementia; Autism spectral disorder (ASD); Impulse control disorder induced by D2 receptor agonists; Gambling Disorder induced by D2 receptor agonists, Tourette's syndrome; Cognitive deficits associated with Alzheimer's disease, Parkinson's disease, Vascular dementia, and Frontotemproal dementia; Depression; Attention deficit hyperactivity disorder; Major depressive disorder; Drug addiction; Anxiety; Mania in Bipolar disorder; Acute mania; Agitation; Detachment; and the treatment of symptoms associated with hypofrontality (e.g. Hypofrontality associated with drug abuse) and/or hyperkinetic symptoms. Other aims of the present invention will become apparent to the skilled man directly from the foregoing and following remarks.

DETAILED DESCRIPTION

In a first aspect the present invention relates to compounds of general formula (I)

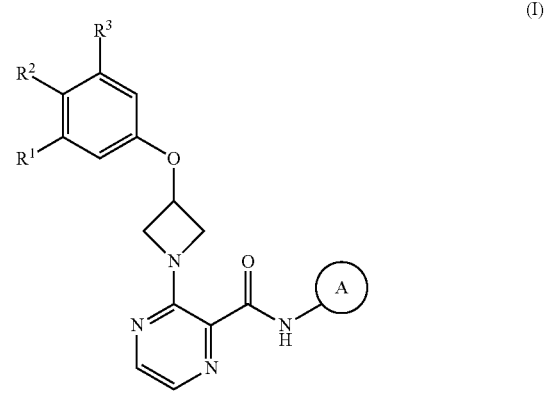

wherein
A is selected from the group $A^a$ consisting of

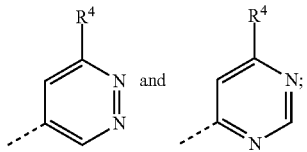

$R^1$ is selected from the group $R^{1a}$ consisting of
H— and F—;
$R^2$ is selected from the group $R^{2a}$ consisting of
H— and F—;
$R^3$ is selected from the group $R^{3a}$ consisting of
halogen, $F_2HCO$—, $F_3CO$—, $F_2HC$— and $F_3C$—;
$R^4$ is selected from the group $R^{4a}$ consisting of
H— and $C_{1-3}$-alkyl-,
  wherein the above mentioned $C_{1-3}$-alkyl-group may optionally be substituted with 1 to 5 substituents independently selected from the group consisting of fluorine;
or a salt thereof.

Unless otherwise stated, the groups, residues, and substituents, particularly A, $R^1$, $R^2$, $R^3$ and $R^4$ are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^b$ consisting of

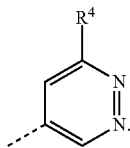

In a further embodiment of the present invention
$R^3$ is selected from the group $R^{3b}$ consisting of
F—, Cl—, and $F_2HC$—.
In a further embodiment of the present invention
$R^3$ is selected from the group $R^{3c}$ consisting of
F—.
In a further embodiment of the present invention
$R^4$ is selected from the group $R^{4b}$ consisting of
H—, $C_{1-2}$-alkyl- and $F_3C$—.
In a further embodiment of the present invention
$R^4$ is selected from the group $R^{4c}$ consisting of
$C_{1-2}$-alkyl-.

Each $A^x$, $R^{1x}$, $R^{2x}$, $R^{3x}$ and $R^{4x}$ represents a characterized, individual embodiment for the corresponding substituent as described above. Thus given the above definitions, individual embodiments of the first aspect of the invention are fully characterized by the term ($A^x$, $R^{1x}$, $R^{2x}$, $R^{3x}$ and $R^{4x}$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows such embodiments E-1 to E-18 of the invention that are considered preferred. Embodiment E-18, represented by the entries in the last row of Table 1, is the most preferred embodiment.

TABLE 1

Embodiments E-1 to E-18 of the invention

|      | $A^x$ | $R^{1x}$ | $R^{2x}$ | $R^{3x}$ | $R^{4x}$ |
|------|-------|----------|----------|----------|----------|
| E-1  | $A^a$ | $R^{1a}$ | $R^{2a}$ | $R^{3a}$ | $R^{4a}$ |
| E-2  | $A^a$ | $R^{1a}$ | $R^{2a}$ | $R^{3a}$ | $R^{4b}$ |
| E-3  | $A^a$ | $R^{1a}$ | $R^{2a}$ | $R^{3a}$ | $R^{4c}$ |
| E-4  | $A^a$ | $R^{1a}$ | $R^{2a}$ | $R^{3b}$ | $R^{4a}$ |
| E-5  | $A^a$ | $R^{1a}$ | $R^{2a}$ | $R^{3b}$ | $R^{4b}$ |
| E-6  | $A^a$ | $R^{1a}$ | $R^{2a}$ | $R^{3b}$ | $R^{4c}$ |
| E-7  | $A^a$ | $R^{1a}$ | $R^{2a}$ | $R^{3c}$ | $R^{4a}$ |
| E-8  | $A^a$ | $R^{1a}$ | $R^{2a}$ | $R^{3c}$ | $R^{4b}$ |
| E-9  | $A^a$ | $R^{1a}$ | $R^{2a}$ | $R^{3c}$ | $R^{4c}$ |
| E-10 | $A^b$ | $R^{1a}$ | $R^{2a}$ | $R^{3a}$ | $R^{4a}$ |
| E-11 | $A^b$ | $R^{1a}$ | $R^{2a}$ | $R^{3a}$ | $R^{4b}$ |
| E-12 | $A^b$ | $R^{1a}$ | $R^{2a}$ | $R^{3a}$ | $R^{4c}$ |
| E-13 | $A^b$ | $R^{1a}$ | $R^{2a}$ | $R^{3b}$ | $R^{4a}$ |
| E-14 | $A^b$ | $R^{1a}$ | $R^{2a}$ | $R^{3b}$ | $R^{4b}$ |
| E-15 | $A^b$ | $R^{1a}$ | $R^{2a}$ | $R^{3b}$ | $R^{4c}$ |
| E-16 | $A^b$ | $R^{1a}$ | $R^{2a}$ | $R^{3c}$ | $R^{4a}$ |
| E-17 | $A^b$ | $R^{1a}$ | $R^{2a}$ | $R^{3c}$ | $R^{4b}$ |
| E-18 | $A^b$ | $R^{1a}$ | $R^{2a}$ | $R^{3c}$ | $R^{4c}$ |

Accordingly, for example E-2 covers compounds of formula (I),
wherein
A is selected from the group $A^a$ consisting of

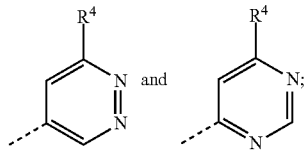

$R^1$ is selected from the group $R^{1a}$ consisting of
H— and F—;
$R^2$ is selected from the group $R^{2a}$ consisting of
H— and F—;
$R^3$ is selected from the group $R^{3a}$ consisting of
halogen, $F_2HCO$—, $F_3CO$—, $F_2HC$— and $F_3C$—;
$R^4$ is selected from the group $R^{4b}$ consisting of
H—, $C_{1-2}$-alkyl- and $F_3C$—.
or a salt thereof.

Accordingly, for example E-10 covers compounds of formula (I),
wherein
A is selected from the group $A^b$ consisting of

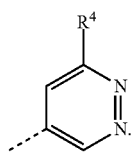

$R^1$ is selected from the group $R^{1a}$ consisting of
H— and F—;
$R^2$ is selected from the group $R^{2a}$ consisting of
H— and F—;
$R^3$ is selected from the group $R^{3a}$ consisting of
halogen, $F_2HCO$—, $F_3CO$—, $F_2HC$— and $F_3C$—;
$R^4$ is selected from the group $R^{4a}$ consisting of
H— and $C_{1-3}$-alkyl-, wherein the above mentioned $C_{1-3}$-alkyl-group may optionally be substituted with 1 to 5 substituents independently selected from the group consisting of fluorine;

or a salt thereof.

Accordingly, for example E-18 covers compounds of formula (I), wherein

A is selected from the group $A^b$ consisting of

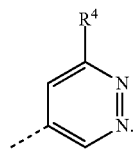

$R^1$ is selected from the group $R^{1a}$ consisting of H— and F—;

$R^2$ is selected from the group $R^{2a}$ consisting of H— and F—;

$R^3$ is selected from the group $R^{3c}$ consisting of F—.

$R^4$ is selected from the group $R^{4c}$ consisting of $C_{1-2}$-alkyl-.

or a salt thereof.

Further preferred are the following compounds listed in Table 2:

| No. | Structure |
|---|---|
| I | |
| II | |
| III | 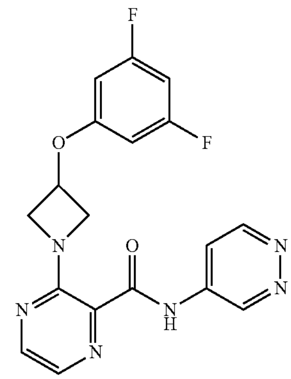 [SMILES: O=C(Nc1ccnnc1)c1nccnc1N1CC(Oc2cc(F)cc(F)c2)C1] |
| IV | 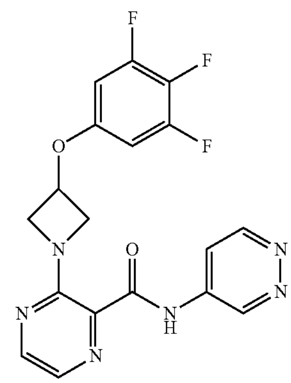 [SMILES: O=C(Nc1ccnnc1)c1nccnc1N1CC(Oc2cc(F)c(F)c(F)c2)C1] |
| V | 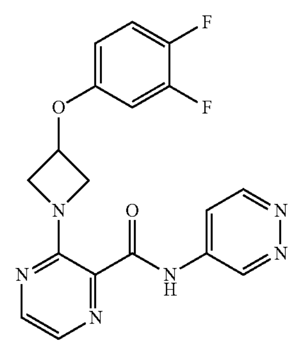 [SMILES: O=C(Nc1ccnnc1)c1nccnc1N1CC(Oc2ccc(F)c(F)c2)C1] |
| VI | 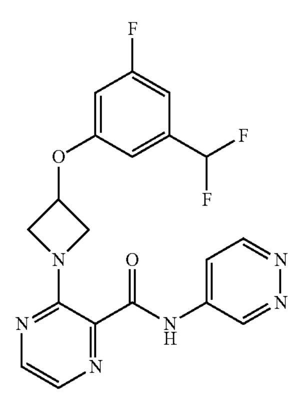 [SMILES: O=C(Nc1ccnnc1)c1nccnc1N1CC(Oc2cc(F)cc(C(F)F)c2)C1] |

-continued

| No. | Structure |
|-----|-----------|
| VII | 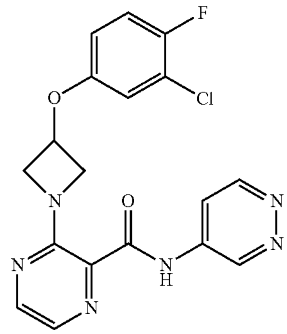 [SMILES: O=C(Nc1ccnnc1)c1nccnc1N1CC(Oc2ccc(F)c(Cl)c2)C1] |
| VIII | 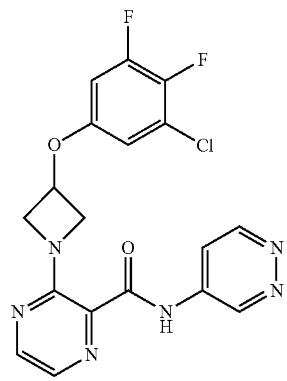 [SMILES: O=C(Nc1ccnnc1)c1nccnc1N1CC(Oc2cc(F)c(F)c(Cl)c2)C1] |
| IX | 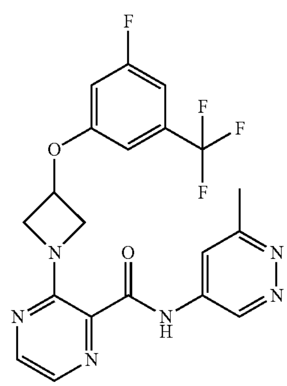 [SMILES: Cc1cc(NC(=O)c2nccnc2N2CC(Oc3cc(F)cc(C(F)(F)F)c3)C2)cnn1] |
| X | 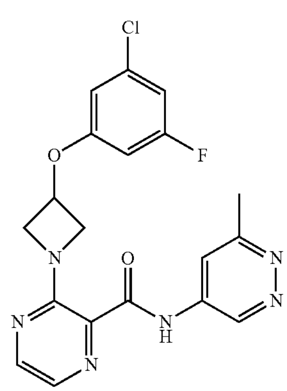 [SMILES: Cc1cc(NC(=O)c2nccnc2N2CC(Oc3cc(F)cc(Cl)c3)C2)cnn1] |

-continued

| No. | Structure |
|-----|-----------|
| XI | |
| XII | |
| XIII | |
| XIV | |

| No. | Structure |
|-----|-----------|
| XV | (3,4,5-trifluorophenoxy-azetidinyl pyrazine carboxamide N-(6-methylpyridazin-4-yl)) |
| XVI | (3-chloro-4-fluorophenoxy-azetidinyl pyrazine carboxamide N-(6-methylpyridazin-4-yl)) |
| XVII | (3-fluoro-5-(trifluoromethyl)phenoxy-azetidinyl pyrazine carboxamide N-(6-ethylpyridazin-4-yl)) |
| XVIII | (3-chloro-5-fluorophenoxy-azetidinyl pyrazine carboxamide N-(6-ethylpyridazin-4-yl)) |
| XIX | (3-chloro-4-fluorophenoxy-azetidinyl pyrazine carboxamide N-(6-ethylpyridazin-4-yl)) |
| XX | (3,4,5-trifluorophenoxy-azetidinyl pyrazine carboxamide N-(6-ethylpyridazin-4-yl)) |
| XXI | (3,4-difluorophenoxy-azetidinyl pyrazine carboxamide N-(6-ethylpyridazin-4-yl)) |
| XXII | (3-fluoro-5-(difluoromethyl)phenoxy-azetidinyl pyrazine carboxamide N-(6-ethylpyridazin-4-yl)) |

| No. | Structure |
|---|---|
| XXIII | 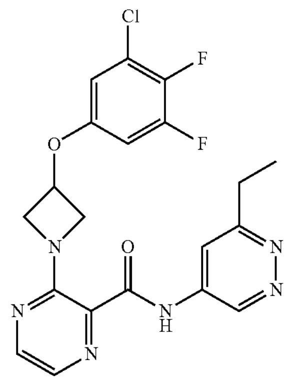 [SMILES: CCc1cc(NC(=O)c2nccnc2N2CC(Oc3cc(F)c(F)c(F)c3)C2)cnn1] |
| XXIV | 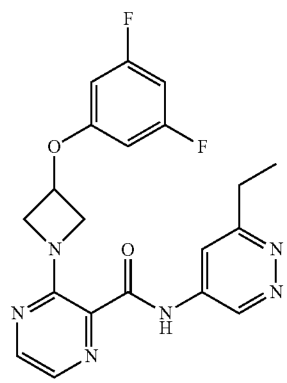 [SMILES: CCc1cc(NC(=O)c2nccnc2N2CC(Oc3cc(F)cc(F)c3)C2)cnn1] |
| XXV | 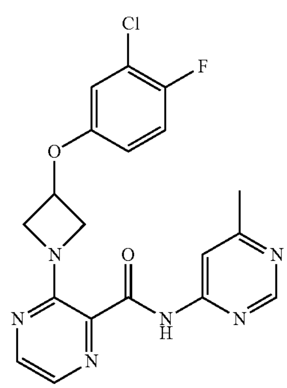 [SMILES: Cc1cc(NC(=O)c2nccnc2N2CC(Oc3ccc(F)c(Cl)c3)C2)ncn1] |
| XXVI | 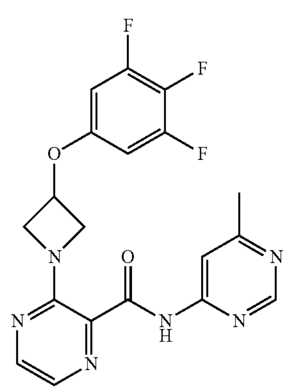 [SMILES: Cc1cc(NC(=O)c2nccnc2N2CC(Oc3cc(F)c(F)c(F)c3)C2)ncn1] |

| No. | Structure |
|---|---|
| XXVII | 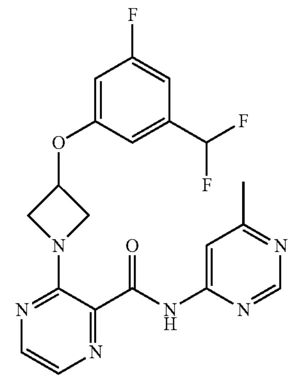 [SMILES: Cc1cc(NC(=O)c2nccnc2N2CC(Oc3cc(F)cc(C(F)F)c3)C2)ncn1] |
| XXVIII | 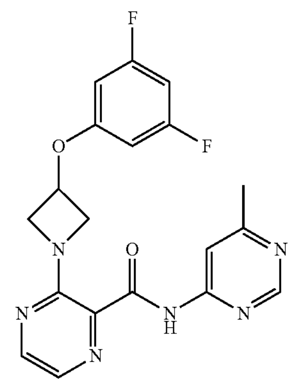 [SMILES: Cc1cc(NC(=O)c2nccnc2N2CC(Oc3cc(F)cc(F)c3)C2)ncn1] |
| XXIX | 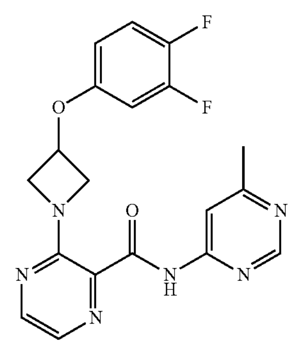 [SMILES: Cc1cc(NC(=O)c2nccnc2N2CC(Oc3ccc(F)c(F)c3)C2)ncn1] |
| XXX | 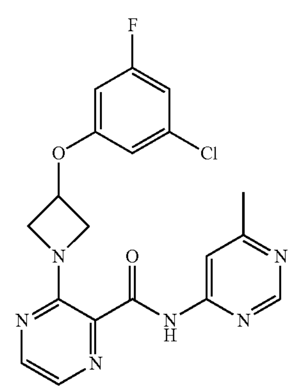 [SMILES: Cc1cc(NC(=O)c2nccnc2N2CC(Oc3cc(F)cc(Cl)c3)C2)ncn1] |

| No. | Structure |
|---|---|
| XXXI | 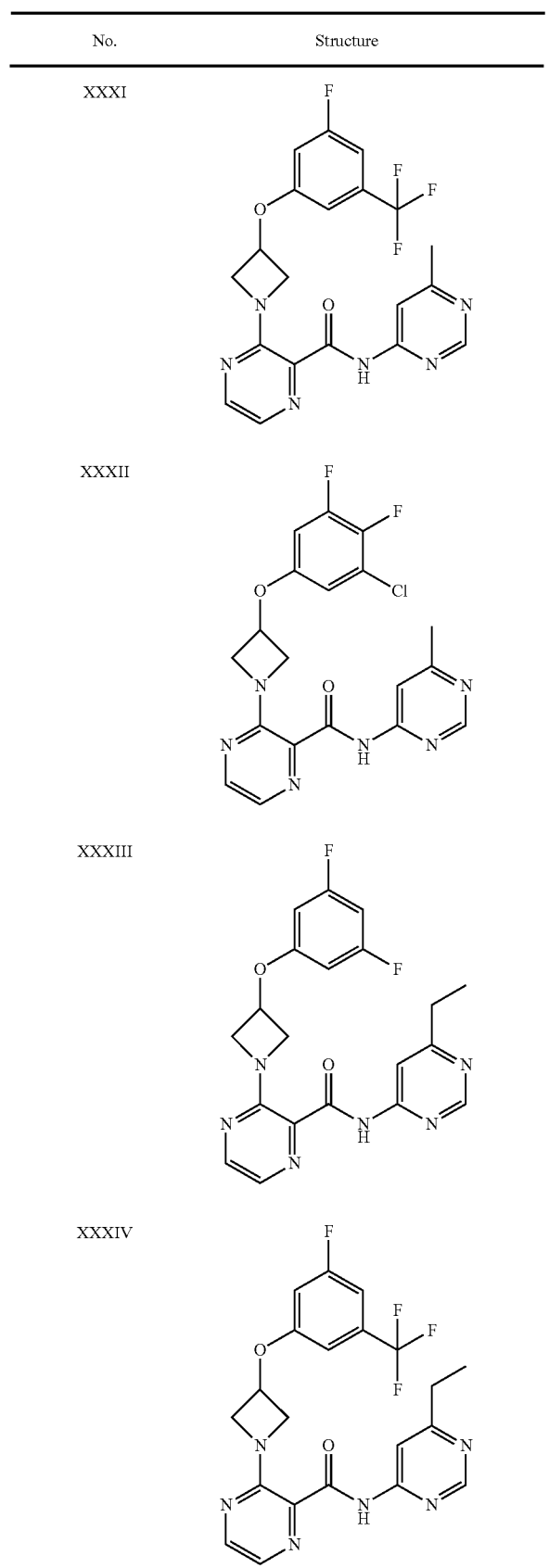 |
| XXXII | |
| XXXIII | |
| XXXIV | |
| No. | Structure |
|---|---|
| XXXV | 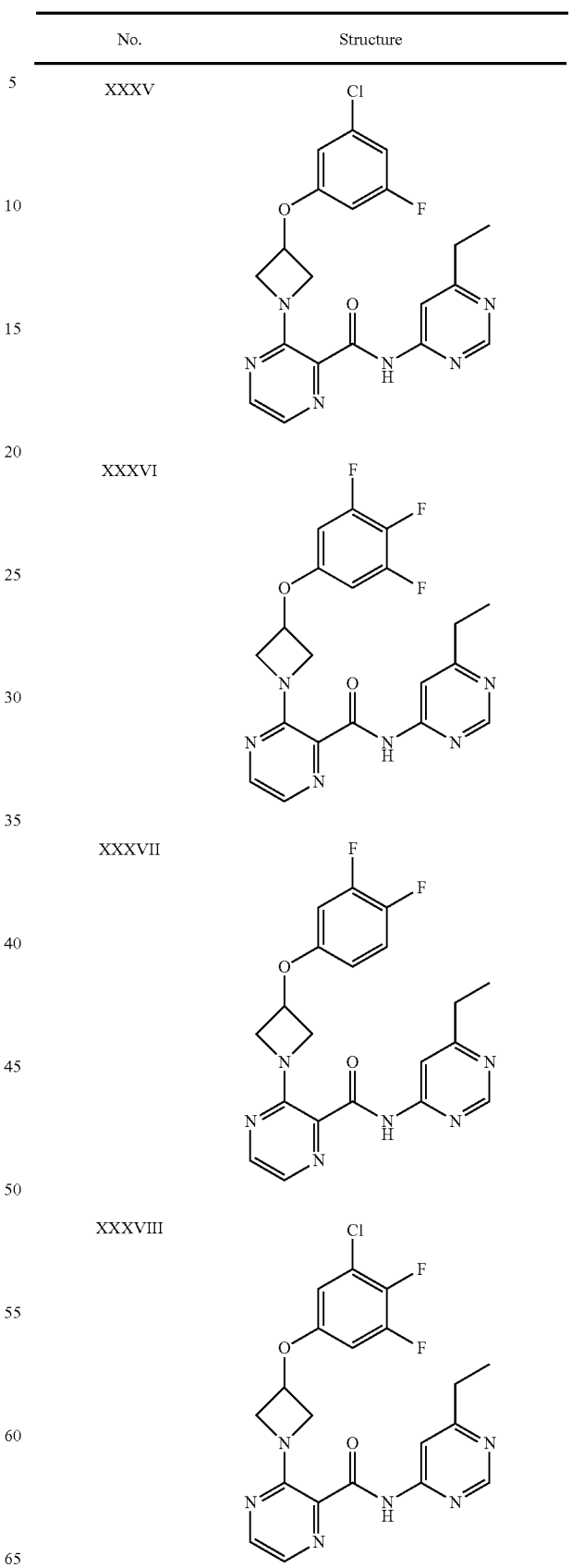 |
| XXXVI | |
| XXXVII | |
| XXXVIII | |

| No. | Structure |
|---|---|
| XXXIX | 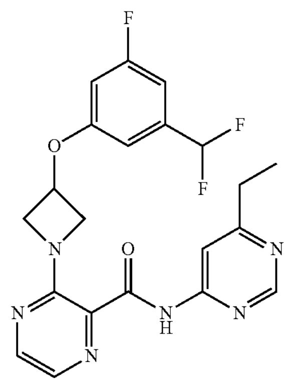 [SMILES: CCc1cc(NC(=O)c2nccnc2N2CC(Oc3cc(F)cc(C(F)F)c3)C2)ncn1] |
| XL | 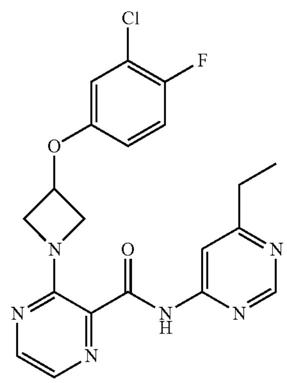 [SMILES: CCc1cc(NC(=O)c2nccnc2N2CC(Oc3ccc(F)c(Cl)c3)C2)ncn1] |
| XLI | 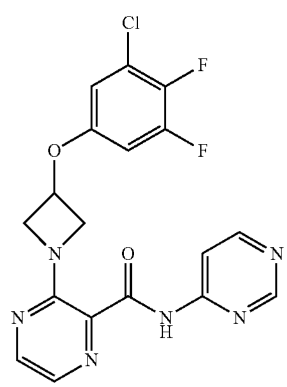 [SMILES: O=C(Nc1ccncn1)c1nccnc1N1CC(Oc2cc(F)c(F)c(Cl)c2)C1] |
| XLII | 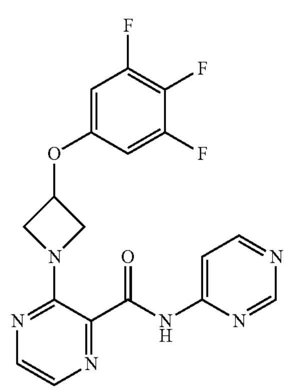 [SMILES: O=C(Nc1ccncn1)c1nccnc1N1CC(Oc2cc(F)c(F)c(F)c2)C1] |
| XLIII | |
| XLIV | |
| XLV | |
| XLVI | |

A further embodiment of the present invention covers the compounds listed in Table 2 in form of their pharmaceutically acceptable salts.

In a further aspect, the present invention relates to a compound of the present invention or a pharmaceutically acceptable salt thereof for use as a medicament.

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core molecule or to the group to which the substituent is attached.

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

A dotted line - - - - - - - is used in sub-formulas to indicate the bond or attachment point which is connected to the core molecule, rest of the molecule or to the substituent to which it is bound as defined.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric add and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom/group is replaced with a selection from the indicated group, provided that the designated atom's viable valence number is not exceeded, and that the substitution results in a stable compound.

The term "halogen" denotes fluorine (F), chlorine (Cl), bromine (Br) and iodine (I).

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

Preparation

The following Schemes shall illustrate generally how to manufacture the compounds of the present invention by way of example. The abbreviated substituents may be as defined above if not defined otherwise within the context of the schemes.

General Synthetic Methods

The invention also provides a process for making compounds of formula (I). Unless specified otherwise, $R^1$, $R^2$, $R^3$, $R^4$, ring A in the formulas below shall have the meaning as defined for formula (I) in the detailed description of the invention above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), liquid chromatography-mass spectrometry (LC-MS) if desired, and intermediates and products may be purified by chromatography and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Scheme 1

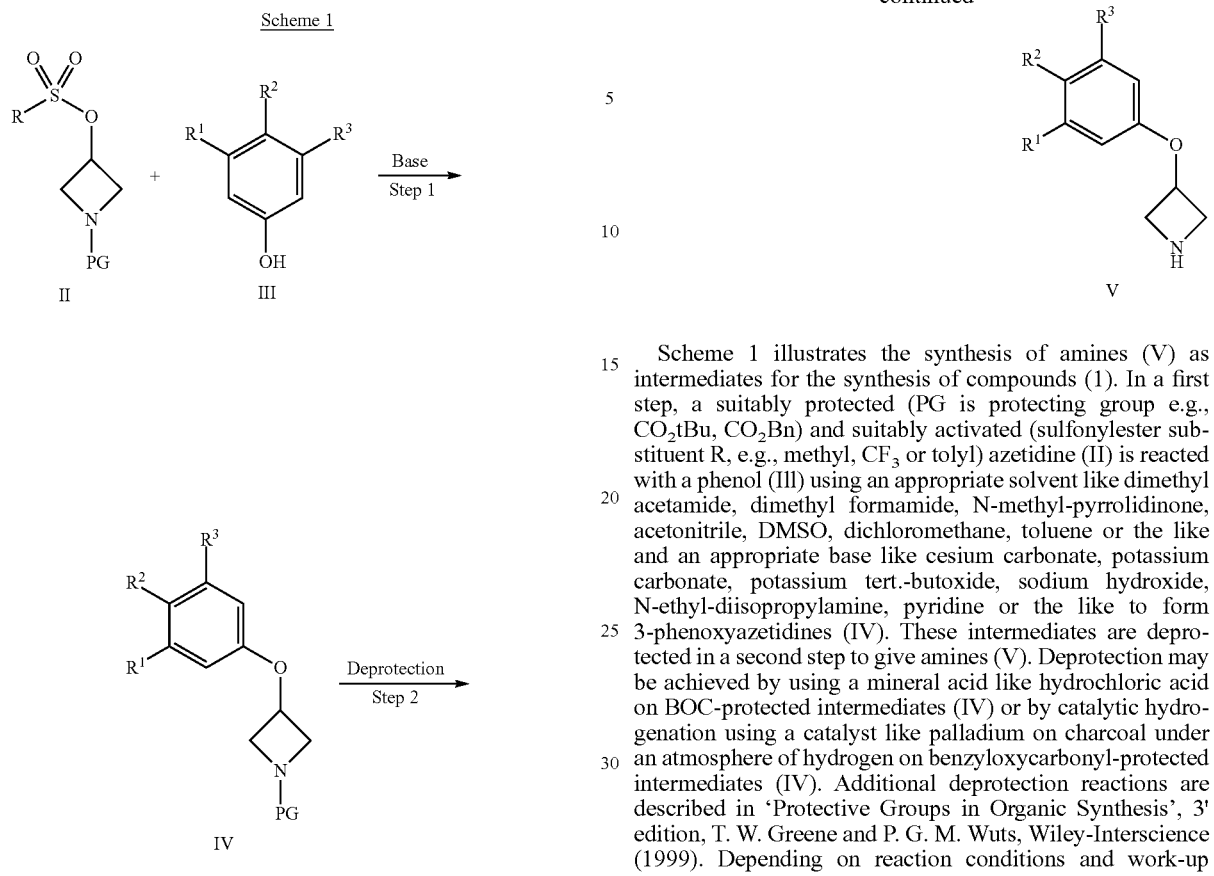

Scheme 1 illustrates the synthesis of amines (V) as intermediates for the synthesis of compounds (1). In a first step, a suitably protected (PG is protecting group e.g., $CO_2tBu$, $CO_2Bn$) and suitably activated (sulfonylester substituent R, e.g., methyl, $CF_3$ or tolyl) azetidine (II) is reacted with a phenol (III) using an appropriate solvent like dimethyl acetamide, dimethyl formamide, N-methyl-pyrrolidinone, acetonitrile, DMSO, dichloromethane, toluene or the like and an appropriate base like cesium carbonate, potassium carbonate, potassium tert.-butoxide, sodium hydroxide, N-ethyl-diisopropylamine, pyridine or the like to form 3-phenoxyazetidines (IV). These intermediates are deprotected in a second step to give amines (V). Deprotection may be achieved by using a mineral acid like hydrochloric acid on BOC-protected intermediates (IV) or by catalytic hydrogenation using a catalyst like palladium on charcoal under an atmosphere of hydrogen on benzyloxycarbonyl-protected intermediates (IV). Additional deprotection reactions are described in 'Protective Groups in Organic Synthesis', 3' edition, T. W. Greene and P. G. M. Wuts, Wiley-Interscience (1999). Depending on reaction conditions and work-up amines (V) may be obtained as salts.

Scheme 2

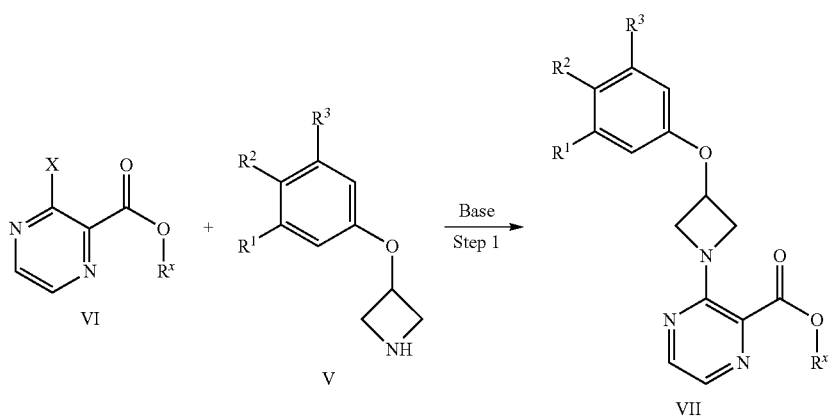

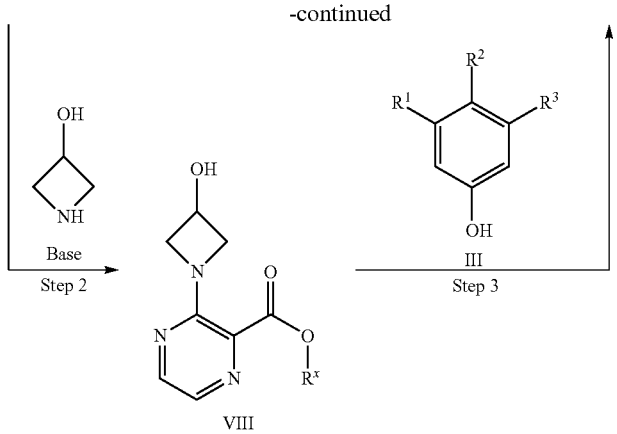

As shown in scheme 2, reacting the amine of formula (V) with a halo ester (VI) (X=halide, $R^x$=alkyl) in a nucleophilic aromatic substitution reaction (step 1), in a suitable solvent such as dioxane, THF, DMA or DMF and in the presence of a suitable base such as potassium tert-butoxide or NaH, provides ester compounds of formula (VII). Additionally, Buchwald-Hartwig-type cross coupling conditions may be used to form compounds (VII). For example, compounds (IV) (X=Cl, Br, I, $R^x$=alkyl) may be reacted with amines (V) in a suitable solvent such as toluene in the presence of a suitable catalyst such as palladium(II) acetate and a suitable ligand such as butyl-di-1-adamantyl-phosphine and a suitable base such as cesium carbonate to provide compounds of the general formula (VII).

Alternatively, halo ester (VI) may be reacted with hydroxy azetidine in a nucleophilic aromatic substitution reaction, in a suitable solvent such as DMA or the like and in the presence of a suitable base such as triethylamine, to give alcohols of the general formula (VIII). In a subsequent step, alcohols (VIII) may be converted into a phenyl ether compound of formula (VII) using the "Mitsunobu" method (see for examples *Tet. Lett.* 1994, 35, 2819 or *Synlett* 2005, 18, 2808): trialkyl or triaryl phosphine (such as tributyl phosphine or triphenyl phosphine) or solid-supported analogues such as polymer-bound triphenyl phosphine and a suitable dialkyl azadicarboxylate (e.g. DIAD, DEAD) are added to a compound of general formula (VIII) in the presence of an appropriate phenol (III) in a suitable solvent (e.g. THF or toluene) to generate aryl ether of the general formula (VII).

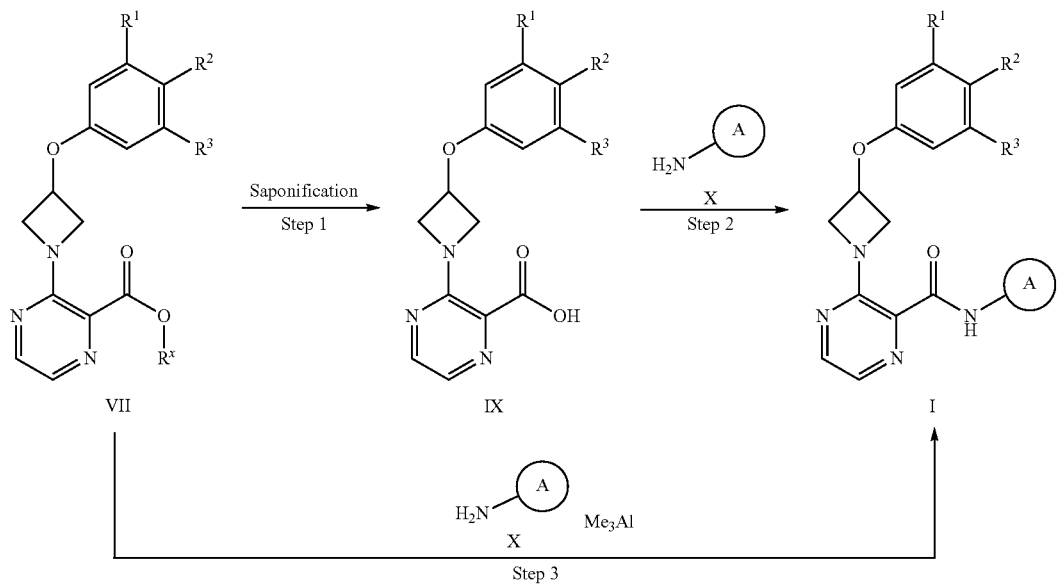

Scheme 3

The preparation of compounds of general formula (I) is illustrated in scheme 3. In a first step carboxylic acid esters (VII) can be hydrolyzed with the appropriate hydroxide base (e.g., lithium hydroxide, sodium hydroxide, potassium hydroxide, barium hydroxide or the like) in solvent/water mixtures such as acetone/water, 1,4-dioxane/water, THF/water to form the corresponding carboxylic acids (IX) upon acidification.

Peptide coupling reactions known to the person skilled in the art (see for example M. Bodanszky, 1984, The Practice of Peptide Synthesis, Springer-Verlag) can be applied to react an amine of formula (X) with a carboxylic acid (IX) to yield a compound of general formula (I). For example, an amine (X) and a carboxylic acid (IX) in a suitable solvent such as acetonitrile, NMP, DMA or DMF in the presence of a suitable base such as DIPEA or 1-methyl-imidazole yields upon treatment with the coupling agent 2-chloro-4,5-dihydro-1,3-dimethyl-1H-imidazolium hexafluorophosphate (CIP), Mukaiyama's reagent, chloro-N,N,N',N'-tetramethylformamidinium hexafluorophosphate (TCFH) or 1-[bis(dimethylamino)methylene]-1H-1,2,3-triazolo[4,5-b]pyridinium 3-oxid hexafluorophosphate (HATU) form a compound of formula (I).

Alternatively, a carboxylic acid (IX) in a suitable solvent such as DCM, DMF or toluene upon treatment with 1-chloro-N,N-2-trimethylpropenylamine, thionyl chloride or oxalyl chloride yields an intermediate acid chloride, which is then treated with an amine of formula (X), in a suitable solvent such as DCM, THF or DMF, in the presence of a suitable base such as TEA, to provide a compound of formula (I).

Alternatively, amines (X), pre-activated with trimethyl aluminium, can be reacted directly with carboxylic acid esters (VII) in suitable solvent such as DCM, dichloroethane, THF or toluene to yield amides of general formula (I).

Scheme 4

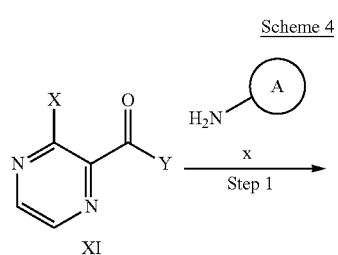

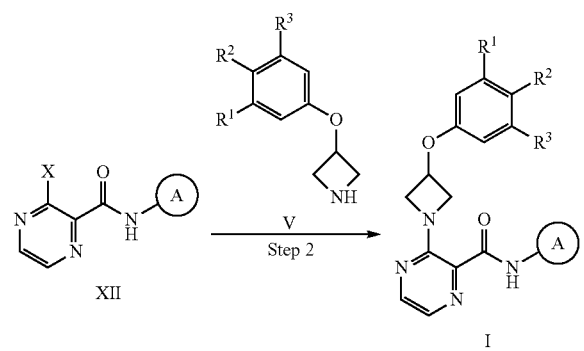

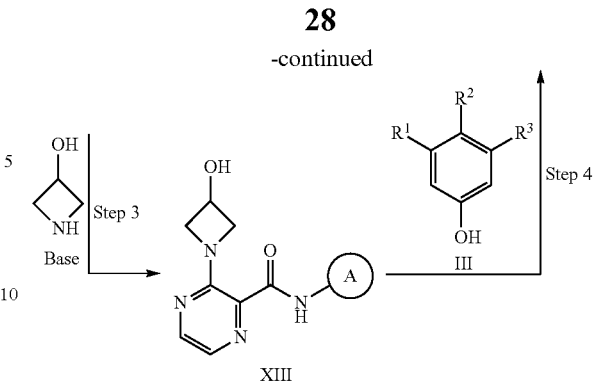

Alternatively, a compound of the general formula (I) can be synthesized as illustrated in scheme 4: peptide coupling reactions known to the person skilled in the art (see for example M. Bodanszky, 1984, The Practice of Peptide Synthesis, Springer-Verlag) can be applied in a first step to react an amine of formula (X) with a carboxylic acid (XI) (X=halide, Y=OH) to yield a halo amide of general formula (XII) (X=halide). For example, an amine (X) and a carboxylic acid (XI) (X=halide, Y=OH) in a suitable solvent such as acetonitrile, NMP, DMA or DMF in the presence of a suitable base such as DIPEA or 1-methyl-imidazole yields upon treatment with the coupling agent 2-chloro-4,5-dihydro-1,3-dimethyl-1H-imidazolium hexafluorophosphate (CIP), Mukaiyama's reagent, chloro-N,N,N',N'-tetramethylformamidinium hexafluorophosphate (TCFH) or 1-[bis(dimethylamino)methylene]-1H-1,2,3-triazolo[4,5-b]pyridinium 3-oxid hexafluorophosphate (HATU) form a halo amide of general formula (XII) (X=halide). Alternatively, a carboxylic acid (XI) (X=halide, Y=OH) in a suitable solvent such as DCM, DMF or toluene upon treatment with 1-chloro-N,N-2-trimethylpropenylamine, thionyl chloride or oxalyl chloride yields an intermediate acid chloride (XI) (Y=Cl), which is then treated with an amine of formula (X), in a suitable solvent such as DCM, THF or DMF, in the presence of a suitable base such as TEA, to provide a halo amide of general formula (XII) (X=halide). Alternatively, amines (X), pre-activated with trimethyl aluminium, can be reacted directly with carboxylic acid esters (XI) (X=halide, Y=alkyloxy) in suitable solvent such as DCM, dichloroethane, THF or toluene to yield halo amides of general formula (XII) (X=halide).

In a second step an amine of formula (V) is reacted with a halo amide (XII) (X=halide) in a nucleophilic aromatic substitution reaction, in a suitable solvent such as 2-propanol, dioxane, THF, NMP, DMA, DMF or toluene/water mixture and in the presence of a suitable base such as potassium tert-butoxide, NaH, potassium carbonate, pyridine, triethylamine or N-ethyl-diisopropylamine to give compounds of general formula (I). Additionally, Buchwald-Hartwig-type cross coupling conditions may be used to form final compounds (I). For example, compounds (XII) (X=Cl, Br, I) may be reacted with amines (V) in a suitable solvent such as toluene in the presence of a suitable catalyst such as palladium(II) acetate and a suitable ligand such as butyl-di-1-adamantyl-phosphine and a suitable base such as cesium carbonate to provide compounds of the general formula (I).

Alternatively, halo amide (XII) may be reacted with hydroxy azetidine in a nucleophilic aromatic substitution reaction, in a suitable solvent such as DMA or the like and in the presence of a suitable base such as triethylamine, to give alcohols of the general formula (XIII). In a subsequent step, alcohols (XIII) may be converted into compound of general formula (I) using the "Mitsunobu" method (see for examples *Tet. Lett.* 1994, 35, 2819 or *Synlett* 2005, 18, 2808): trialkyl or triaryl phosphine (such as tributyl phosphine or triphenyl phosphine) or solid-supported analogues such as polymer-bound triphenyl phosphine and a suitable dialkyl azadicarboxylate (e.g. DIAD, DEAD) are added to a compound of general formula (XIII) in the presence of an appropriate phenol (Ill) in a suitable solvent (e.g. THF or toluene) to generate compounds of the general formula (I).

Biological Examples

Homogeneous Time-Resolved Fluorescence (HTRF) Assay for Direct cAMP Measurement.

HTRF cAMP assays were performed using commercially available assay kits according to the manufacturer's instructions (cAMP Dynamic 2 Assay Kit; #62AM4PEJ, Cisbio Bioassays, Bedford, Mass.). An aliquot of CHO-K1 cells stably expressing recombinant human GPR52 is thawed and resuspended in cell buffer (1×PBS (w/o $Ca^{2+}/Mg^{2+}$)) at a density of 4×105 cells per mL Test compounds were solubilized in DMSO to 10 mM stock solutions and serially diluted in DMSO using 6-fold dilutions to generate 8-point dose response curves. These serially diluted samples were then diluted 1:50 in compound dilution buffer (1×PBS (w/o $Ca^{2+}/Mg^{2+}$) containing 0.5 mM IBMX, 0.1% BSA) to achieve a 4× stock. The diluted compounds were transferred (5 µL per well) in duplicate to the 384-well assay plate (Optiplate #6007290, PerkinElmer, Waltham, Mass.). Both a positive (reference compound) and negative (non-stimulated vehicle) control are included in each assay run in column 23. The cell suspension was subsequently dispensed into the 384-well assay plates at 15 µL per well (6000 cells) such that the compound was diluted to 1×. Column 24 on the plates did not receive cells and was reserved for a cAMP standard curve. After a one-hour incubation at room temperature, 10 µL of cAMP D2 reagent followed by 10 µL of cryptate reagent (provided in the Cisbio kit) was added to each well. Plates were then incubated at room temperature for one hour prior to reading. Time-resolved fluorescence measurements were collected on an EnVision® HTRF plate reader (PerkinElmer, Waltham, Mass.). Counts from the plate reader were fit to the cAMP standard curve included on each plate to determine the amount of cAMP in each test well. The % control was calculated based on the positive control set at 200% and the negative control set at 100%. Dose-response curves were generated from the cAMP data and analyzed using a nonlinear least squares curve-fitting program to obtain $EC_{50}$ values. Mean $EC_{50}$ values are provided in table 3.

TABLE 3

Activity of the examples compiled in the experimental part, based on the above described HTRF assay

| Example | GPR52 $EC_{50}$ [µM] | Example | GPR52 $EC_{50}$ [µM] | Example | GPR52 $EC_{50}$ [µM] | Example | GPR52 $EC_{50}$ [µM] |
|---|---|---|---|---|---|---|---|
| 1 | 0.009 | 2 | 0.009 | 3 | 0.019 | 4 | 0.005 |
| 5 | 0.010 | 6 | 0.006 | 7 | 0.010 | 8 | 0.004 |
| 9 | 0.014 | 10 | 0.004 | 11 | 0.006 | 12 | 0.003 |
| 13 | 0.009 | 14 | 0.004 | 15 | 0.005 | 16 | 0.004 |
| 17 | 0.011 | 18 | 0.006 | 19 | 0.004 | 20 | 0.005 |
| 21 | 0.002 | 22 | 0.007 | 23 | 0.006 | 24 | 0.006 |
| 25 | 0.004 | 26 | 0.006 | 27 | 0.011 | 28 | 0.012 |
| 29 | 0.005 | 30 | 0.008 | 31 | 0.017 | 32 | 0.008 |
| 33 | 0.010 | 34 | 0.030 | 35 | 0.008 | 36 | 0.006 |
| 37 | 0.003 | 38 | 0.009 | 39 | 0.012 | 40 | 0.005 |
| 41 | 0.012 | 42 | 0.023 | 43 | 0.045 | 44 | 0.037 |
| 45 | 0.014 | 46 | 0.007 | | | | |

In Vitro Metabolite Profiling

In vitro metabolite profiling to evaluate the involvement of aldehyde oxidase in addition to CYP-mediated metabolic pathways is based on the semiquantitative analysis of the formation of oxygenated metabolites in primary human hepatocytes and the reduction in their formation in presence of the specific aldehyde oxidase inhibitor hydralazine. If respective hydralazine-inhibitable metabolites are also formed in human liver cytosol incubations in the absence of any cofactors, involvement of aldehyde oxidase in the metabolism of the respective compound is considered likely.

The involvement of aldehyde oxidase in metabolic transformation of the test compound is investigated using primary human hepatocytes in suspension in presence or absence of the specific aldehyde oxidase inhibitor hydralazine. After recovery from cryopreservation, human hepatocytes are incubated in Dulbecco's modified eagle medium supplemented with 3.5 µg glucagon/500 ml, 2.5 mg insulin/500 ml and 3.75 mg/500 ml hydrocortisone) containing 5% human serum.

Following a 30 min preincubation in a cell culture incubator (37° C., 10% $CO_2$) with or without 50 µM hydralazine, test compound solution is spiked into the hepatocyte suspension to obtain a final cell density of $1.0*10^6$ to $4.0*10^6$ cells/mi (depending on the metabolic turnover rate of the compound observed with primary human hepatocytes), a final test compound concentration of 1 µM, and a final DMSO concentration of 0.05%.

The cells are incubated for six hours (incubator, horizontal shaker) and samples are removed from the incubation after 0, 0.5, 1, 2, 4 or 6 hours, depending on the metabolic turnover rate. Samples are quenched with acetonitrile and pelleted by centrifugation. The supernatant is transferred to a 96-deepwell plate, evaporated under nitrogen and resuspended prior to bioanalysis by liquid chromatography-high resolution mass spectrometry for identification of putative metabolites.

The involvement of aldehyde oxidase in the metabolic transformation of the test compound is confirmed at 37° C. with pooled human liver cytosol fractions. The incubations, conducted at a final incubation volume of 60 µl per time point, are composed of phosphate buffer (100 mM, pH 7.4), magnesium chloride (5 mM), and human liver cytosol (5 mg/ml). Following a short preincubation period at 37° C., the reactions are initiated by addition of the test compound, resulting in a final concentration of 10 µM. After 0 and 60 minutes, the incubations are terminated by transferring an aliquot into organic solvent, followed by centrifugation (10000 g, 5 min). The resulting supernatant is used for bioanalysis by liquid chromatography-high resolution mass spectrometry for identification of putative metabolites.

TABLE 4

Aldehyde oxidase (AO) in vitro metabolite profiling of examples of the present invention.

| Example | % Parent of drug-related material [%] | Main metabolites[1] [% of total oxygenated metabolites] | % Inhibition by 50 µM hydralazine [% untreated control] | Formation in human liver cytosol incubations[2] [yes/no] | Contribution of AO to oxidative metabolism [%] |
|---|---|---|---|---|---|
| 4 | 94 | m418(3): 41 | 22 | yes | 53 |
|   |    | m418(5): 12 | 20 | yes |    |
| 10 | 91 | m430(6): 22 | 20 | yes | 22 |
| 11 | 86 | m446(6): 1  | 31 | yes | 28 |
|    |    | m446(7): 11 | 25 | yes |    |
|    |    | m440(3): 16 | 26 | no[3] |   |
| 12 | 93 | m414(5): 56 | 31 | yes | 56 |
| 13 | 15 | m414(6): 15 | 23 | yes | 15 |
| 14 | 94 | m448(7): 22 | 22 | yes | 22 |
| 15 | 71 | m432(5): 71 | 23 | yes | 71 |
| 21 | 80 | m428(4): 67 | 48 | yes | 67 |
| 29 | 96 | m414(2): 36 | 52 | yes | 36 |

[1]Only metabolites shown that are formed via aldehyde oxidase.
[2]"yes": Metabolite is formed in presence of human liver cytosol in the absence of cofactors as indication of aldehyde oxidase mediated metabolism. "no": Metabolite is not detected in cytosol incubations.
[3]The formation of metabolite "m440(3)" of example 11 is likely to be a two-step mechanism: oxidative defluorination of the CF$_2$H substituent is CYP-mediated and subsequent oxidation is likely mediated via aldehyde oxidase. Therefore, metabolite formation is inhibited in the presence of hydralazine, but the metabolite is not formed in cytosol.

hERG (Human Ether-à-go-go-Related Gene)—Channel Assay hERG Channel inhibition of compounds of the present invention can be investigated as follows:

Cells:

HEK (human embryonic kidney) 293 cells are stably transfected with hERG cDNA. Cells determined for use in patch clamp experiments are cultivated without antibiotic.

Pipettes and Solutions:

Cells are superfused with a bath solution containing (mM): NaCl (137), KCl (4.0), MgCl2 (1.0), CaCl2 (1.8), Glucose (10), HEPES (10), pH 7.4 with NaOH. Patch pipettes are made from borosilicate glass tubing using a pipette and filled with pipette solution containing (mM): K-aspartate (130), MgCl2 (5.0), EGTA (5.0), K2ATP (4.0), HEPES (10.0), pH 7.2 with KOH. Resistance of the microelectrodes is typically in the range between 2 and 5 MΩ.

Stimulation and Recording:

Membrane currents are recorded using an EPC-10 patch clamp amplifier (HEKA Electronics, Lambrecht, FRG) and PatchMaster software (HEKA). hERG-mediated membrane currents are recorded at typically 28° C., using the whole-cell configuration of the patch-clamp technique. Transfected HEK293 cells are clamped at a holding potential of −60 mV and hERG-mediated inactivating tail currents are elicited using a pulse pattern with fixed amplitudes (activation/inactivation: 40 mV for 2000 ms; recovery: 120 mV for 2 ms; ramp to 40 mV in 2 ms; inactivating tail current: 40 mV for 50 ms) repeated at 15 s intervals. During each inter-pulse interval 4 pulses scaled down by a factor of 0.2 are recorded for a P/n leak subtraction procedure. Rs compensation is employed up to a level that safely allows recording devoid of ringing. The remaining uncompensated Rs is recorded as well as actual temperature and holding current.

Compound Preparation and Application:

The concentrations of the test item are applied sequentially on each of the different cells investigated. A steady state level of baseline current is measured for at least 5 sweeps prior to the application of the first test article concentration. The test item is dissolved in DMSO to yield a stock solution of 1000-fold the highest final concentration. This stock is diluted further in DMSO to stock solutions of 1000-fold the remaining final concentrations. Final dilutions in extracellular buffer are prepared freshly from these stocks by a 1:1000 dilution step each before starting the experiments.

Data Analysis:

Peak current amplitudes are measured 3 ms after the ramp to +40 mV. For baseline and each concentration the peak currents of the three last sweeps before application of the next concentration are averaged. Residual currents (¹/₁₀) are calculated for each cell as the fraction of actual average peak current and average baseline peak current. Current inhibition is expressed as (1−¹/₁₀)*100%. Current inhibition for all cells is reported as mean±SD. If possible, from mean current inhibition data the IC50 is estimated based on the Hill equation using a least squares procedure.

In view of their ability to activate GPR52, their low/moderate hERG channel inhibition and more diversified metabolism with subsequently reduced risk for CYP-mediated drug-drug-interactions the compounds of general formula (I) according to the invention, or the physiologically acceptable salts thereof, are suitable for the treatment and/or preventative treatment of all those diseases or conditions which can be influenced by activation of GPR52.

Therefore, compounds according to the invention, including the physiologically acceptable salts thereof, are particularly suitable for the prevention or treatment of diseases, particularly Schizophrenia; Positive symptoms associated with schizophrenia; Augmentation treatment of the positive symptoms associated with schizophrenia; Augmentation of antipsychotics to improve the treatment of the positive symptoms associated with schizophrenia or to lower the dose, and thereby side effects, of antipsychotics; Negative symptoms associated with schizophrenia; Cognitive impairment associated with schizophrenia (CIAS); Treatment resistant schizophrenia; Schizoaffective disorder; Schizophreniform disorder; Schizotypal disorder; Drug-induced psychosis; Bipolar disorder; Attenuated psychosis syndrome and the Neuropsychiatric symptoms associated with Alzheimer's Disease, Parkinsons's Disease, Vascular dementia, and Frontotemporal dementia; Autism spectral disorder (ASD); Impulse control disorder induced by D2 receptor agonists; Gambling Disorder induced by D2 receptor agonists; Tourette's syndrome; cognitive deficits associated with Alzheimer's disease, Parkinson's disease, Vascular dementia, and Frontotemproal dementia; Depression; Attention deficit hyperactivity disorder; Major depressive disorder; Drug addiction; Anxiety; Mania in Bipolar disorder; Acute mania; Agitation; Detachment; and the treatment of symptoms associated with hypofrontality (e.g. Hypofrontality associated with drug abuse) and/or hyperkinetic symptoms. Additionally, compounds according to the invention, are particularly suitable as a co-medication with currently prescribed neuroleptics to treat the positive symptoms associated with schizophrenia, resulting not only in improved anti-psychotic efficacy, but could also be combined with reduced doses of neuroleptic drugs, to lower their associated side effects, such as weight gain, metabolic syndrome, diabetes, extrapyramidal symptoms, hyperprolactinemia, insulin resistance, hyperlipidemia, hyperglycemia and tardive dyskinesia. In particular, increased serum prolactin levels is a prominent side effect profile of neuroleptics, whereas activators of GPR52 have been demonstrated to lower serum prolactin levels, therefore co-application of GPR52 agonists with neuroleptics may normalize serum prolactin levels, thereby lowering the side effects associated with neuroleptics.

Preferably the compounds according to the invention are suitable for the prevention or treatment of Schizophrenia; Positive symptoms associated with schizophrenia; Augmentation treatment of the positive symptoms associated with schizophrenia; Augmentation of antipsychotics to improve the treatment of the positive symptoms associated with schizophrenia or to lower the dose, and thereby side effects, of antipsychotics; Negative symptoms associated with schizophrenia; Cognitive impairment associated with schizophrenia (CIAS); Treatment resistant schizophrenia; Schizoaffective disorder; Schizophreniform disorder; Schizotypal disorder; Drug-induced psychosis; Bipolar disorder; Attenuated psychosis syndrome and the Neuropsychiatric symptoms associated with Alzheimer's Disease, Parkinson's Disease, Vascular dementia, and Frontotemporal dementia; Autism spectral disorder (ASD); Impulse control disorder induced by D2 receptor agonists; and Gambling Disorder induced by D2 receptor agonists.

In a further aspect of the present invention the present invention relates to methods for the treatment or prevention of above mentioned diseases and conditions, which method comprises the administration of an effective amount of a compound of general formula (I), or the pharmaceutically acceptable salts thereof, to a human being.

The dose range of the compounds of general formula (I) applicable per day is usually from 0.1 to 1000 mg, preferably from 1 to 500 mg by oral route, in each case administered 1 to 4 times a day. Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I, including the pharmaceutically acceptable salts thereof, will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine, ketamine, Esketamine, NR2b antagonists); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocydin or rifampicin); PDE2, PDE4, PDE5, PDE9, PDE10 inhibitors, GABAA receptor agonists or positive modulators, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 1 positive modulators, metabotropic glutamate-receptor 2 positive modulators, metabotropic glutamate-receptor 3 positive modulators, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antipsychotics, such as aripiprazole, asenapine, clozapine, iloperidone, haloperidol, olanzapine, paliperidone, quetiapine, risperidone, ziprasidone, lurasidone, lumateperone, brexpiprazole and cariprazine; mood-stabilizers such as lithium and valproate, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or Tau or parts thereof or passive immunisation with humanised anti-Abeta or anti-Tau antibodies or nanobodies) for the treatment of the above-mentioned diseases and conditions.

The dosage for the combination partners mentioned above is usefully ⅕ of the lowest dose normally recommended up to 1/1 of the normally recommended dose.

Therefore, in another aspect, this invention relates to the use of a compound according to the invention or a pharmaceutically acceptable salt thereof combined with at least one of the active substances described above as a combination partner, for preparing a pharmaceutical composition which is suitable for the treatment or prevention of diseases or conditions which can be affected by agonists of GPR52. These are preferably pathologies related to insufficient GPR52 activity, particularly one of the diseases or conditions listed above.

The use of the compound according to the invention in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a pharmaceutically acceptable salt thereof and at least one of the active substances described above as combination partners, optionally together with one or more inert carriers and/or diluents.

The compound according to the invention may both be present together in one formulation, for example a tablet or capsule, or separately in two identical or different formulations, for example as a so-called kit-of-parts.

EXPERIMENTAL SECTION

List of Abbreviations

Bn Benzyl
tBu tert.-Butyl
RT room temperature
ESI-MS electrospray ionisation mass spectrometry
CIP 2-chloro-4,5-dihydro-1,3-dimethyl-1H-imidazolium hexafluorophosphate
aq. aqueous
dppf 1,1'-bis(diphenylphosphanyl)ferrocene
MS mass spectrum
MeOH methanol
EtOH ethanol
EA ethyl acetate
DMA N,N-dimethylacetamide
4-DMAP 4-dimethylamino-pyridine
DMF N,N-dimethylformamide
DMSO dimethylsulfoxide
DCM dichloromethane
T3P 1-propanephosphonic acid anhydride (cyclic trimer)
TCFH chloro-N,N,N',N'-tetramethylformamidinium hexafluorophosphate
THF tetrahydrofuran
DEAD diethyl azodicarboxylate
DIAD diisopropyl azodicarboxylate
DIPEA N,N-diisopropylethylamine
HATU 1-[bis(dimethylamino)methylene]-1H-1,2,3-triazolo[4,5-b]pyridinium 3-oxide hexafluorophosphate
HOBt 1-hydroxybenzotriazole
TBTU O-(benzotriazol-1-yl)-N,N,N',N'-tetramethyl-uronium tetrafluoroborate
Rt retention time
d day(s)
RuPhos 2-dicyclohexylphosphino-2',6'-diisopropoxybiphenyl
h hour(s)
min minutes
sat. saturated
ACN acetonitrile
TFA trifluoroacetic acid
TBAF tetrabutyl ammonium fluoride
M Molarity
MPLC Medium-pressure liquid chromatography
N Normality
$NH_3$ ammonia
NMP N-Methylpyrrolidinone
HPLC high-performance liquid chromatography
HPLC-MS high-performance liquid chromatography-mass spectrometry
LC-MS liquid chromatography mass spectrometry
TLC thin layer chromatography
TEA triethylamine
PPA propylphosphonic acid anhydride, cyclic trimer
HPLC-Methods:
Mobile Phase Preparations:
The mobile phase "$H_2O$ 0.1% TFA" is prepared by adding 1 ml of a commercially available TFA solution to 999 ml water. The mobile phase "$H_2O$ 0.1% $NH_3$" is prepared by adding 4 ml of a commercially available concentrated ammonium hydroxide solution (25 wt %) to 996 ml water.
Method Name: A
Device description: Waters Acquity with DA- and MS-Detector
Column: XBridge, BEH C18, 2.1×30 mm, 2.5 μm
Column Supplier: Waters

| Gradient/Solvent Time [min] | % Sol [H$_2$O, 0.1% NH$_3$] | % Sol [ACN] | Flow [mL/min] | Temp [° C.] |
|---|---|---|---|---|
| 0.0 | 95.0 | 5.0 | 1.3 | 60.0 |
| 0.02 | 95.0 | 5.0 | 1.3 | 60.0 |
| 1.0 | 0.0 | 100.0 | 1.3 | 60.0 |
| 1.1 | 0.0 | 100.0 | 1.3 | 60.0 |

Method Name: B
Device description: Waters Acquity with DA- and MS-Detector
Column: XBridge, BEH C18, 2.1×30 mm, 2.5 urn
Column Supplier: Waters

| Gradient/Solvent Time [min] | % Sol [H$_2$O, 0.1% NH$_3$] | % Sol [ACN] | Flow [mL/min] | Temp [° C.] |
|---|---|---|---|---|
| 0.0 | 95.0 | 5.0 | 1.3 | 60.0 |
| 0.02 | 95.0 | 5.0 | 1.3 | 60.0 |
| 1.0 | 0.0 | 100.0 | 1.3 | 60.0 |
| 1.3 | 0.0 | 100.0 | 1.3 | 60.0 |

Method Name: C
Device description: Waters Acquity with DA- and MS-Detector
Column: BEH C8, 1.7 μm, 2.1×50 mm
Column Supplier: Waters

| Gradient/Solvent Time [min] | % Sol [90% H$_2$O + 10% ACN + NH$_4$CO$_2$H 5 mM] | % Sol [90% ACN + 10% H$_2$O] | Flow [mL/min] | Temp [° C.] |
|---|---|---|---|---|
| 0.0 | 100 | 0 | 0.7 | 35 |
| 1.2 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: D
Device description: Waters Acquity with DA- and MS-Detector
Column: Sunfire, C18, 3.0×30 mm, 2.5 μm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |

Method Name: E
Device description: Waters Acquity with DA- and MS-Detector
Column: CSH C18, 1.7 μm, 2.1×50 mm
Column Supplier: Waters

| Gradient/Solvent Time [min] | % Sol [90% H$_2$O + 10% ACN + HCO$_2$H 0.1%] | % Sol [90% ACN + 10% H$_2$O] | Flow [mL/min] | Temp [° C.] |
|---|---|---|---|---|
| 0.0 | 100 | 0 | 0.7 | 35 |
| 1.2 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

Method Name: F
Device description: ThermoFinnigan HPLC Surveyor DAD, MSQ single quadrupole
Column: Synergi Hydro RP100A, 2.5 μm, 3×50 mm
Column Supplier: Phenomenex

| Gradient/Solvent Time [min] | % Sol [90% H$_2$O + 10% ACN + NH$_4$CO$_2$H 10 mM] | % Sol [90% ACN + 10% H$_2$O + NH$_4$CO$_2$H 10 mM] | Flow [mL/min] | Temp [° C.] |
|---|---|---|---|---|
| 0.0 | 100 | 0 | 1.2 | RT |
| 4.0 | 0 | 100 | 1.2 | RT |
| 5.3 | 0 | 100 | 1.2 | RT |
| 5.5 | 100 | 100 | 1.2 | RT |
| 6.0 | 100 | 100 | 1.2 | RT |

Method Name: G
Device description: Waters Acquity with DA- and MS-Detector
Column: Atlantis T3 3.0 μm, 4.6×50 mm
Column Supplier: Waters

| Gradient/Solvent Time [min] | % Sol [H$_2$O + CF$_3$CO$_2$H 0.1%] | % Sol [ACN] | Flow [mL/min] | Temp [° C.] |
|---|---|---|---|---|
| 0.0 | 98 | 2 | 2.0 | 25 |
| 1.0 | 98 | 2 | 2.0 | 25 |
| 1.5 | 80 | 20 | 2.0 | 25 |
| 2.0 | 80 | 20 | 2.0 | 25 |
| 3.0 | 98 | 2 | 0.1 | 25 |
| 5.0 | 98 | 2 | 0.1 | 25 |

EXAMPLES

The following examples are intended to illustrate the invention, without restricting its scope.

Preparation of Intermediates

Intermediate A-1:

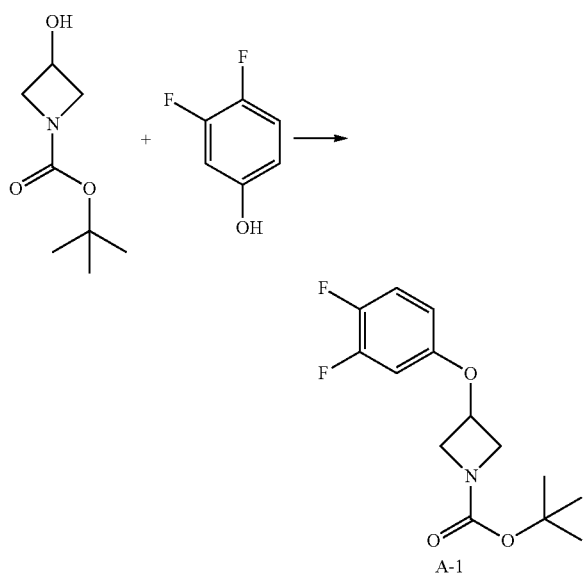

A mixture of 3,4-difluoro-phenol (10.0 g, 76.9 mmol) and cesium carbonate (37.6 g, 115.3 mmol) in DMA (558 mL) is stirred for 5 min at RT, then tert-butyl-3-methanesulfonyloxy)azetidine-1-carboxylate (19.3 g, 76.9 mmol) is added. After stirring at 100° C. for 5 h the mixture is cooled to RT and concentrated under reduced pressure. Water and ethyl acetate are added. Phases are separated. The aqueous phase is extracted 3× with ethyl acetate. The combined organic phases are dried over Na$_2$SO$_4$ and concentrated under reduced pressure. The remainder is purified by MPLC (silica gel, petrol ether/ethyl acetate 9:1) to provide the product A-1.

ESI-MS: 286 [M+H]$^+$; HPLC (Rt): 0.72 min (method A)

Intermediate A-2:

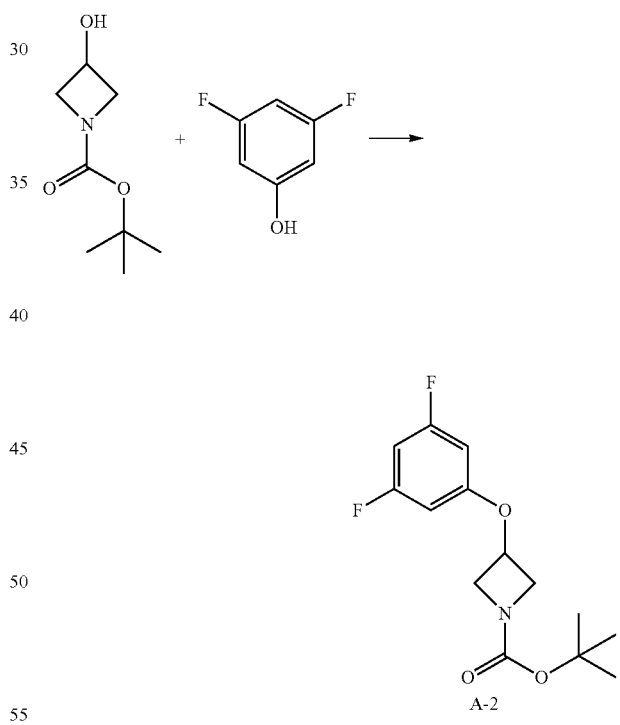

A mixture of 3,5-difluoro-phenol (1.0 g, 8.0 mmol) and cesium carbonate (5.2 g, 15.9 mmol) in DMA (5 mL) is stirred for 10 min at RT, then tert-butyl-3-methanesulfonyloxy)azetidine-1-carboxylate (2.0 g, 8.0 mmol) is added. After stirring at 90° C. for 16 h the mixture is cooled to RT and water and ethyl acetate are added. Phases are separated. The combined organic phases are washed with brine, dried over Na$_2$SO$_4$ and concentrated under reduced pressure. The remainder is purified by preparative HPLC to provide the product A-2.

ESI-MS: 286 [M+H]$^+$; HPLC (Rt): 1.02 min (method D)

Intermediate A-3:

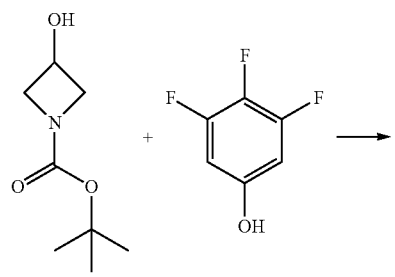

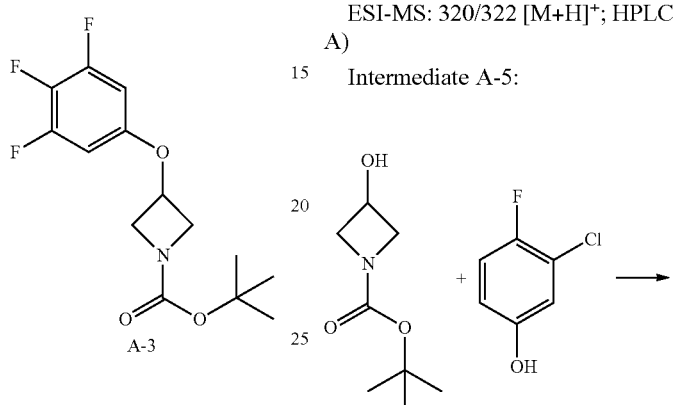

A mixture of 3,4,5-trifluoro-phenol (10.0 g, 64.2 mmol) and cesium carbonate (31.4 g, 96.2 mmol) in DMA (465 mL) is stirred for 10 min at RT, then tert-butyl-3-methane-sulfonyloxy)azetidine-1-carboxylate (16.1 g, 64.2 mmol) is added. After stirring at 100° C. for 6 h the mixture is cooled to RT and concentrated under reduced pressure. Water and ethyl acetate are added. Phases are separated. The aqueous phase is extracted 3× with ethyl acetate. The combined organic phases are dried over Na$_2$SO$_4$ and concentrated under reduced pressure. The remainder is purified by MPLC (silica gel, petrol ether/ethyl acetate 9:1) to provide the product A-3.

ESI-MS: 304 [M+H]$^+$; HPLC (Rt): 0.75 min (method A)

Intermediate A-4:

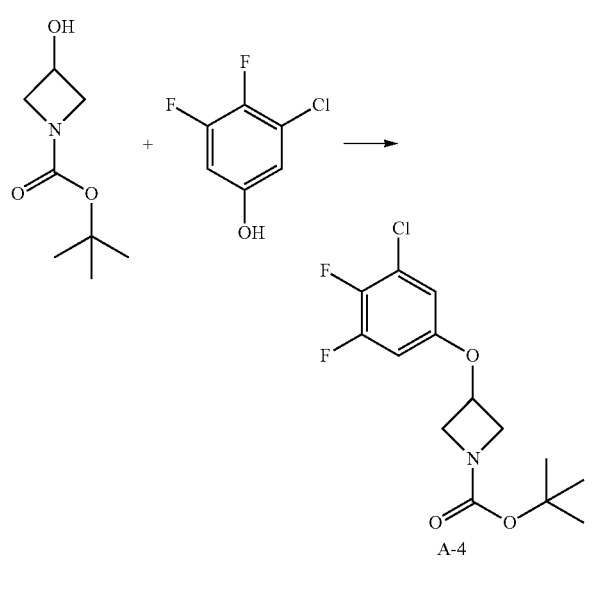

A mixture of 3-chloro-4,5-difluoro-phenol (1.8 g, 10.1 mmol) and cesium carbonate (4.9 g, 15.1 mmol) in DMA (15 mL) is stirred for 10 min at RT, then tert-butyl-3-methane-sulfonyloxy)azetidine-1-carboxylate (2.5 g, 10.1 mmol) is added. After stirring at 90° C. for 16 h the mixture is cooled to RT and water and ethyl acetate are added. Phases are separated and the aqueous phase is extracted 3× with ethyl acetate. The combined organic phases are dried over Na$_2$SO$_4$ and concentrated under reduced pressure. The remainder is purified by preparative HPLC to provide the product A-4.

ESI-MS: 320/322 [M+H]$^+$; HPLC (Rt): 0.79 min (method A)

Intermediate A-5:

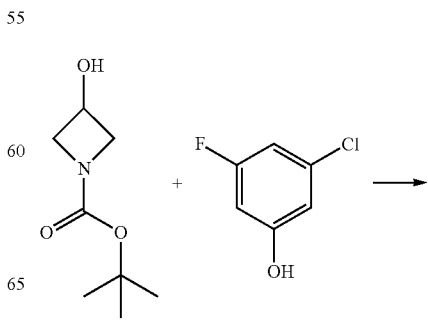

A mixture of 3-chloro-4-fluoro-phenol (1.5 g, 10.2 mmol) and cesium carbonate (6.7 g, 20.5 mmol) in DMA (10 mL) is stirred for 10 min at RT, then tert-butyl-3-methanesulfo-nyloxy)azetidine-1-carboxylate (2.6 g, 10.2 mmol) is added. After stirring at 100° C. for 16 h the mixture is cooled to RT. Water and DCM are added. Phases are separated. The organic phase is dried over Na$_2$SO$_4$ and concentrated under reduced pressure. The remainder is purified by preparative HPLC to provide the product A-5.

ESI-MS: 302/304 [M+H]$^+$; HPLC (Rt): 0.78 min (method A)

Intermediate A-6:

Intermediate A-8:

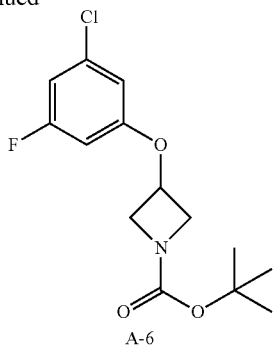

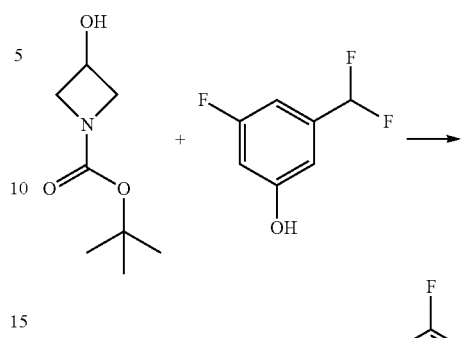

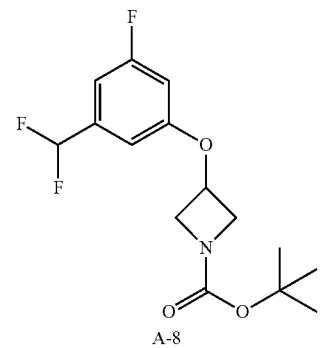

A mixture of 3-chloro-5-fluoro-phenol (4.8 g, 33.0 mmol) and cesium carbonate (21.5 g, 66.1 mmol) in DMF (20 mL) is stirred for 10 min at RT, then tert-butyl-3-methanesulfonyloxy)azetidine-1-carboxylate (2.5 g, 10.1 mmol) is added. After stirring at 90° C. for 16 h the mixture is cooled to RT and water and ethyl acetate are added. Phases are separated and the aqueous phase is extracted 3× with ethyl acetate. The combined organic phases are dried over Na$_2$SO$_4$ and concentrated under reduced pressure. The remainder is purified by preparative HPLC to provide the product A-6.

ESI-MS: 302/304 [M+H]$^+$; HPLC (Rt): 0.77 min (method A)

Intermediate A-7:

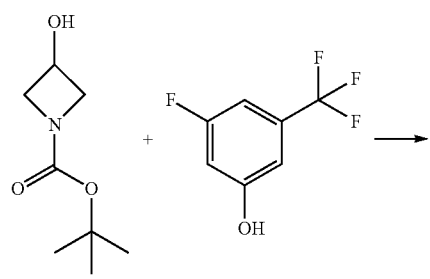

A mixture of 3-fluoro-5-(difluoromethyl)-phenol (2.5 g, 10.0 mmol) and cesium carbonate (6.5 g, 20.0 mmol) in DMA (10 mL) is stirred for 10 min at RT, then tert-butyl-3-methanesulfonyloxy)azetidine-1-carboxylate (2.5 g, 10.0 mmol) is added. After stirring at 90° C. for 16 h the mixture is cooled to RT and water and ethyl acetate are added. Phases are separated. The aqueous phase is extracted 3× with ethyl acetate. The combined organic phases are washed with brine, dried over Na$_2$SO$_4$ and concentrated under reduced pressure. The remainder is purified by preparative HPLC to provide the product A-8.

ESI-MS: 318 [M+H]$^+$, 262 [M+H-isobuten]$^+$; HPLC (Rt): 1.03 min (method D)

Intermediate B-1:

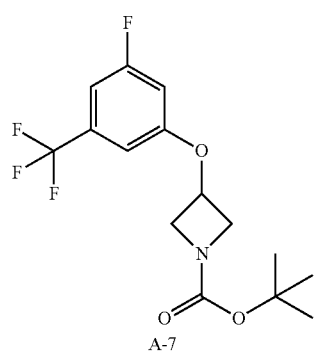

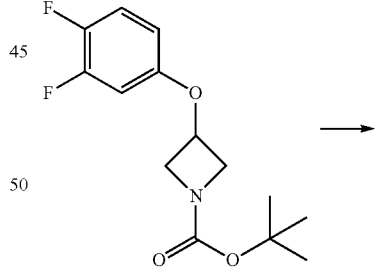

A mixture of 3-fluoro-5-(trifluoromethyl)-phenol (0.7 g, 4.0 mmol), cesium carbonate (2.6 g, 8.0 mmol) and tert-butyl-3-methanesulfonyloxy)azetidine-1-carboxylate (1.0 g, 4.0 mmol) in DMF (30 mL) is stirred for 16 h at 90° C. for 16 h. Then the mixture is cooled to RT and dilute with ethyl acetate. The organic phase is consecutively washed with saturated aqueous solution of NaHCO$_3$, brine and saturated aqueous solution of NH$_4$Cl and is concentrated under reduced pressure to provide the product A-7.

ESI-MS: 336 [M+H]$^+$, 280 [M+H-isobuten]$^+$; HPLC (Rt): 1.44 min (method J)

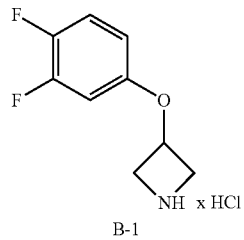

To a mixture of intermediate A-1 (19.0 g, 66.6 mmol) in diisopropylether (200 mL) is added a solution of HCl in dioxane (4N, 83.3 mL, 333.0 mmol). After stirring for 16 h at RT the mixture is concentrated under reduced pressure. The precipitate is washed with diethylether and dried to give product B-1 as HCl salt.

ESI-MS: 186 [M+H]⁺; HPLC (Rt): 0.38 min (method A)

Intermediate B-2:

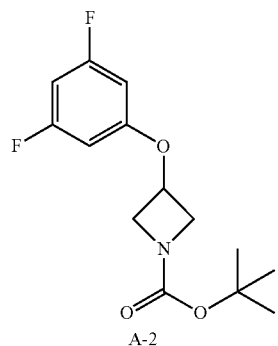

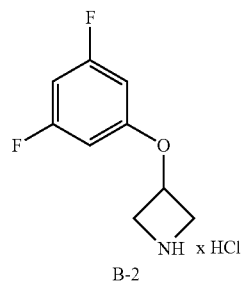

To intermediate A-2 (1.85 g, 6.49 mmol) is added a solution of HCl in dioxane (4N, 15.0 mL, 60.0 mmol). After stirring for 1 h at RT the mixture is concentrated under reduced pressure to give product B-2 as HCl salt.

ESI-MS: 186 [M+H]⁺; HPLC (Rt): 0.38 min (method D)

Intermediate B-3:

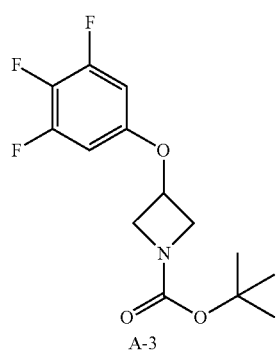

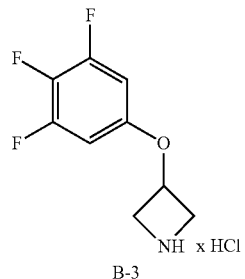

To intermediate A-3 (3.24 g, 10.68 mmol) is added a solution of HCl in dioxane (4N, 25.0 mL, 100.0 mmol). After stirring for 1 h at RT the mixture is concentrated under reduced pressure to give product B-3 as HCl salt.

ESI-MS: 204 [M+H]⁺; HPLC (Rt): 0.45 min (method A)

Intermediate B-4:

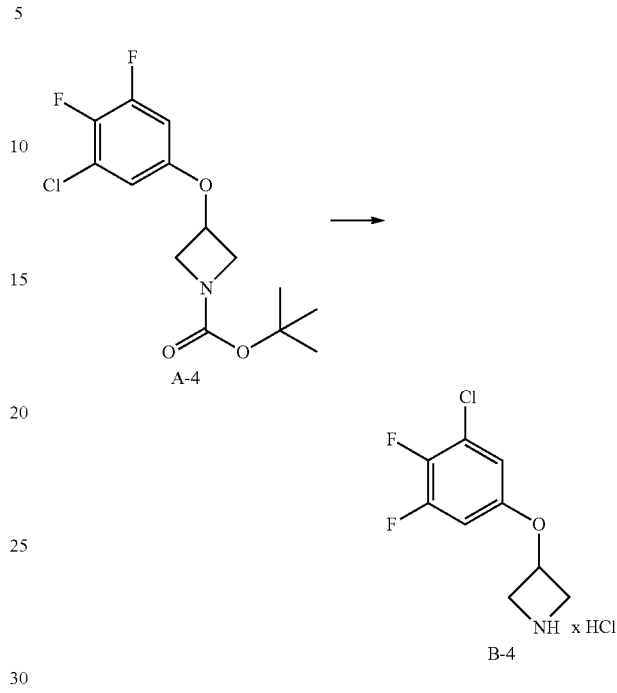

To intermediate A-4 (2.6 g, 8.2 mmol) is added a solution of HCl in dioxane (4N, 20.5 mL, 82.0 mmol). After stirring for 1 h at RT the mixture is concentrated under reduced pressure to give product B-4 as HCl salt.

ESI-MS: 220/222 [M+H]⁺; HPLC (Rt): 0.48 min (method A)

Intermediate B-5:

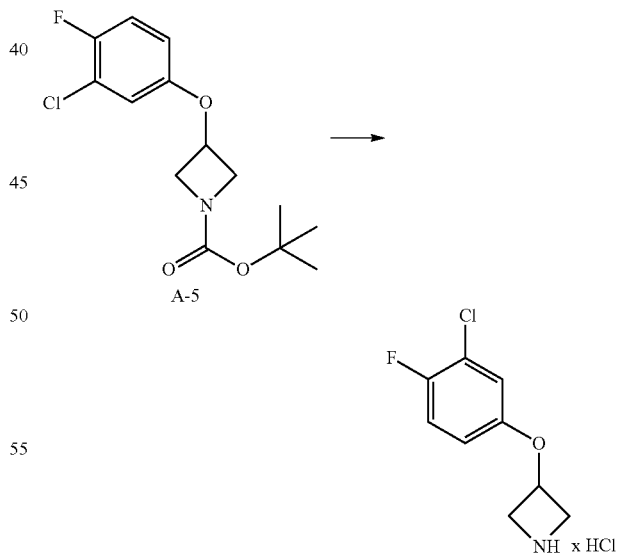

To intermediate A-5 (2.3 g, 7.6 mmol) is added a solution of HCl in dioxane (4N, 9.5 mL, 37.9 mmol). After stirring for 45 min at RT the mixture is concentrated under reduced pressure to give product B-4 as HCl salt.

ESI-MS: 202/204 [M+H]⁺; HPLC (Rt): 0.51 min (method B)

Intermediate B-6:

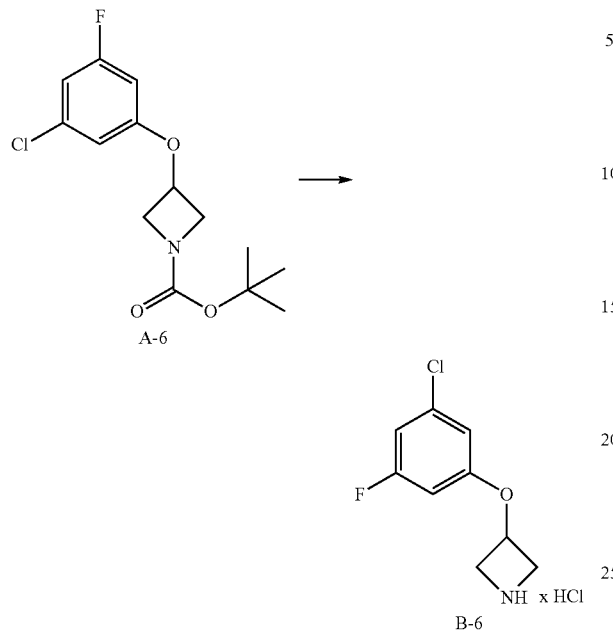

To intermediate A-6 (8.3 g, 27.5 mmol) is added a solution of HCl in dioxane (4N, 34.4 mL, 137.5 mmol). After stirring for 1 h at RT the mixture is concentrated under reduced pressure to give product B-4 as HCl salt.

ESI-MS: 202/204 [M+H]⁺; HPLC (Rt): 0.52 min (method A)

Intermediate B-7:

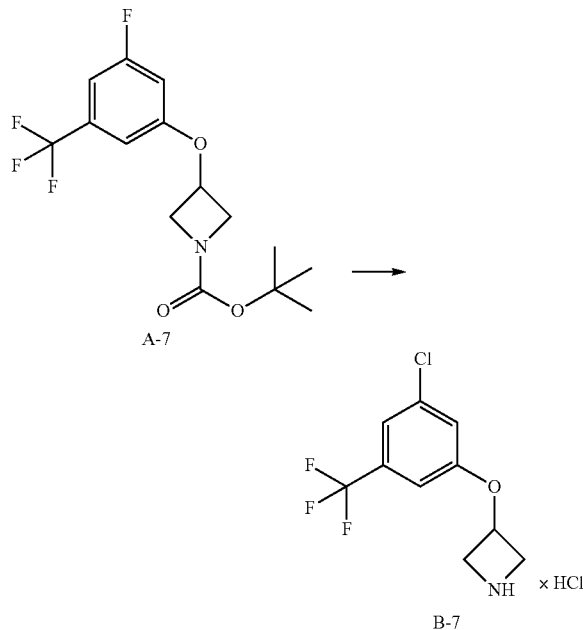

To a mixture of intermediate A-7 (1.3 g, 3.9 mmol) in 1,4-dioxane (20 mL) is added a solution of HCl in dioxane (4N, 6.8 mL, 27.1 mmol). After stirring for 16 h at RT the mixture is concentrated under reduced pressure. The remainder is washed with diethyl ether to give product B-7 as HCl salt.

ESI-MS: 236 [M+H]⁺; HPLC (Rt): 0.63 min (method K)

Intermediate B-8:

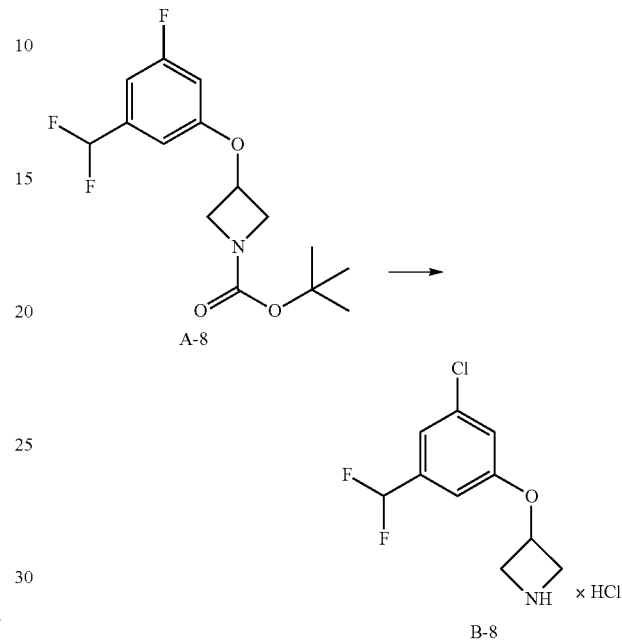

To intermediate A-8 (2.6 g, 8.0 mmol) is added a solution of HCl in dioxane (4N, 12.1 mL, 48.2 mmol). After stirring for 1 h at RT the mixture is concentrated under reduced pressure to give product B-8 as HCl salt.

ESI-MS: 218 [M+H]⁺; HPLC (Rt): 0.45 min (method D)

Intermediate C-1.1:

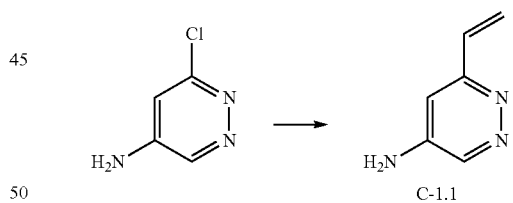

To a mixture of 5-amino-3-chloropyridazine (1.3 g, 10.0 mmol), bis(triphenylphosphine)palladium(II) chloride (1.4 g, 2.0 mmol) and lithium chloride (0.68 g, 16.00 mmol) in DMF (40 mL) under argon atmosphere is added tributyl (vinyl)tin (5.07 g, 16.00 mmol). After stirring at 115° C. for 5 h the reaction mixture is cooled to RT, acidified with TFA and diluted with methanol/acetonitrile (1:1). 3 g thiol polymer is added to scavenge heavy metal content. The mixture is filtered, the polymer beads washed with methanol/acetonitrile (1:1) and the combined filtrate is concentrated under reduced pressure to remove methanol and acetonitrile. The remaining solution containing the crude product is purified by preparative HPLC to give intermediate C-1.1 as HCl salt.

ESI-MS: 122 [M+H]⁺; HPLC (Rt): 1.58 min (method G)

Intermediate C-1:

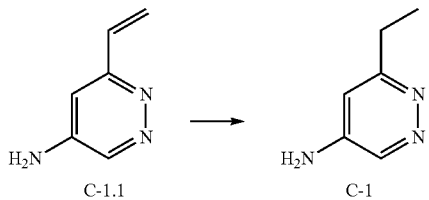

Intermediate C-1.1 (HCl salt, 500.0 mg, 3.2 mmol) is hydrogenated (3 bar hydrogen atmosphere) over palladium on charcoal (10%, 50 mg) in methanol (20 mL) for 3 h at RT. The reaction mixture is filtered and the catalyst is washed with water (20 mL). The combined filtrates are acidified with hydrochloric acid (4N) and concentrated under reduced pressure to provide intermediate C-1 as HCl salt.

ESI-MS: 124 [M+H]$^+$; HPLC (Rt): 1.53 min (method G)

Intermediate D-1:

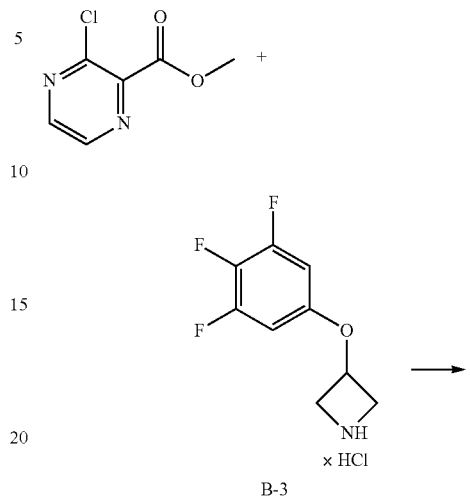

A mixture of methyl 3-fluoropyrazine-2-carboxylate (100.0 mg, 641.0 μmol), intermediate B-7 (208.8 mg, 769.0 μmol) and triethylamine (0.27 mL, 1.9 mmol) in DMA (8 mL) is stirred for 1d at RT. The reaction mixture is diluted with acetonitrile/methanol (1:1 v/v) and purified by preparative HPLC to give intermediate D-1.

ESI-MS: 372 [M+H]$^+$; HPLC (Rt): 0.72 min (method B)

Intermediate D-2:

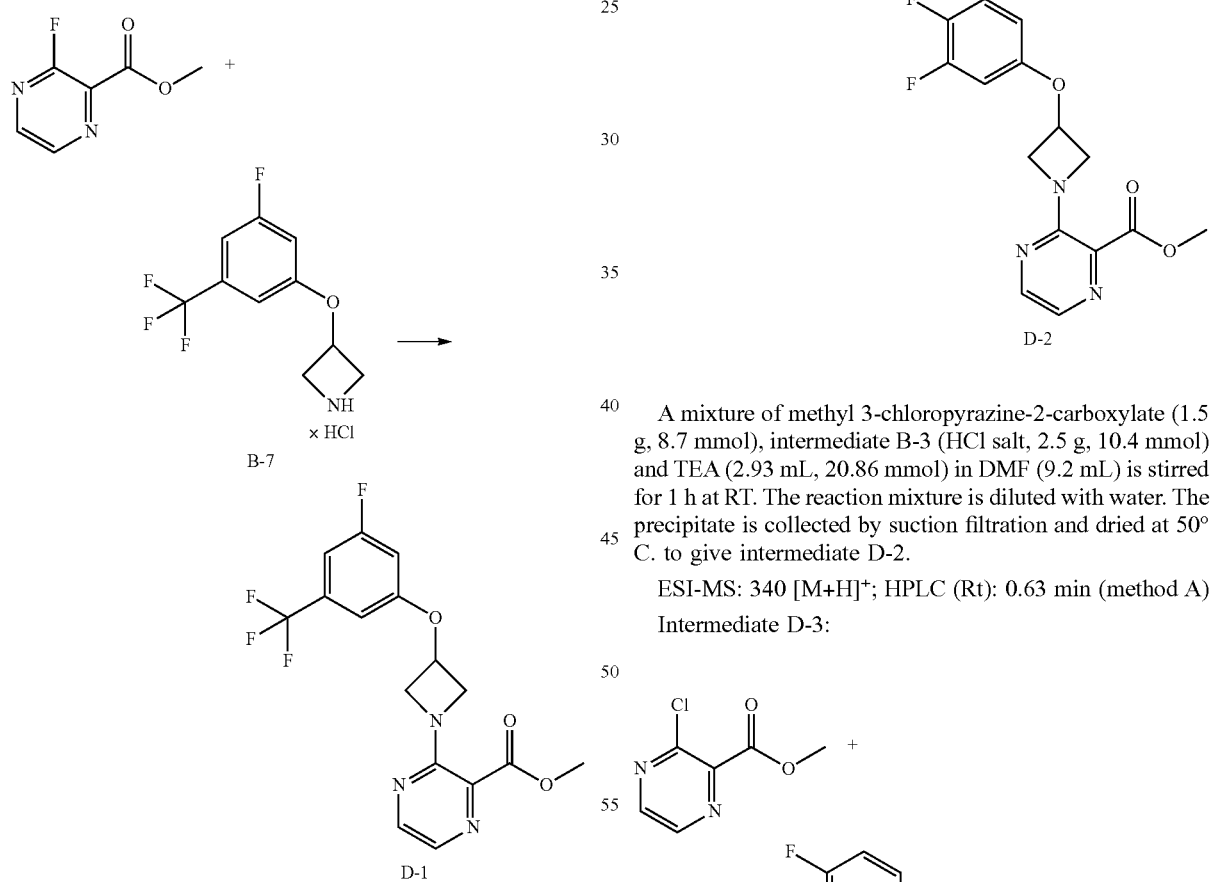

A mixture of methyl 3-chloropyrazine-2-carboxylate (1.5 g, 8.7 mmol), intermediate B-3 (HCl salt, 2.5 g, 10.4 mmol) and TEA (2.93 mL, 20.86 mmol) in DMF (9.2 mL) is stirred for 1 h at RT. The reaction mixture is diluted with water. The precipitate is collected by suction filtration and dried at 50° C. to give intermediate D-2.

ESI-MS: 340 [M+H]$^+$; HPLC (Rt): 0.63 min (method A)

Intermediate D-3:

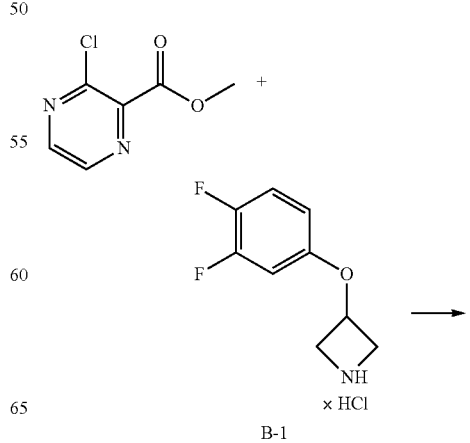

-continued

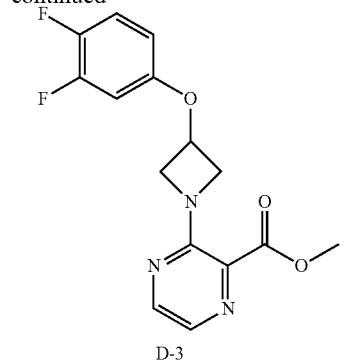

D-3

A mixture of methyl 3-chloropyrazine-2-carboxylate (1.0 g, 5.8 mmol), intermediate B-1 (HCl salt, 1.5 g, 7.0 mmol) and TEA (1.95 mL, 13.91 mmol) in DMA (10 mL) is stirred for 1 h at RT. The reaction mixture is diluted with water. The precipitate is collected by suction filtration and dried at 50° C. to give intermediate D-3.

ESI-MS: 322 [M+H]$^+$; HPLC (Rt): 0.60 min (method A)

Intermediate D-4:

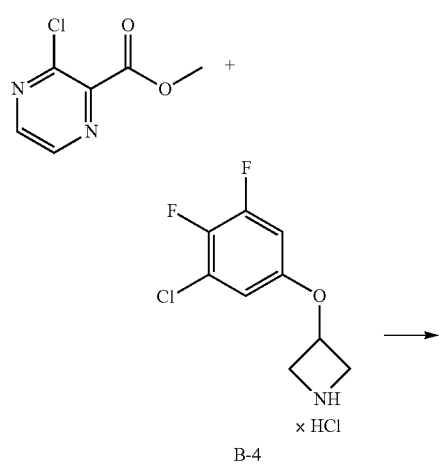

D-4

A mixture of methyl 3-chloropyrazine-2-carboxylate (673.9 mg, 3.9 mmol), intermediate B-4 (1.0 g, 3.9 mmol) and triethylamine (1.6 mL, 11.7 mmol) in DMA (10 mL) is stirred for 2 h at RT. The reaction mixture is diluted with water. The precipitate is collected by suction filtration and is dried to give intermediate D-4.

ESI-MS: 356/358 [M+H]$^+$; HPLC (Rt): 0.68 min (method A)

Intermediate E-1:

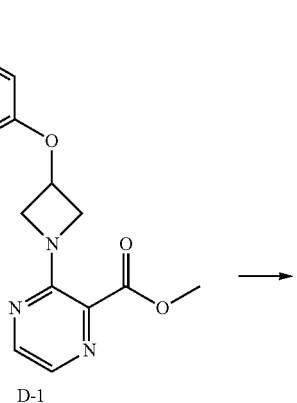

D-1

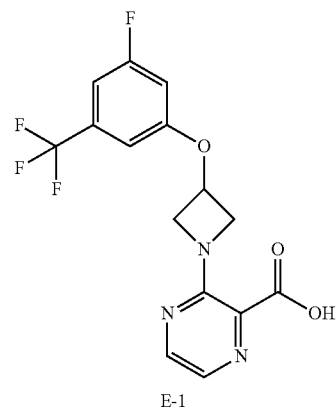

E-1

To a mixture of intermediate D-1 (210.0 mg, 566.0 µmol) in acetone (2 mL) is added an aq. solution of lithium hydroxide (67.7 mg, 2.8 mmol, in 2 mL water). The mixture is stirred for 4 h at RT. Aq. solution of hydrochloric acid (1N) is added dropwise until neutral pH and the mixture is extracted subsequently with ethyl acetate and dichloromethane. The combined organic phases separated from residual water content by passing through a phase separation cartridge and are concentrated under reduced pressure to give intermediate E-1.

ESI-MS: 358 [M+H]$^+$; HPLC (Rt): 0.88 min (method D)

Intermediate E-2:

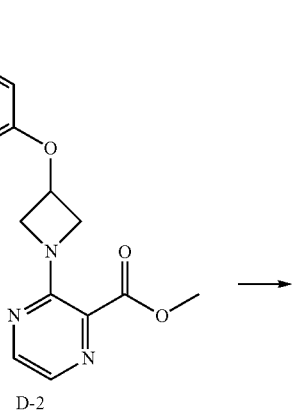

D-2

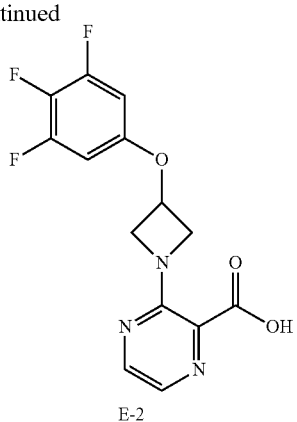

E-2

To a mixture of intermediate D-2 (4.15 g, 12.23 mmol) in acetone (40 mL) is added an aq. solution of lithium hydroxide (585.9 mg, 24.5 mmol, in 40 mL water). The reaction mixture is stirred for 2 h, then diluted with water and is acidified with hydrochloric acid (4N) to pH 4. The precipitate is collected by suction filtration and dried at 50° C. to give intermediate E-2.

ESI-MS: 326 [M+H]$^+$; HPLC (Rt): 0.31 min (method A)

Intermediate E-3:

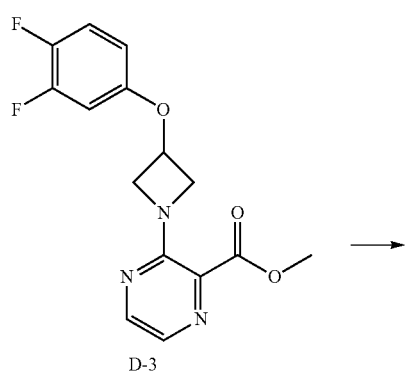

D-3

↓

E-3

To a mixture of intermediate D-3 (1.6 g, 4.9 mmol) in acetone (15 mL) is added an aq. solution of lithium hydroxide (230.0 mg, 9.8 mmol, in 15 mL water). The reaction mixture is stirred for 1.5 h at RT, then diluted with water and is acidified with hydrochloric acid (4N) to pH 4. The precipitate is collected by suction filtration and dried at 50° C. to give intermediate E-3.

ESI-MS: 308 [M+H]$^+$; HPLC (Rt): 0.27 min (method A)

Intermediate E-4:

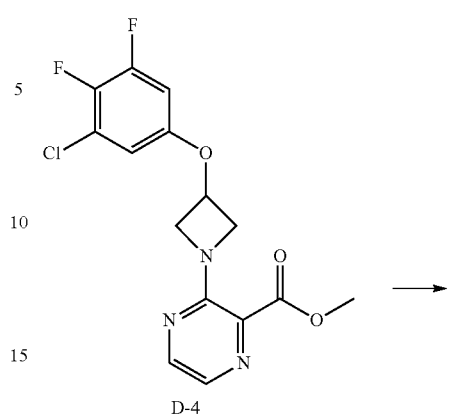

D-4

↓

E-4

To a mixture of intermediate D-4 (1.3 g, 3.6 mmol) in a mixture of THF (5 mL), methanol (2.5 mL) and water (2.5 mL) is added sodium hydroxide (435.2 mg, 10.9 mmol). The mixture is stirred for 18 h at RT and then at 50° C. to complete saponification. After concentration under reduced pressure, water and DCM are added and phases are separated. The aqueous phase is acidified with hydrochloric acid, the formed precipitate is collected and dried to give intermediate E-4.

ESI-MS: 342/344 [M+H]$^+$; HPLC (Rt): 0.32 min (method A)

Intermediate F-1:

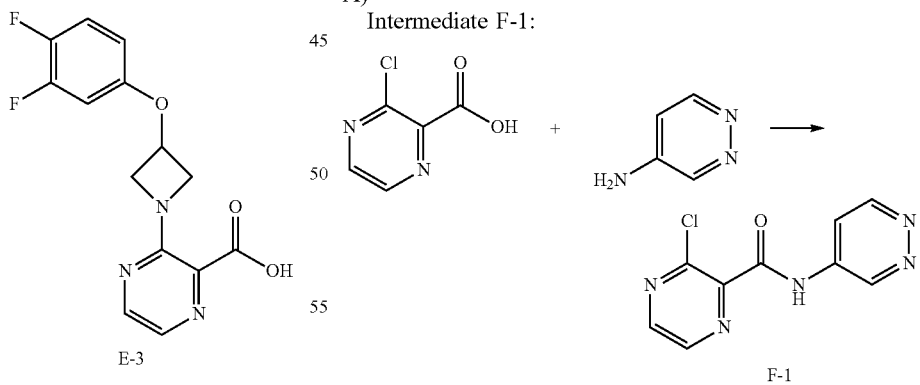

F-1

To a mixture of 3-chloropyrazine-2-carboxylic acid (100.0 mg, 631.0 μmol), 4-aminopyridazine (60.0 mg, 631.0 μmol) and triethylamine (0.44 mL, 3.15 mmol) in DCM (2 mL) is added T3P (50% solution in DMF, 0.41 mL, 694.0 μmol). The mixture is stirred for 30 min at RT and is purified directly by preparative HPLC to give intermediate F-1.

ESI-MS: 236/238 [M+H]$^+$; HPLC (Rt): 0.11 min (method A)

Intermediate F-2:

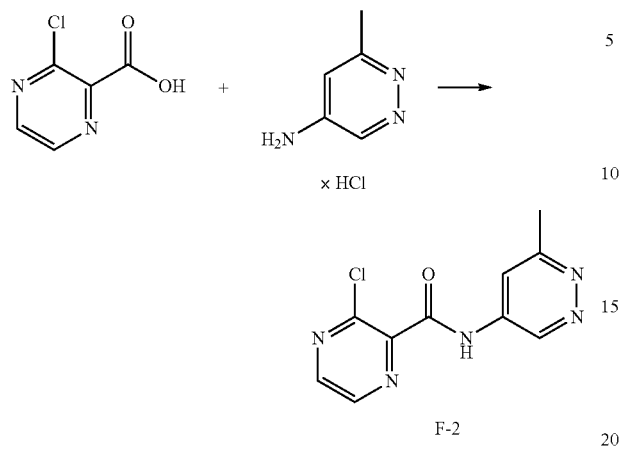

To a mixture of 3-chloropyrazine-2-carboxylic acid (50.0 mg, 315.0 μmol), 4-amino-6-methylpyridazine (HCl salt, 45.9 mg, 315.0 μmol) and triethylamine (0.13 ml, 946.0 μmol) in THF (1 mL) is added T3P (50% solution in ethyl acetate, 0.21 mL, 347.0 μmol). The mixture is stirred for 2 h at RT and is purified directly by preparative HPLC to give intermediate F-2.

ESI-MS: 250/252 [M+H]$^+$; HPLC (Rt): 0.32 min (method D)

Example 1

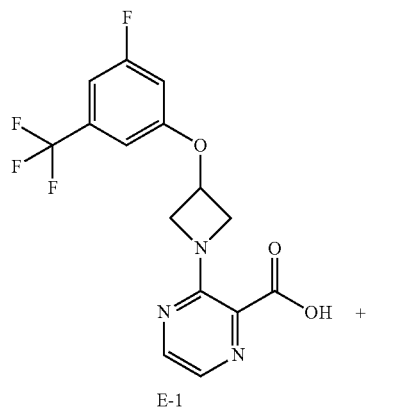

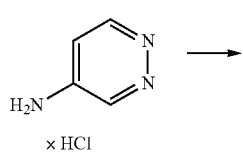

A mixture of intermediate E-1 (90.0 mg, 252.0 μmol), HATU (105.4 mg, 277.0 μmol) and DIPEA (131.0 μL, 756.0 μmol) in DMF (3 ml) is stirred for 5 min at RT. 4-Aminopyridazine (HCl salt, 49.7 mg, 378.0 μmol) is added and the mixture is stirred for 1d and then purified directly by preparative HPLC to provide example 1.

ESI-MS: 435 [M+H]$^+$; HPLC (Rt): 0.63 min (method B)

Example 2

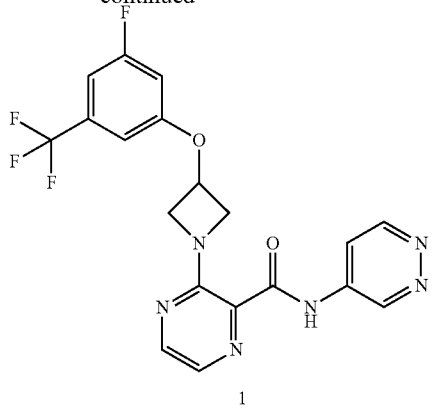

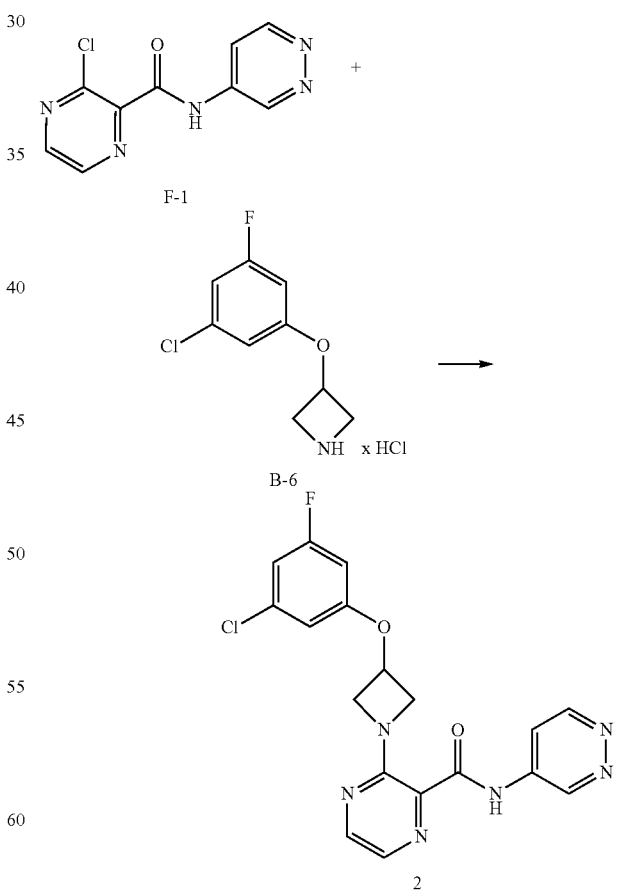

A mixture of intermediate F-1 (60.0 mg, 255.0 μmol), intermediate B-6 (60.6 mg, 255.0 μmol) and triethylamine (106.2 μL, 764.0 μmol) in 2-propanol (2 mL) at 125° C. for 3 h. After cooling to RT the reaction mixture is concentrated under reduced pressure. The remainder is taken up in DCM and washed with an aq. solution of citric acid (10%). After phase separation with a separation cartridge the organic phase is concentrated under reduced pressure to give crude product. The crude is purified by preparative HPLC to provide example 2.

ESI-MS: 401/403 [M+H]⁺; HPLC (Rt): 4.28 min (method F)

Example 3

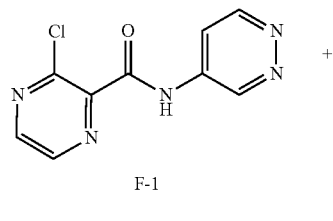

F-1

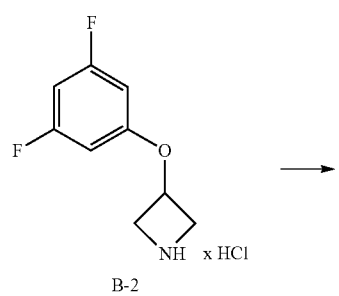

B-2

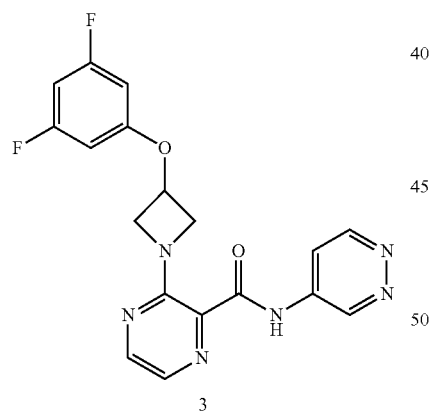

3

A mixture of intermediate F-1 (60.0 mg, 255.0 µmol), intermediate B-2 (56.4 mg, 255.0 µmol) and triethylamine (106.2 µL, 764.0 µmol) in 2-propanol (2 mL) at 125° C. for 3 h. After cooling to RT the reaction mixture is concentrated under reduced pressure. The remainder is taken up in DCM and washed with an aq. solution of citric acid (10%). After phase separation with a separation cartridge the organic phase is concentrated under reduced pressure to give crude product. The crude is purified by preparative HPLC to provide example 3.

ESI-MS: 385 [M+H]⁺; HPLC (Rt): 3.99 min (method F)

Example 4

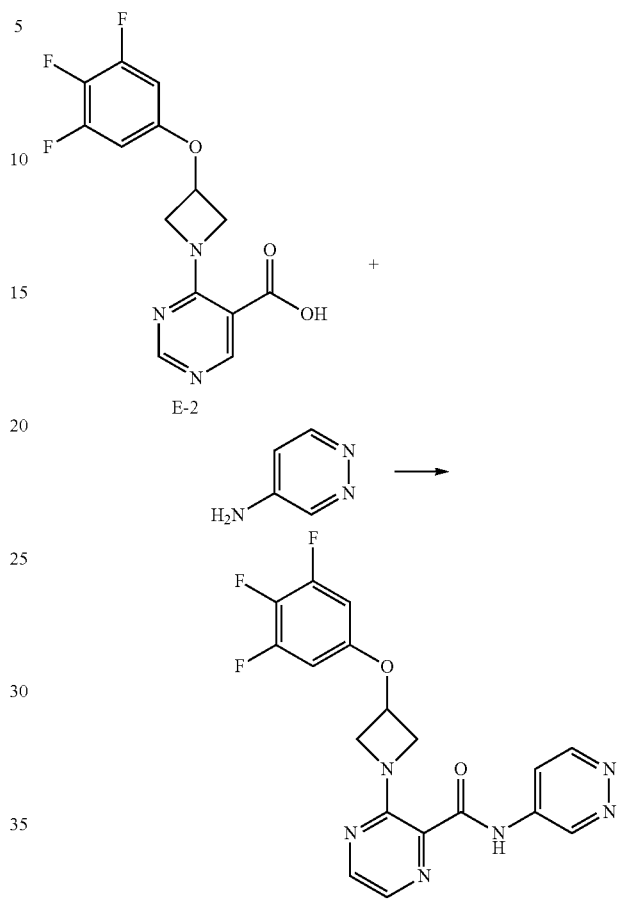

A mixture of intermediate E-2 (1.5 g, 3.0 mmol), HATU (1.2 g, 3.1 mmol) and DIPEA (1.0 mL, 6.0 mmol) in DMA (8 mL) is stirred for 5 min at RT. 4-Aminopyridazine (285.1 mg, 300.0 µmol) is added and the mixture is stirred for 1 d and then purified directly by preparative HPLC to provide example 4.

ESI-MS: 403 [M+H]⁺; HPLC (Rt): 0.60 min (method A)

Example 5

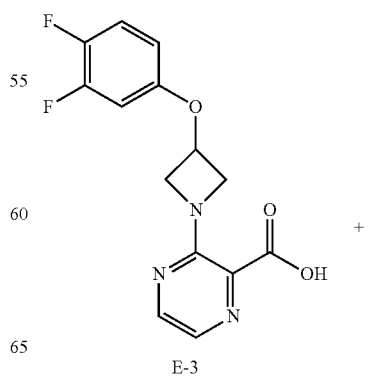

E-3

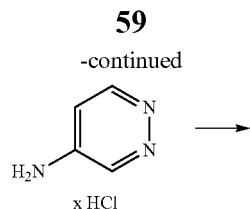

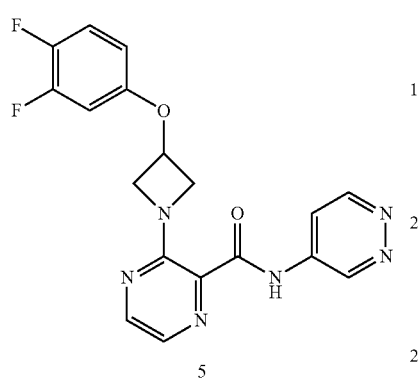

5

A mixture of intermediate E-3 (46.1 mg, 150.0 μmol), HATU (59.9 mg, 158.0 μmol) and DIPEA (51.6 μL, 300.0 μmol) in DMA (2 mL) is stirred for 5 min at RT. 4-Aminopyridazine (HCl salt, 23.7 mg, 180.0 μmol) is added and the mixture is stirred for 1.5 h and then purified directly by preparative HPLC to provide example 5.

ESI-MS: 385 [M+H]⁺; HPLC (Rt): 0.56 min (method A)

Example 6

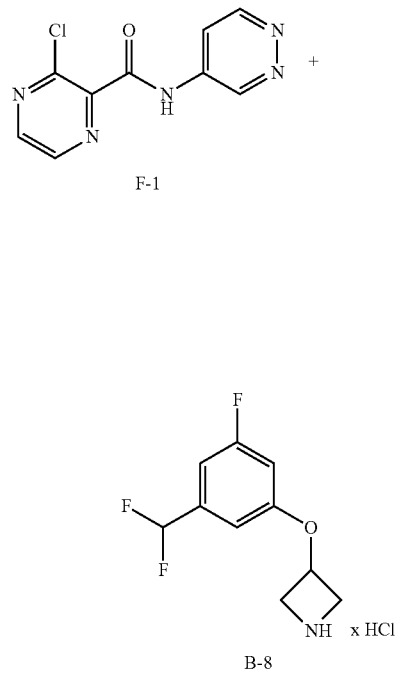

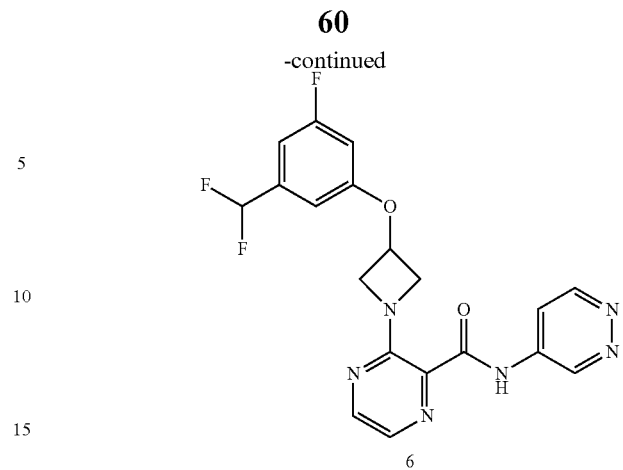

6

A mixture of intermediate F-1 (30.0 mg, 127.0 μmol), intermediate B-8 (32.3 mg, 127.0 μmol) and potassium carbonate (44.0 mg, 318.0 μmol) in toluene (2 mL) and water (1 mL) is stirred at 100° C. for 1 d. After cooling to RT the reaction mixture is taken up in DCM. The organic phase is separated via a separation cartridge and purified by preparative HPLC to give example 6.

ESI-MS: 417 [M+H]⁺; HPLC (Rt): 0.55 min (method B)

Example 7

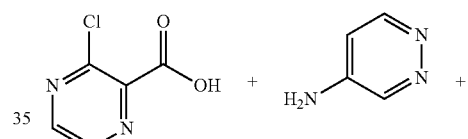

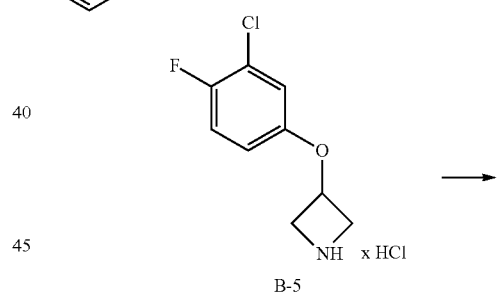

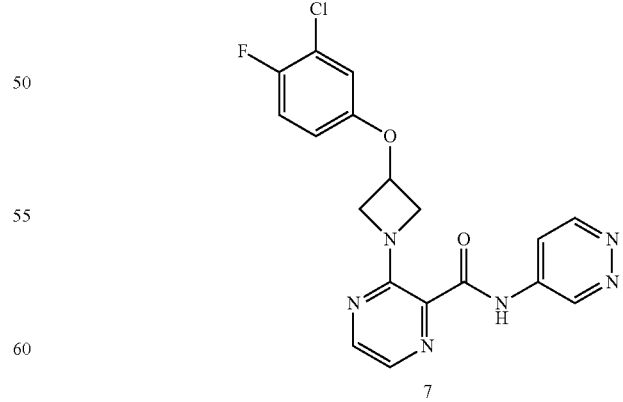

7

To a mixture of 3-chloropyrazine-2-carboxylic acid (50.0 mg, 315.0 μmol) and T3P (50% in ethyl acetate, 0.21 mL, 347.0 μmol) in DMF (1.5 mL) is added TEA (0.13 mL, 946.0 μmol) and 4-aminopyrazine (30.0 mg, 315.0 μmol). After stirring for 5 d at RT, intermediate B-5 (88.8 mg, 347.0 µmol) is added and the reaction mixture is stirred at 100° C. for 4 h. After cooling to RT the reaction mixture is purified directly by preparative HPLC to give example 7.

ESI-MS: 401/403 [M+H]⁺; HPLC (Rt): 0.59 min (method B)

Example 8

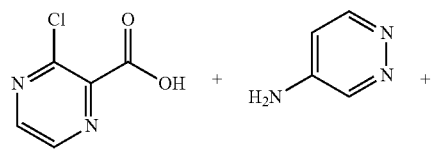

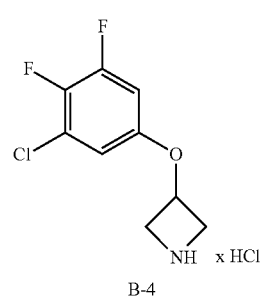

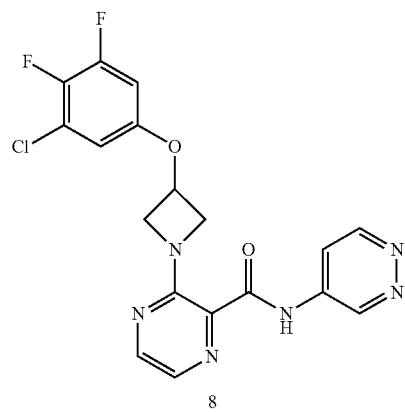

To a mixture of 3-chloropyrazine-2-carboxylic acid (50.0 mg, 315.0 µmol) and T3P (50% in ethyl acetate, 0.21 mL, 347.0 µmol) in THF (2.5 mL) are added TEA (0.13 mL, 946.0 µmol) and 4-aminopyridazine (30.0 mg, 315.0 µmol). After stirring for 1 d at RT, the mixture is filtered and concentrated under reduced pressure. The remainder is taken up in DMF (1.5 mL) and intermediate B-4 (88.8 mg, 347.0 µmol) and TEA (88.6 µL, 631.0 µmol) are added. The reaction mixture is stirred at RT for 3 h. After cooling to RT the reaction mixture is filtered and purified directly by preparative HPLC to give example 8.

ESI-MS: 417/419 [M+H]⁺; HPLC (Rt): 0.62 min (method B)

Example 9

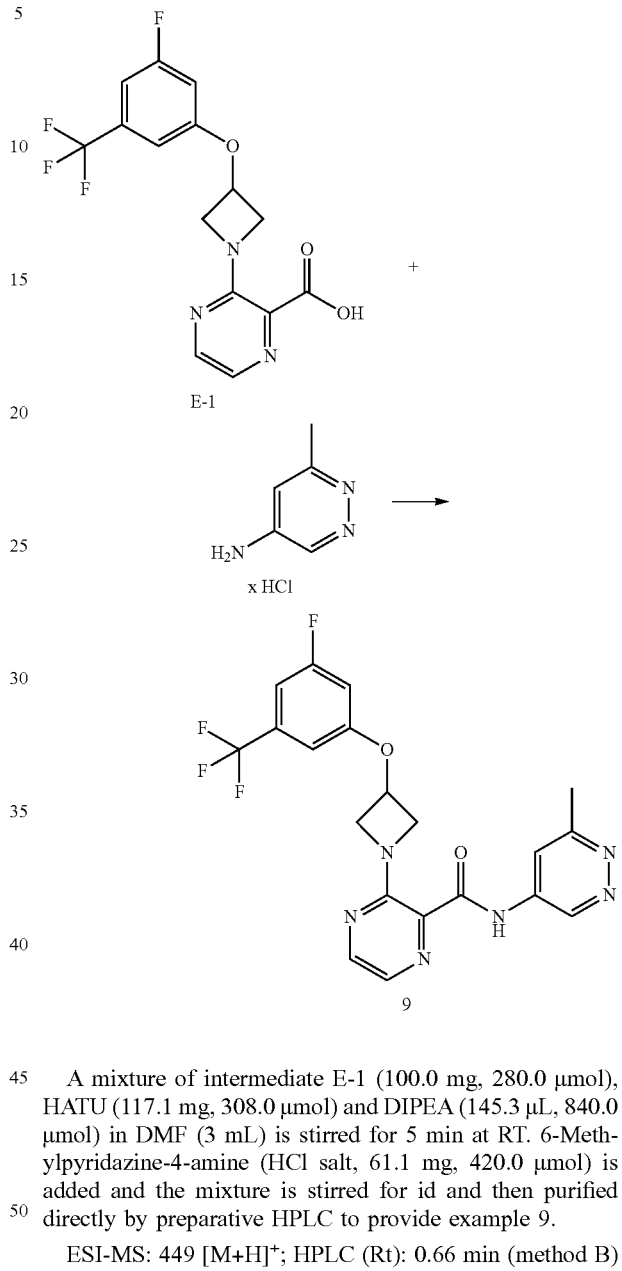

A mixture of intermediate E-1 (100.0 mg, 280.0 µmol), HATU (117.1 mg, 308.0 µmol) and DIPEA (145.3 µL, 840.0 µmol) in DMF (3 mL) is stirred for 5 min at RT. 6-Methylpyridazine-4-amine (HCl salt, 61.1 mg, 420.0 µmol) is added and the mixture is stirred for id and then purified directly by preparative HPLC to provide example 9.

ESI-MS: 449 [M+H]⁺; HPLC (Rt): 0.66 min (method B)

Example 10

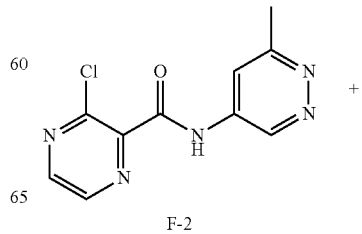

-continued

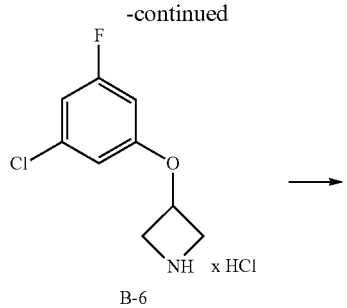

B-6

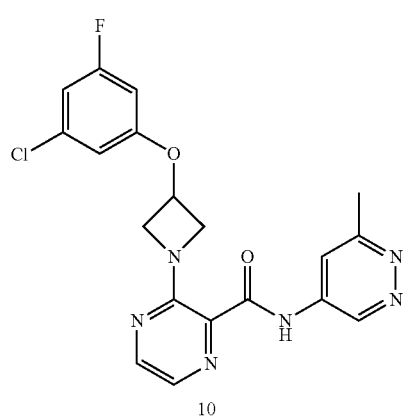

10

To a mixture of intermediate F-2 (50.0 mg, 65% purity, 130.0 μmol), intermediate B-6 (31.0 mg, 130.0 μmol) and potassium carbonate (45.0 mg, 325.0 μmol) in toluene (2 mL) is added water (1 mL). The reaction mixture is stirred at 100° C. for 16 h. After cooling to RT the formed precipitate is filtered off, washed with water and dried at 50° C. to provide example 10.

ESI-MS: 415/417 [M+H]⁺; HPLC (Rt): 0.64 min (method B)

Example 11

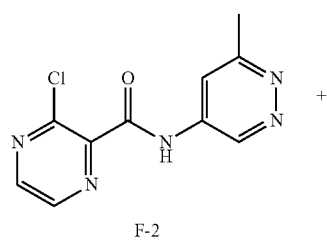

F-2

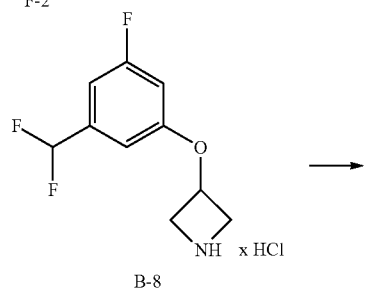

B-8

-continued

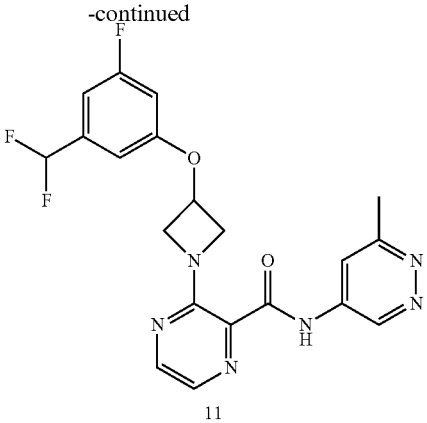

11

To a mixture of intermediate F-2 (30.0 mg, 120.0 μmol), intermediate B-8 (30.5 mg, 120.0 μmol) and potassium carbonate (41.5 mg, 300.0 μmol) in toluene (2 mL) is added water (1 mL). The reaction mixture is stirred at 100° C. for 16 h. After cooling to RT the reaction mixture is concentrated under reduced pressure. The remainder is taken up in DCM. The organic phase is separated via a separation cartridge and is concentrated under reduced pressure. The remainder is purified by preparative HPLC to give example 11.

ESI-MS: 431 [M+H]⁺; HPLC (Rt): 0.59 min (method B)

Example 12

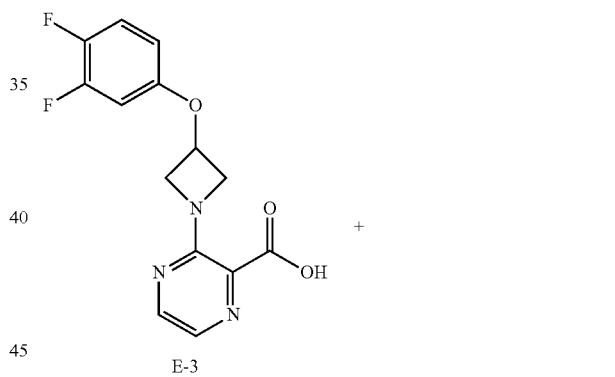

A mixture of intermediate E-3 (60.0 mg, 195.0 μmol), HATU (78.0 mg, 205.0 μmol) and DIPEA (67.2 μL, 391.0 μmol) in DMA (1 mL) is stirred for 10 min at RT. 4-Amino-6-methyl-pyridazine (21.3 mg, 195.0 μmol) is added and the mixture is stirred for 16 h and then purified directly by preparative HPLC to provide example 12.

ESI-MS: 399 [M+H]⁺; HPLC (Rt): 0.49 min (method A)

Example 13

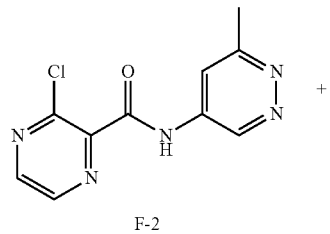

F-2

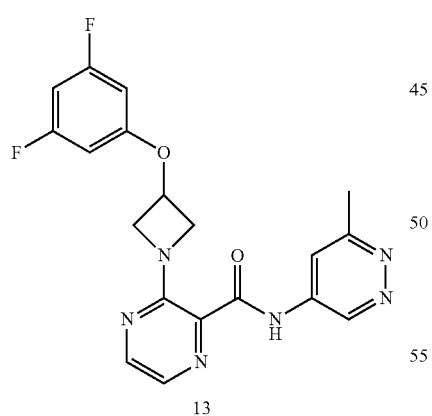

13

To a mixture of intermediate F-2 (170.0 mg, 647.0 μmol), intermediate B-2 (143.4 mg, 647.0 μmol) and potassium carbonate (223.5 mg, 1.6 mmol) in toluene (10 mL) is added water (5 mL). The reaction mixture is stirred at 100° C. for 16 h. After cooling to RT the formed precipitate is filtered off, washed with water and dried at SOT to provide example 13.

ESI-MS: 399 [M+H]⁺; HPLC (Rt): 0.58 min (method B)

Example 14

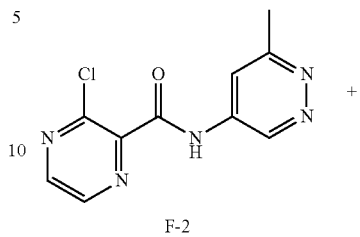

F-2

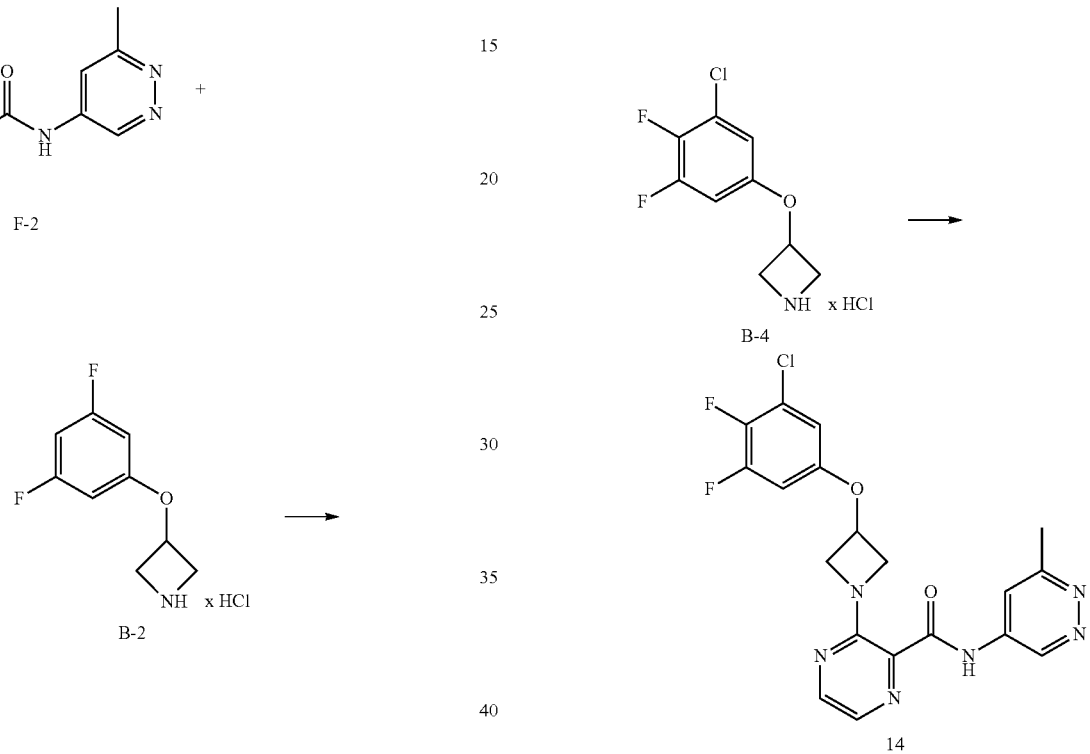

14

A mixture of intermediate F-2 (65.0 mg, 260.0 μmol), intermediate B-4 (80.0 mg, 312.0 μmol) and TEA (73.1 μL, 521.0 μmol) in DMA (1.5 mL) is stirred at 100° C. for 1.5 h. After cooling to RT the reaction mixture is filtered and purified directly by preparative HPLC to provide example 14.

ESI-MS: 433/435 [M+H]⁺; HPLC (Rt): 0.65 min (method B)

Example 15

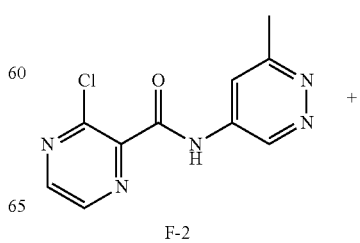

F-2

-continued

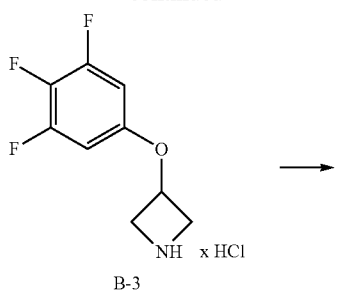
B-3

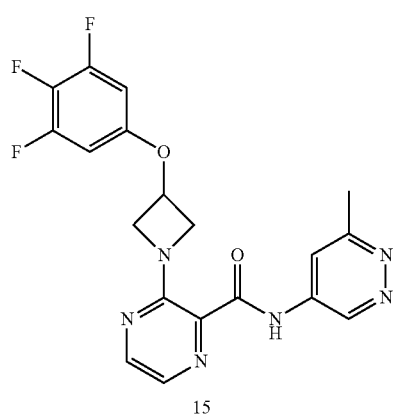
15

To a mixture of intermediate F-2 (78.0 mg, 312.0 µmol), intermediate B-3 (74.9 mg, 312.0 µmol) and potassium carbonate (108.0 mg, 781.0 µmol) in toluene (5 mL) is added water (2.5 mL). The reaction mixture is stirred at 100° C. for 3 h. After cooling to RT the formed precipitate is filtered off, washed with water and dried at 50° C. to provide example 15.

ESI-MS: 417 [M+H]+; HPLC (Rt): 0.61 min (method B)

Example 16

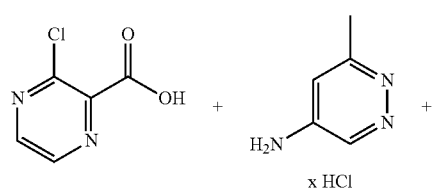

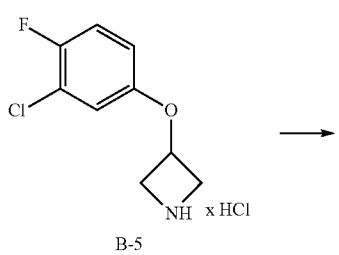
B-5

-continued

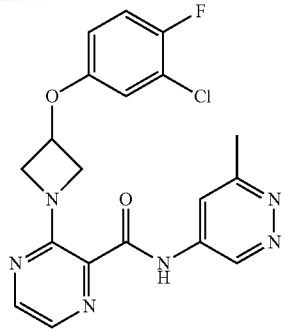
16

To a mixture of 3-chloropyrazine-2-carboxylic acid (50.0 mg, 315.0 µmol) and T3P (50% in ethyl acetate, 0.21 mL, 347.0 µmol) in THF (2.5 mL) are added TEA (0.13 mL, 946.0 µmol) and 4-amino-6-methylpyridazine (HCl salt, 88.8 mg, 347.0 µmol). DMF (2 mL) is added. After stirring for 5 d at RT, intermediate B-5 (88.8 mg, 347.0 µmol) is added. The reaction mixture is stirred at 100° C. for 4 h. After cooling to RT the reaction mixture is filtered and purified directly by preparative HPLC to give example 16.

ESI-MS: 417/419 [M+H]+; HPLC (Rt): 0.62 min (method B)

Example 17

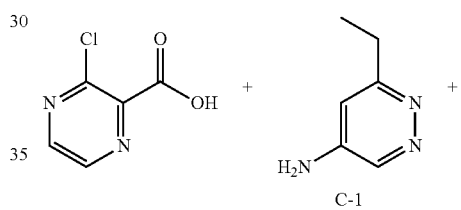
C-1

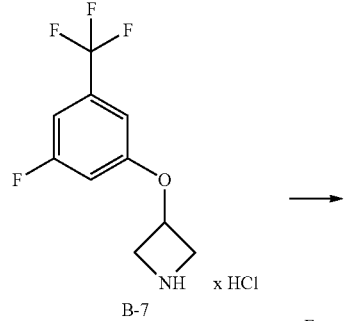
B-7

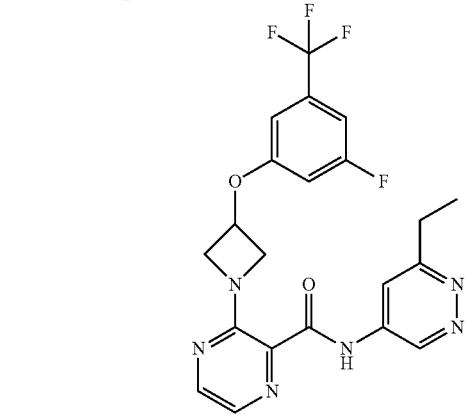
17

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-7 (51.6 mg, 190.0 μmol) and additional DIPEA (100.0 μL, 581.0 μmol) are added to the reaction mixture. After stirring for 45 min at 80° C. the mixture is cooled to RT and purified directly by preparative HPLC to provide example 17.

ESI-MS: 463 [M+H]$^+$; HPLC (Rt): 0.70 min (method B)

Example 18

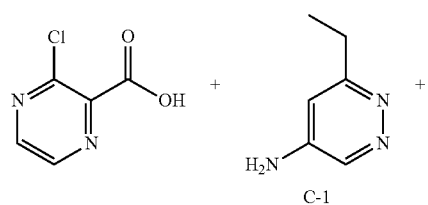

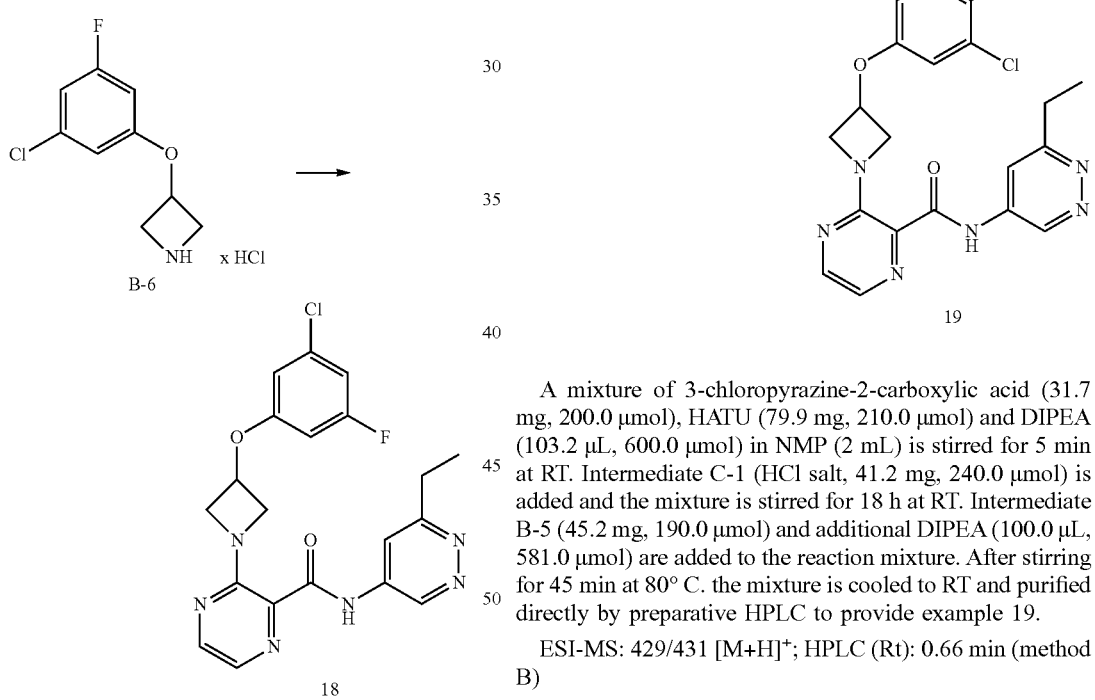

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-6 (45.2 mg, 190.0 μmol) and additional DIPEA (100.0 μL, 581.0 μmol) are added to the reaction mixture. After stirring for 45 min at 80° C. the mixture is cooled to RT and purified directly by preparative HPLC to provide example 18.

ESI-MS: 429/431 [M+H]$^+$; HPLC (Rt): 0.68 min (method B)

Example 19

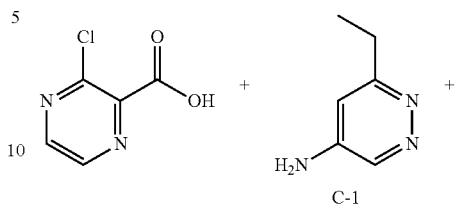

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-5 (45.2 mg, 190.0 μmol) and additional DIPEA (100.0 μL, 581.0 μmol) are added to the reaction mixture. After stirring for 45 min at 80° C. the mixture is cooled to RT and purified directly by preparative HPLC to provide example 19.

ESI-MS: 429/431 [M+H]$^+$; HPLC (Rt): 0.66 min (method B)

Example 20

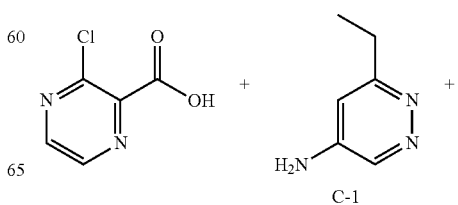

-continued

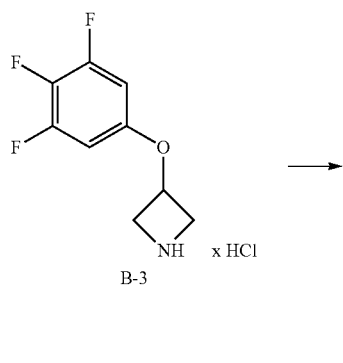

B-3

-continued

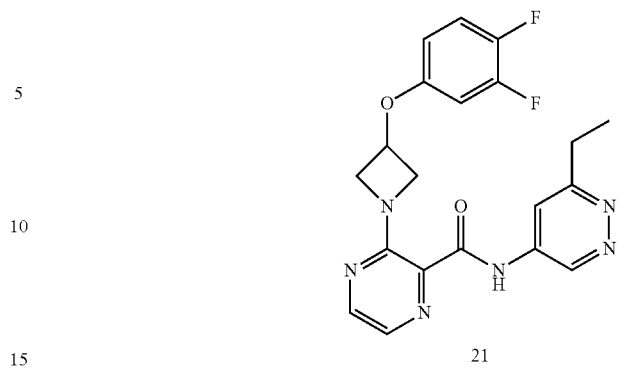

21

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-5 (42.1 mg, 190.0 μmol) and additional DIPEA (100.0 μL, 581.0 μmol) are added to the reaction mixture. After stirring for 45 min at 80° C. the mixture is cooled to RT and poured into water. The precipitate is collected, then taken up in DCM and washed with sat. aq. NaHCO$_3$ solution and brine. The organic phase is mixed with charcoal, filtered through a phase separation cartridge and is concentrated under reduced pressure to give crude product. The crude is purified by preparative HPLC to provide example 21.

ESI-MS: 413 [M+H]$^+$; HPLC (Rt): 0.61 min (method B)

Example 22

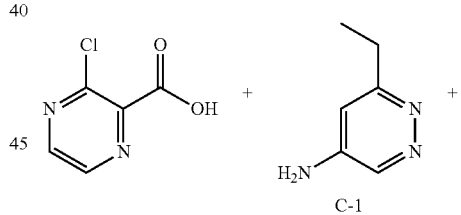

C-1

20

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-3 (47.9 mg, 190.0 μmol) and additional DIPEA (100.0 μL, 581.0 μmol) are added to the reaction mixture. After stirring for 45 min at 80° C. the mixture is cooled to RT and purified directly by preparative HPLC to provide example 20.

ESI-MS: 431 [M+H]$^+$; HPLC (Rt): 0.65 min (method B)

Example 21

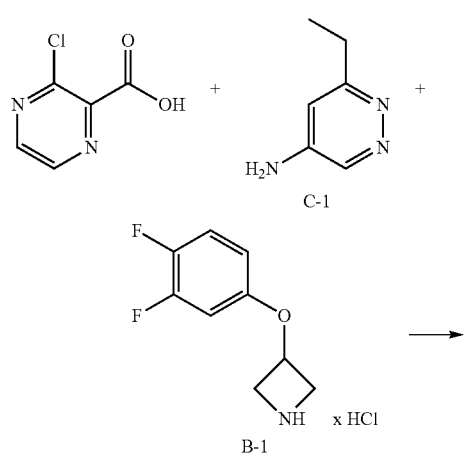

B-8

-continued

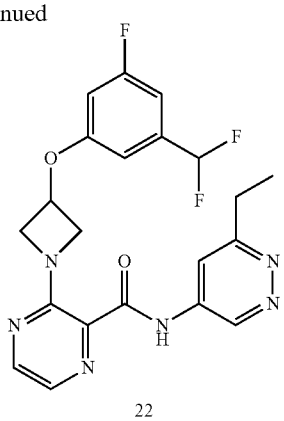

22

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-8 (48.2 mg, 190.0 μmol) and additional DIPEA (100.0 μL, 581.0 μmol) are added to the reaction mixture. After stirring for 45 min at 80° C. the mixture is cooled to RT and purified directly by preparative HPLC to provide example 22.

ESI-MS: 445 [M+H]⁺; HPLC (Rt): 0.63 min (method B)

Example 23

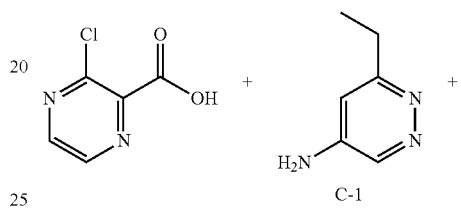

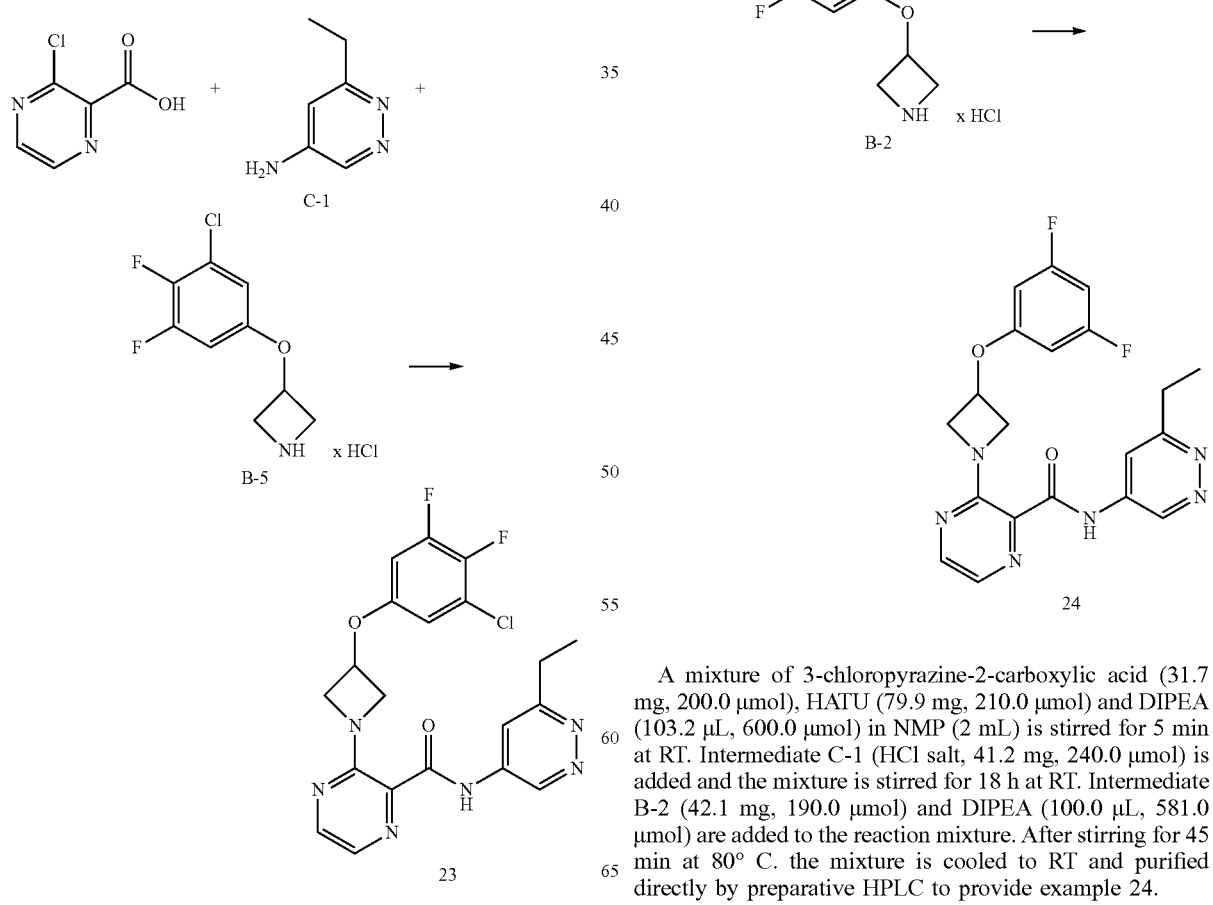

23

A mixture of 3-chloropyrazine-2-carboxylicacid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-4 (48.7 mg, 190.0 μmol) and additional DIPEA (100.0 μL, 581.0 μmol) are added to the reaction mixture. After stirring for 45 min at 80° C. the mixture is cooled to RT and purified directly by preparative HPLC to provide example 23.

ESI-MS: 447/449 [M+H]⁺; HPLC (Rt): 0.69 min (method B)

Example 24

A mixture of 3-chloropyrazine-2-carboxylic acid (31.7 mg, 200.0 μmol), HATU (79.9 mg, 210.0 μmol) and DIPEA (103.2 μL, 600.0 μmol) in NMP (2 mL) is stirred for 5 min at RT. Intermediate C-1 (HCl salt, 41.2 mg, 240.0 μmol) is added and the mixture is stirred for 18 h at RT. Intermediate B-2 (42.1 mg, 190.0 μmol) and DIPEA (100.0 μL, 581.0 μmol) are added to the reaction mixture. After stirring for 45 min at 80° C. the mixture is cooled to RT and purified directly by preparative HPLC to provide example 24.

ESI-MS: 413 [M+H]⁺; HPLC (Rt): 0.63 min (method B)

Example 25

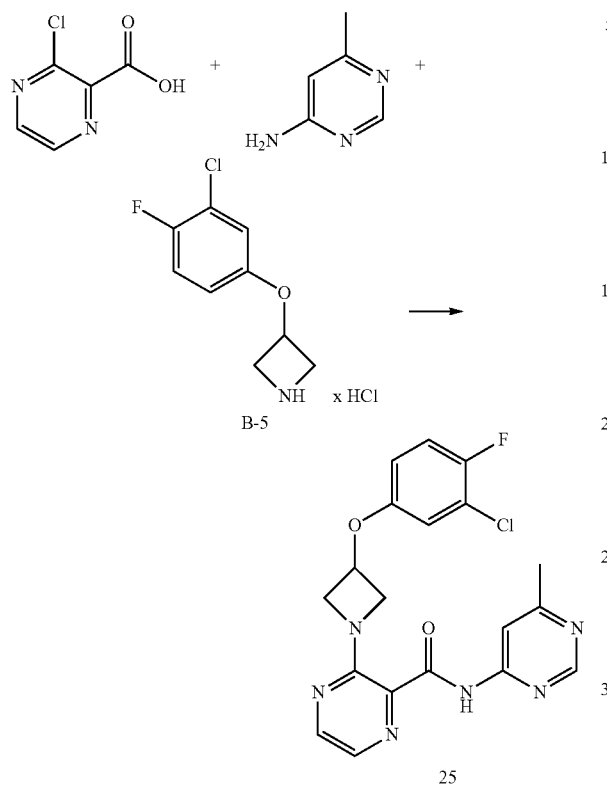

A mixture of 3-chloropyrazine-2-carboxylic acid (31.7 mg, 200.0 μmol), 1-methylimidazole (40.3 μL, 500.0 μmol) and chloro-N,N,N',N'-tetramethylformamidinium hexafluorophosphate (70.1 mg, 250.0 μmol) in NMP (1 mL) is stirred for 10 min at RT. 4-Amino-6-methylpyrimidine (22.9 mg, 210.0 μmol) is added and the mixture is stirred for 18 h at RT. Intermediate B-5 (45.2 mg, 190.0 μmol) and DIPEA (100.0 μL, 581.0 μmol) are added to the reaction mixture. After stirring for 3.5 h at 100° C. the mixture is cooled to RT. Stirring is continued at RT for 20 h, and the mixture purified directly by preparative HPLC to provide example 25.

ESI-MS: 415/417 [M+H]$^+$; HPLC (Rt): 0.72 min (method B)

Example 26

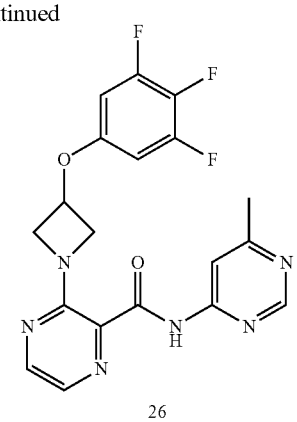

A mixture of intermediate E-2 (100.0 mg, 307.0 μmol), 1-methylimidazole (97.7 μL, 1230.0 μmol) and chloro-N,N,N',N'-tetramethylformamidinium hexafluorophosphate (103.5 mg, 369.0 μmol) and 4-amino-6-methylpyrimidine (36.9 mg, 338.0 μmol) in acetonitrile (2 mL) is stirred for 1 d at RT. The reaction mixture is diluted with a mixture of acetonitrile/methanol (v/v 1:1) and purified directly by preparative HPLC to provide example 26.

ESI-MS: 417 [M+H]$^+$; HPLC (Rt): 0.71 min (method B)

Example 27

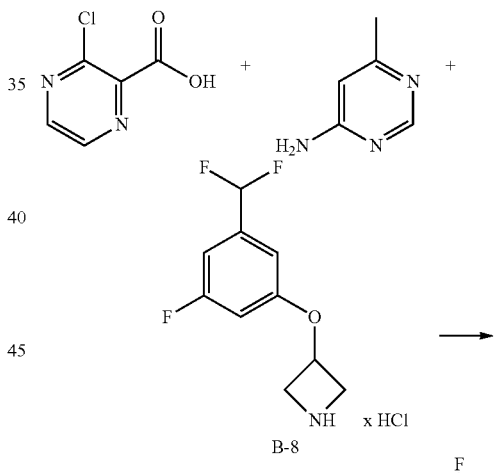

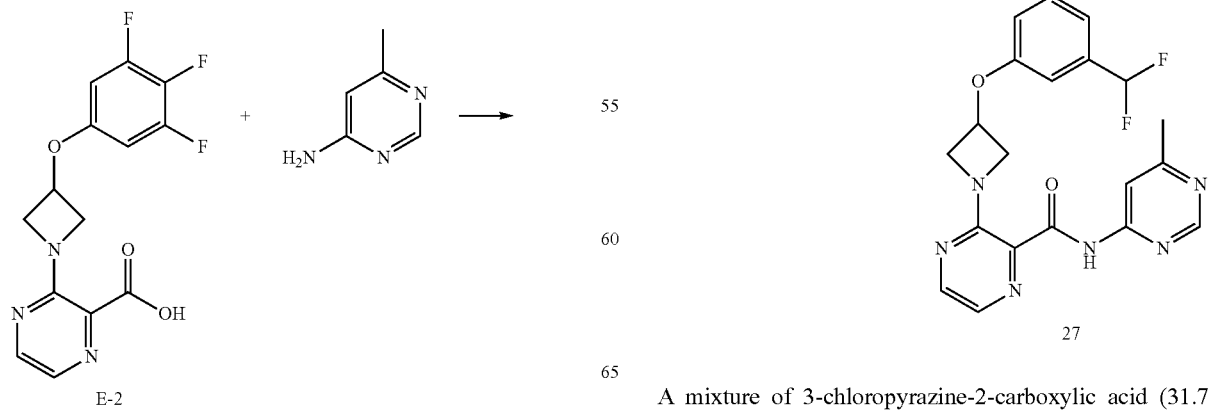

A mixture of 3-chloropyrazine-2-carboxylic acid (31.7 mg, 200.0 μmol), 1-methylimidazole (40.3 μL, 500.0 μmol)

and chloro-N,N,N',N'-tetramethylformamidinium hexafluorophosphate (70.1 mg, 250.0 µmol) in NMP (1 mL) is stirred for 10 min at RT. 4-Amino-6-methylpyrimidine (22.9 mg, 210.0 µmol) is added and the mixture is stirred for 18 h at RT. Intermediate B-8 (48.2 mg, 190.0 µmol) and DIPEA (100.0 µL, 581.0 µmol) are added to the reaction mixture. After stirring for 3.5 h at 100° C. the mixture is cooled to RT. Stirring is continued at RT for 20 h, and the mixture purified directly by preparative HPLC to provide example 27.

ESI-MS: 431 [M+H]$^+$; HPLC (Rt): 0.69 min (method B)

Example 28

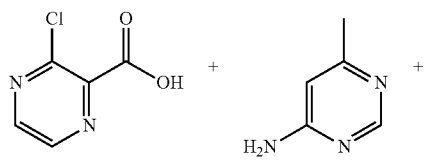

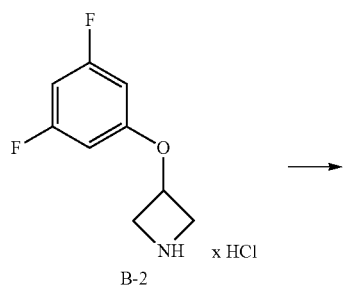

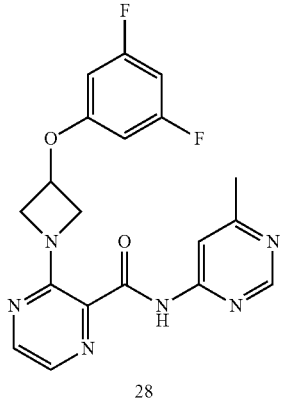

28

A mixture of 3-chloropyrazine-2-carboxylic acid (31.7 mg, 200.0 µmol), 1-methylimidazole (40.3 µL, 500.0 µmol) and chloro-N,N,N',N'-tetramethylformamidinium hexafluorophosphate (70.1 mg, 250.0 µmol) in NMP (1 mL) is stirred for 10 min at RT. 4-Amino-6-methylpyrimidine (22.9 mg, 210.0 µmol) is added and the mixture is stirred for 18 h at RT. Intermediate B-2 (42.1 mg, 190.0 µmol) and DIPEA (100.0 µL, 581.0 µmol) are added to the reaction mixture. After stirring for 3.5 h at 100° C. the mixture is cooled to RT. Stirring is continued at RT for 20 h, and the mixture purified directly by preparative HPLC to provide example 28.

ESI-MS: 399 [M+H]$^+$; HPLC (Rt): 0.70 min (method B)

Example 29

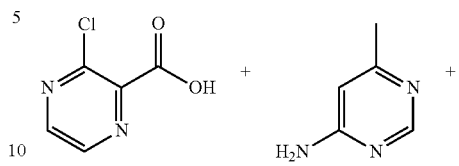

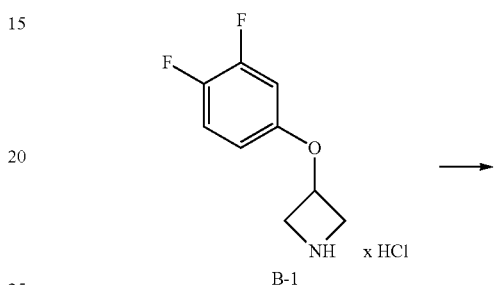

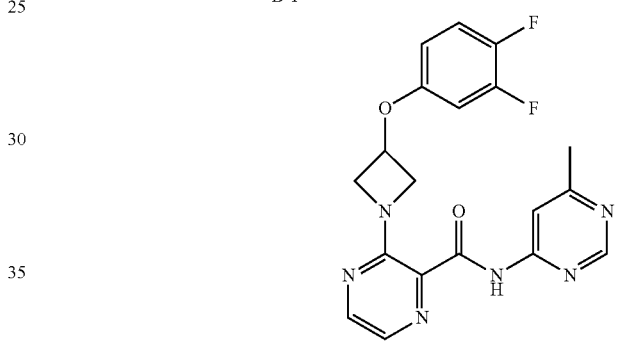

29

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-methylpyrimidine (36.1 mg, 331.0 µmol) is added and the mixture is stirred for 75 min at RT. Intermediate B-1 (73.4 mg, 331.0 µmol) and DIPEA (300.0 µL, 1744.0 µmol) are added to the reaction mixture. After stirring for 1 h at 100° C. the mixture is cooled to RT and poured into water. The precipitate is collected by filtration, washed with water and dried at 40° C. for 2 d to provide example 29.

ESI-MS: 399 [M+H]$^+$; HPLC (Rt): 0.68 min (method B)

Example 30

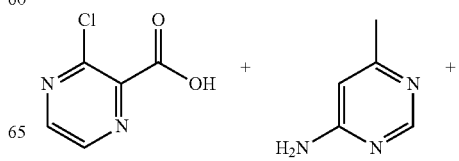

-continued

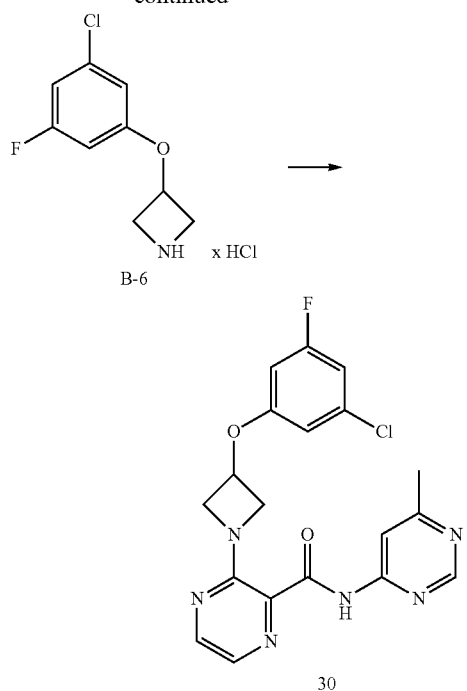

A mixture of 3-chloropyrazine-2-carboxylic acid (31.7 mg, 200.0 µmol), 1-methylimidazole (40.3 µL, 500.0 µmol) and chloro-N,N,N',N'-tetramethylformamidinium hexafluorophosphate (70.1 mg, 250.0 µmol) in NMP (1 mL) is stirred for 10 min at RT. 4-Amino-6-methylpyrimidine (22.9 mg, 210.0 µmol) is added and the mixture is stirred for 18 h at RT. Intermediate B-6 (45.2 mg, 190.0 µmol) and DIPEA (100.0 µL, 581.0 µmol) are added to the reaction mixture. After stirring for 3.5 h at 100° C. the mixture is cooled to RT. Stirring is continued at RT for 20 h, and the mixture purified directly by preparative HPLC to provide example 30.

ESI-MS: 415/417 [M+H]⁺; HPLC (Rt): 0.75 min (method B)

Example 31

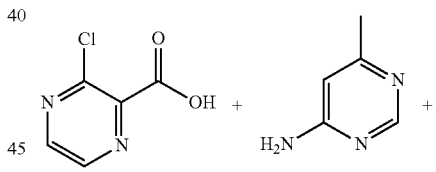

-continued

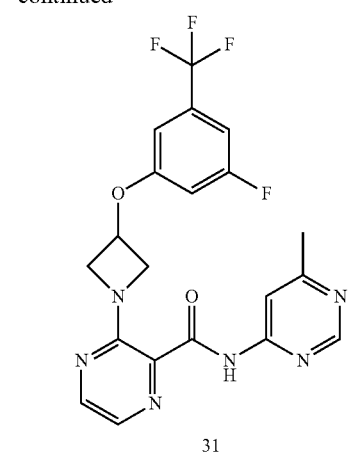

A mixture of 3-chloropyrazine-2-carboxylic acid (31.7 mg, 200.0 µmol), 1-methylimidazole (40.3 µL, 500.0 µmol) and chloro-N,N,N',N'-tetramethylformamidinium hexafluorophosphate (70.1 mg, 250.0 µmol) in NMP (1 mL) is stirred for 10 min at RT. 4-Amino-6-methylpyrimidine (22.9 mg, 210.0 µmol) is added and the mixture is stirred for 18 h at RT. Intermediate B-7 (51.6 mg, 190.0 µmol) and DIPEA (100.0 µL, 581.0 µmol) are added to the reaction mixture. After stirring for 4 h at 100° C. the mixture is cooled to RT and purified directly by preparative HPLC to provide example 31.

ESI-MS: 449 [M+H]⁺; HPLC (Rt): 0.77 min (method B)

Example 32

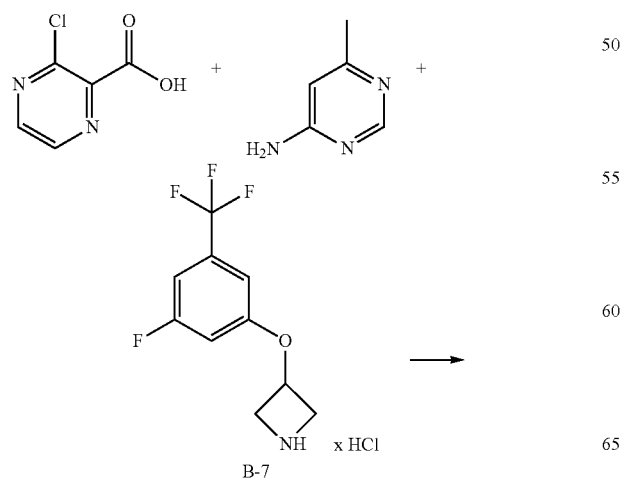

-continued

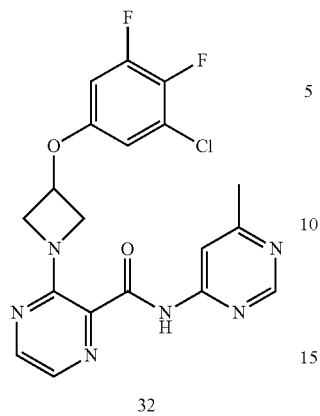

32

A mixture of 3-chloropyrazine-2-carboxylic acid (31.7 mg, 200.0 μmol), 1-methylimidazole (40.3 μL, 500.0 μmol) and chloro-N,N,N',N'-tetramethylformamidinium hexafluorophosphate (70.1 mg, 250.0 mol) in NMP (1 mL) is stirred for 10 min at RT. 4-Amino-6-methylpyrimidine (22.9 mg, 210.0 μmol) is added and the mixture is stirred for 18 h at RT. Intermediate B-4 (48.7 mg, 190.0 μmol) and DIPEA (100.0 μL, 581.0 μmol) are added to the reaction mixture. After stirring for 3.5 h at 100° C. the mixture is cooled to RT. Stirring is continued at RT for 20 h, and the mixture purified directly by preparative HPLC to provide example 32.

ESI-MS: 433/435 [M+H]$^+$; HPLC (Rt): 0.75 min (method B)

-continued

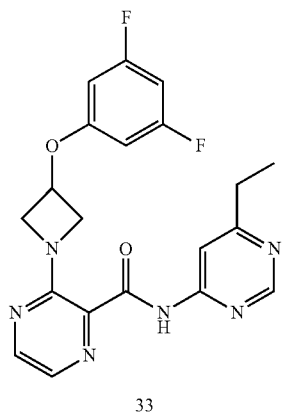

33

A mixture of 3-chloropyrazine-2-carboxylic acid (50.0 mg, 315.0 μmol), 1-methylimidazole (63.5 μL, 788.0 μmol), and chloro-N,N,N',N'-tetramethylformamidinium hexafluorophosphate (110.6 mg, 394.0 μmol) in NMP (0.7 mL) is stirred for 5 min at RT. 4-Amino-6-ethylpyrimidine (40.8 mg, 331.0 μmol) is added and the mixture is stirred for 4 h at RT. Intermediate B-2 (73.4 mg, 331.0 μmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 33.

ESI-MS: 413 [M+H]$^+$; HPLC (Rt): 0.75 min (method B)

Example 33

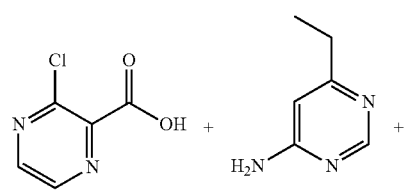

Example 34

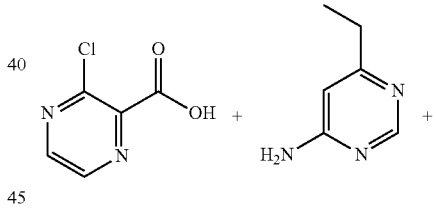

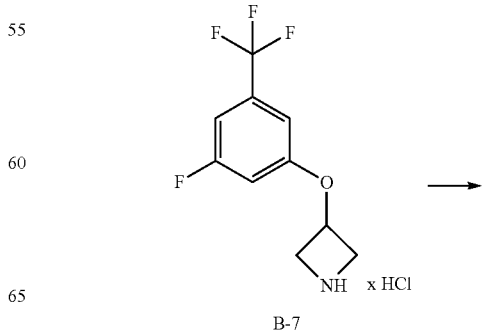

-continued

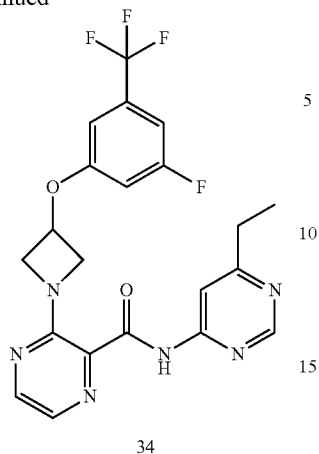

34

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-7 (90.0 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 34.

ESI-MS: 463 [M+H]$^+$; HPLC (Rt): 0.82 min (method B)

-continued

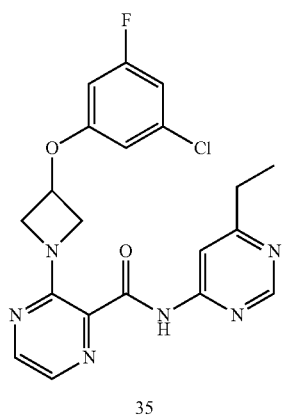

35

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-6 (78.8 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 35.

ESI-MS: 429/431 [M+H]$^+$; HPLC (Rt): 0.81 min (method B)

Example 35

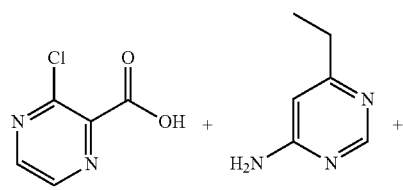

Example 36

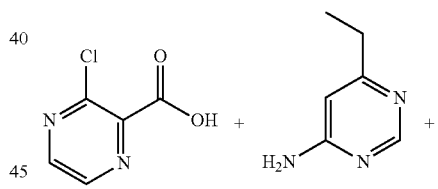

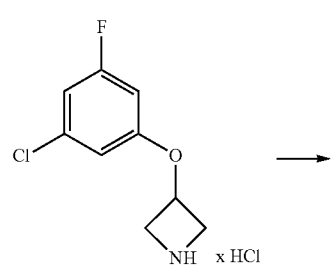

B-5

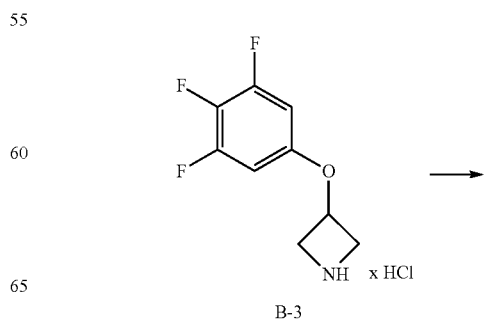

B-3

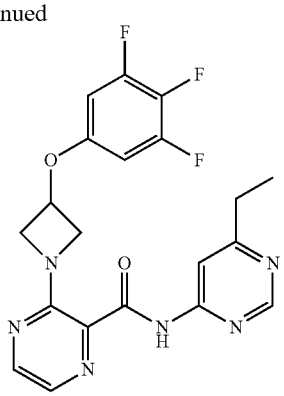

36

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-3 (79.4 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 36.

ESI-MS: 431 [M+H]⁺; HPLC (Rt): 0.77 min (method B)

Example 37

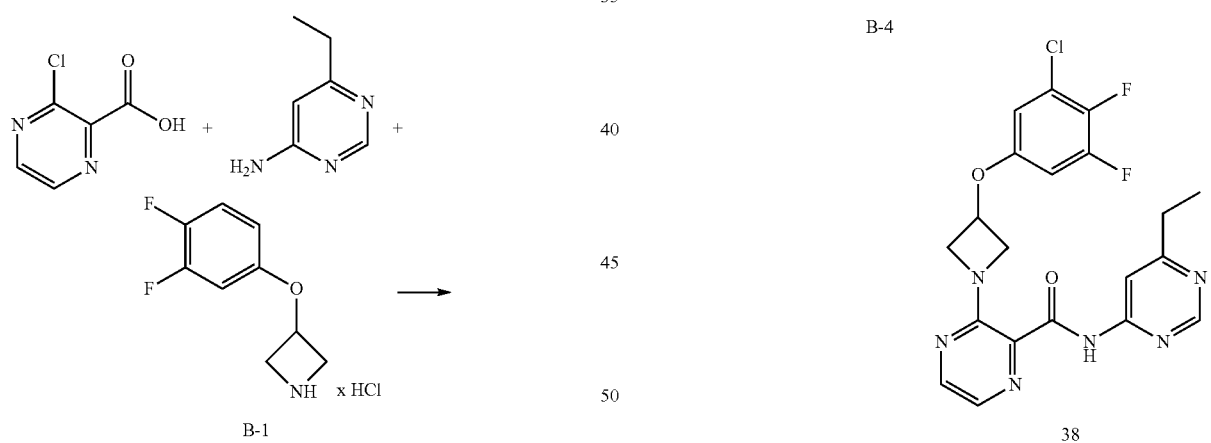

B-1

37

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-2 (73.4 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 37.

ESI-MS: 413 [M+H]⁺; HPLC (Rt): 0.74 min (method B)

Example 38

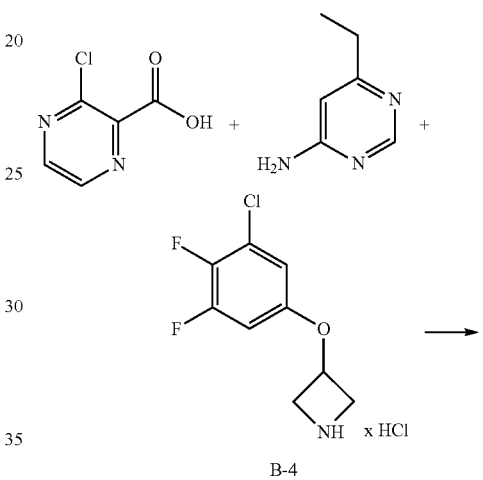

B-4

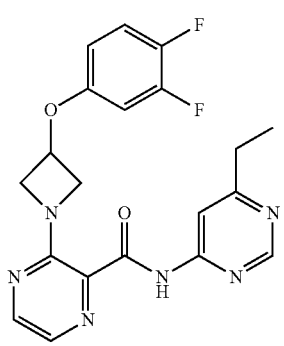

38

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-4 (84.8 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 38.

ESI-MS: 447/449 [M+H]⁺; HPLC (Rt): 0.81 min (method B)

Example 39

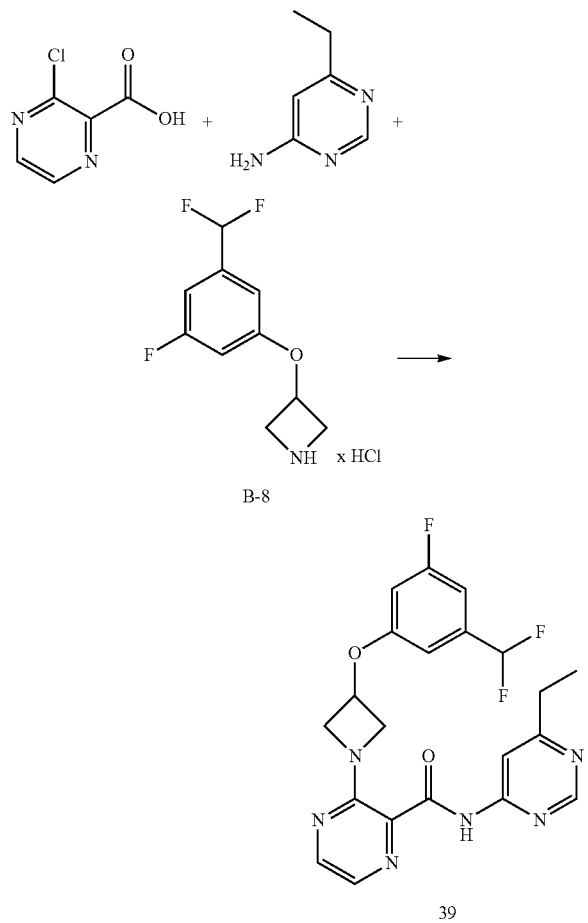

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-8 (84.0 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 39.

ESI-MS: 445 [M+H]$^+$; HPLC (Rt): 0.75 min (method B)

Example 40

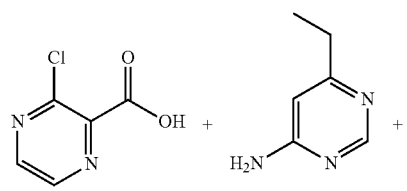

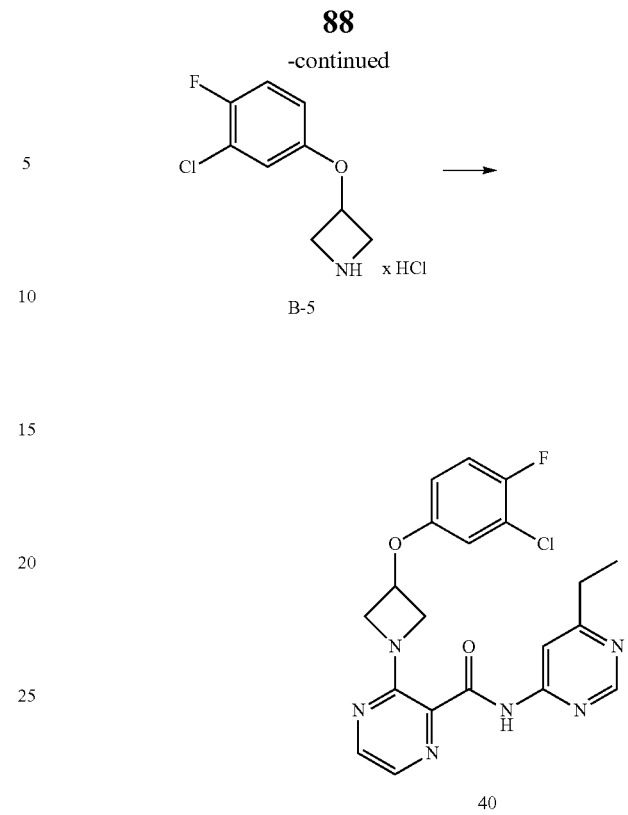

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 4-Amino-6-ethylpyrimidine (40.8 mg, 331.0 µmol) is added and the mixture is stirred for 4 h at RT. Intermediate B-5 (78.8 mg, 331.0 µmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 40.

ESI-MS: 429/431 [M+H]$^+$; HPLC (Rt): 0.78 min (method B)

Example 41

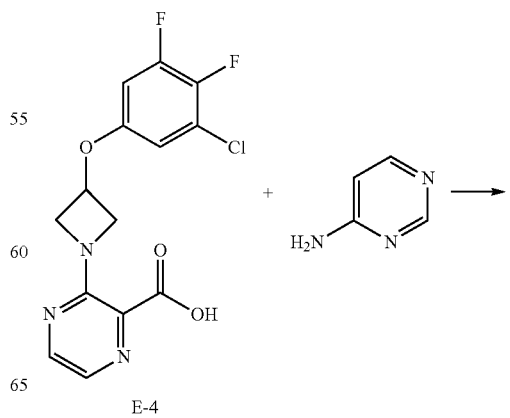

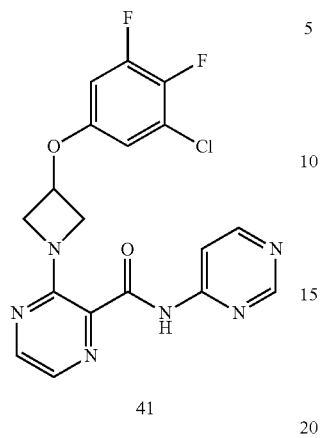

41

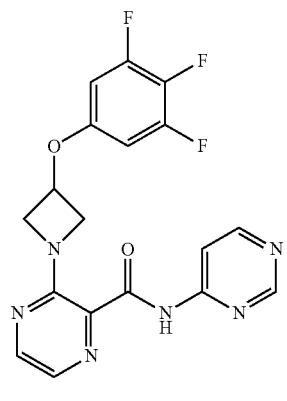

42

A mixture of intermediate E-4 (50.0 mg, 146.0 µmol), 1-methylimidazole (46.5 µL, 585.0 µmol), chloro-N,N,N',N'-tetramethylformamidinium hexafluorophosphate (49.3 mg, 176.0 µmol) and 4-aminopyrimidine (15.3 mg, 161.0 µmol) in DMA (2 mL) is stirred for 3 h at RT. After the addition of water the formed precipitate is collected by filtration. The precipitate is taken up in DCM and passed through a phase separation cartridge to remove remaining water. The organic phase is concentrated under reduced pressure, dissolved in acetonitrile and lyophylisized to give crude product. The crude product is slurried in a mixture of acetonitrile/methanol (1/1 v/v) and DMF, then filtered. The organic phase is purified via preparative HPLC to provide example 41.

ESI-MS: 419/421 [M+H]$^+$; HPLC (Rt): 0.73 min (method B)

Example 42

A mixture of intermediate E-2 (50.0 mg, 154.0 µmol), 1-methylimidazole (48.8 µL, 615.0 µmol), chloro-N,N,N',N'-tetramethylformamidinium hexafluorophosphate (51.8 mg, 184.0 µmol) and 4-aminopyrimidine (16.1 mg, 169.0 µmol) in DMA (2 mL) is stirred for 3 h at RT. After the addition of water the formed precipitate is collected by filtration. The precipitate is taken up in DCM and passed through a phase separation cartridge to remove remaining water. The organic phase is concentrated under reduced pressure, dissolved in acetonitrile and lyophylisized to give crude product. The crude product is purified via MPLC (silica gel, gradient DCM/methanol 100→95/5 v/v). Fractions containing product are collected and concentrated under reduced pressure. Repurification via preparative HPLC provides example 42.

ESI-MS: 403 [M+H]$^+$; HPLC (Rt): 0.89 min (method D)

Example 43

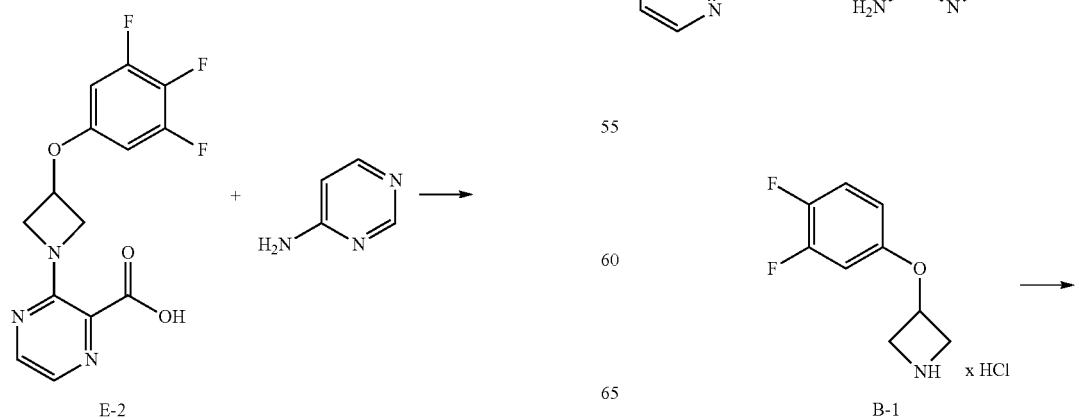

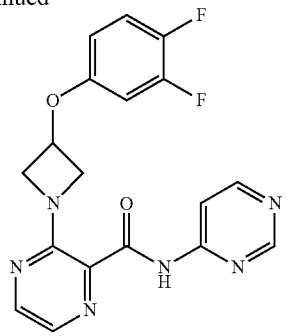

43

A mixture of 3-chloropyrazine-2-carboxylic acid (50.0 mg, 315.0 μmol), 1-methylimidazole (63.5 μL, 788.0 μmol) and chloro-N,N,N',N'-tetramethylformamidinium hexafluorophosphate (110.6 mg, 394.0 μmol) in NMP (0.7 mL) is stirred for 5 min at RT. 4-Aminopyrimidine (31.5 mg, 331.0 μmol) is added and the mixture is stirred for 4 h at RT. Intermediate 8-1 (73.4 mg, 331.0 μmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 43.

ESI-MS: 385 [M+H]$^+$; HPLC (Rt): 0.65 min (method B)

Example 44

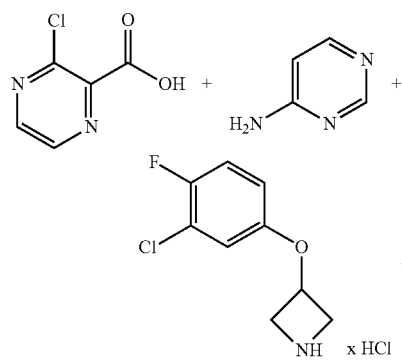

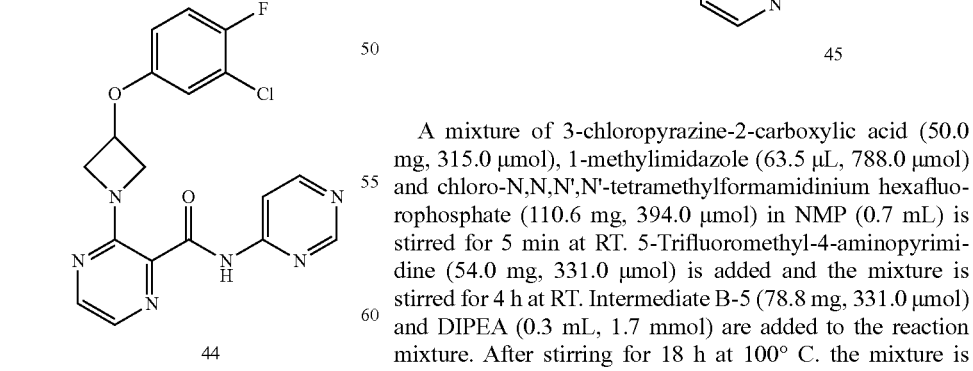

44

A mixture of 3-chloropyrazine-2-carboxylic acid (50.0 mg, 315.0 μmol), 1-methylimidazole (63.5 μL, 788.0 μmol) and chloro-N,N,N',N'-tetramethylformamidinium hexafluorophosphate (110.6 mg, 394.0 μmol) in NMP (0.7 mL) is stirred for 5 min at RT. 4-Aminopyrimidine (31.5 mg, 331.0 μmol) is added and the mixture is stirred for 4 h at RT. Intermediate B-5 (78.8 mg, 331.0 μmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 44.

ESI-MS: 401/403 [M+H]$^+$; HPLC (Rt): 0.69 min (method B)

Example 45

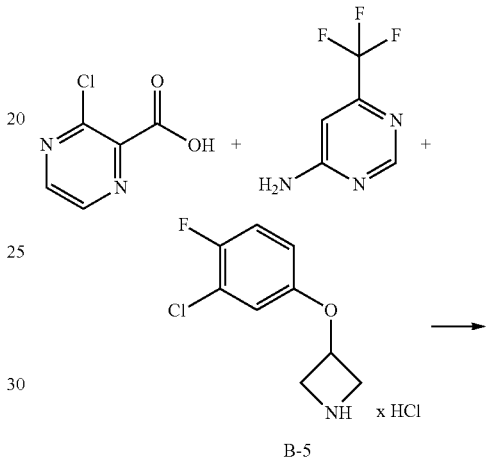

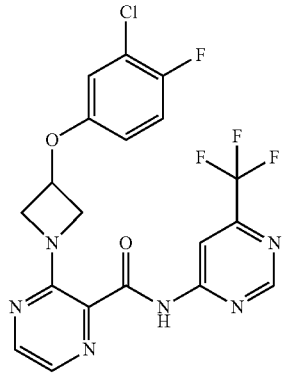 [SMILES: O=C(Nc1cc(C(F)(F)F)ncn1)c1nccnc1N1CC(Oc2ccc(F)c(Cl)c2)C1]

45

A mixture of 3-chloropyrazine-2-carboxylic acid (50.0 mg, 315.0 μmol), 1-methylimidazole (63.5 μL, 788.0 μmol) and chloro-N,N,N',N'-tetramethylformamidinium hexafluorophosphate (110.6 mg, 394.0 μmol) in NMP (0.7 mL) is stirred for 5 min at RT. 5-Trifluoromethyl-4-aminopyrimidine (54.0 mg, 331.0 μmol) is added and the mixture is stirred for 4 h at RT. Intermediate B-5 (78.8 mg, 331.0 μmol) and DIPEA (0.3 mL, 1.7 mmol) are added to the reaction mixture. After stirring for 18 h at 100° C. the mixture is cooled to RT. The reaction mixture is diluted with acetonitrile and is purified directly by preparative HPLC to provide example 45.

ESI-MS: 469/471 [M+H]$^+$; HPLC (Rt): 0.84 min (method B)

Example 46

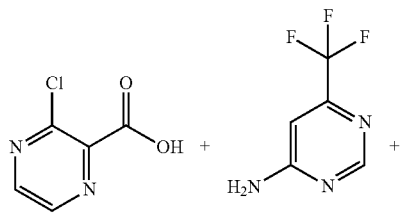

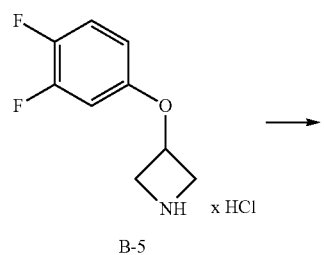

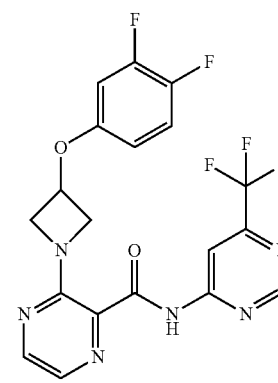

A mixture of 3-chloropyrazine-2-carboxylic acid (50.0 mg, 315.0 µmol), 1-methylimidazole (63.5 µL, 788.0 µmol) and chloro-N,N,N',N'-tetramethylformamidinium hexafluorophosphate (110.6 mg, 394.0 µmol) in NMP (0.7 mL) is stirred for 5 min at RT. 5-Trifluoromethyl-4-aminopyrimidine (54.0 mg, 331.0 µmol) is added and the mixture is stirred for 4 h at RT. Intermediate B-1 (73.4 mg, 331.0 µmol) and DIPEA (0.3 ml, 1.7 mmd) are added to the reaction mixture. After stirring for 18 h at 100° C. the mixture is cooled to RT. The reaction mixture is diluted with acetonitrile and is purified twice by preparative HPLC to provide example 46.

ESI-MS: 453 [M+H]$^+$; HPLC (Rt): 0.79 min (method B)

The invention claimed is:
1. A compound of formula (I)

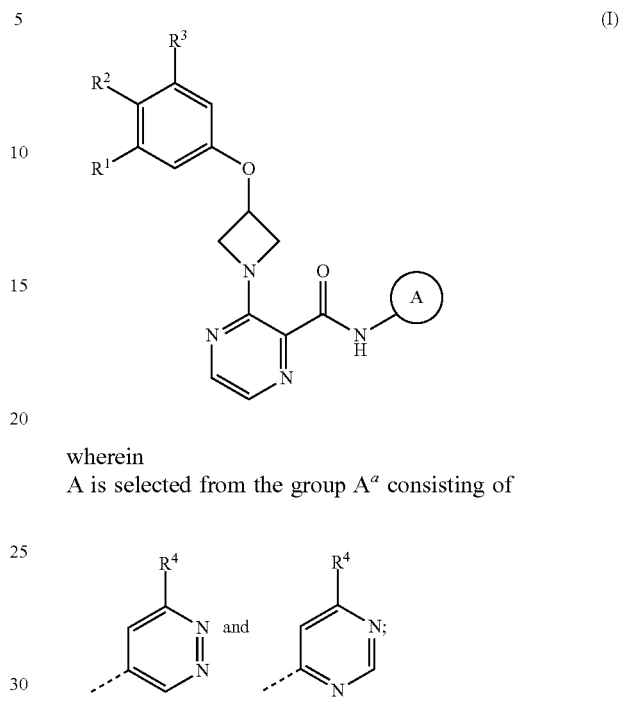

wherein
A is selected from the group A$^a$ consisting of

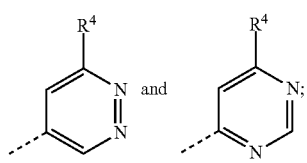

R is selected from the group R$^{1a}$ consisting of H— and F—;
R$^2$ is selected from the group R$^{2a}$ consisting of H— and F—;
R$^3$ is selected from the group R$^{3a}$ consisting of halogen, F$_2$HCO—, F$_3$CO—, F$_2$HC— and F$_3$C—;
R$^4$ is selected from the group R$^{4a}$ consisting of
H— and C$_{1-3}$-alkyl-,
wherein the above mentioned C$_{1-3}$-alkyl-group may optionally be substituted with 1 to 5 substituents independently selected from the group consisting of fluorine;
or a salt thereof.

2. A compound, or a salt thereof, according to claim 1, wherein
A is selected from

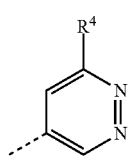

or a salt thereof.

3. The compound, or a salt thereof, of claim 1, wherein R$^3$ is selected from the group R$^{3b}$ consisting of
F—, Cl—, and F$_2$HC—
or a salt thereof.

4. The compound, or a salt thereof, of claim 1, wherein R$^3$ is selected from
F—,
or a salt thereof.

5. The compound, or a salt thereof, of claim 1, wherein $R^4$ is selected from the group $R^{4b}$ consisting of H—, $C_{1\text{-}2}$-alkyl- and $F_3C$—, or a salt thereof.

6. The compound, or a salt thereof, of claim 1, wherein $R^4$ is selected from $C_{1\text{-}2}$-alkyl-, or a salt thereof.

7. A compound selected from the group consisting of

| No. | Structure |
|---|---|
| I | (3-fluoro-5-(trifluoromethyl)phenoxy-azetidinyl pyrazine carboxamide pyridazine) |
| II | (3-chloro-5-fluorophenoxy-azetidinyl pyrazine carboxamide pyridazine) |
| III | (3,5-difluorophenoxy-azetidinyl pyrazine carboxamide pyridazine) |
| IV | (3,4,5-trifluorophenoxy-azetidinyl pyrazine carboxamide pyridazine) |
| V | (3,4-difluorophenoxy-azetidinyl pyrazine carboxamide pyridazine) |
| VI | (3-(difluoromethyl)-5-fluorophenoxy-azetidinyl pyrazine carboxamide pyridazine) |
| VII | (3-chloro-4-fluorophenoxy-azetidinyl pyrazine carboxamide pyridazine) |

| No. | Structure |
|---|---|
| VIII | (structure) |
| IX | (structure) |
| X | (structure) |
| XI | (structure) |
| XII | (structure) |
| XIII | (structure) |
| XIV | (structure) |
| XV | (structure) |

| No. | Structure |
|---|---|
| XVI | (structure) |
| XVII | (structure) |
| XVIII | (structure) |
| XIX | (structure) |
| XX | (structure) |
| XXI | (structure) |
| XXII | (structure) |
| XXIII | (structure) |

-continued

| No. | Structure |
|---|---|
| XXIV | 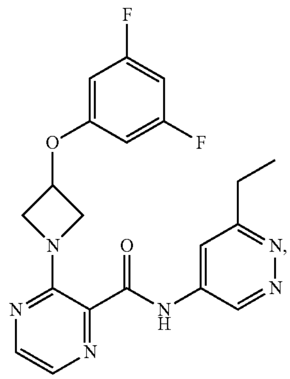 [SMILES: CCc1cc(NC(=O)c2nccnc2N2CC(Oc3cc(F)cc(F)c3)C2)cnn1] |
| XXV | 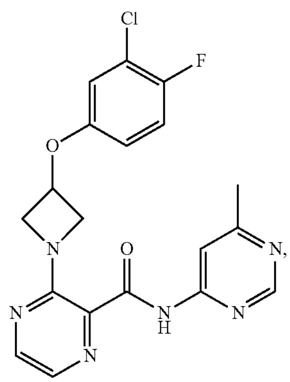 [SMILES: Cc1cc(NC(=O)c2nccnc2N2CC(Oc3ccc(F)c(Cl)c3)C2)ncn1] |
| XXVI | 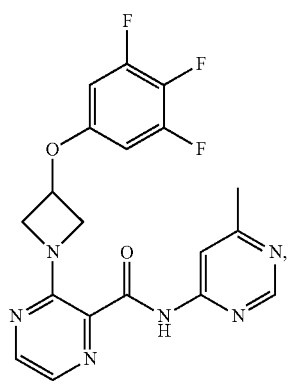 [SMILES: Cc1cc(NC(=O)c2nccnc2N2CC(Oc3cc(F)c(F)c(F)c3)C2)ncn1] |
| XXVII | 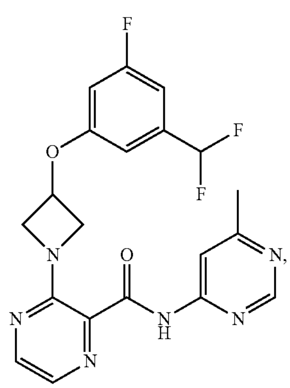 [SMILES: Cc1cc(NC(=O)c2nccnc2N2CC(Oc3cc(F)cc(C(F)F)c3)C2)ncn1] |

-continued

| No. | Structure |
|---|---|
| XXVIII | 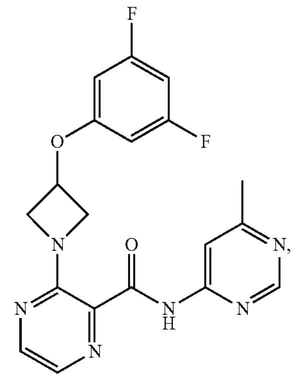 [SMILES: Cc1cc(NC(=O)c2nccnc2N2CC(Oc3cc(F)cc(F)c3)C2)ncn1] |
| XXIX | 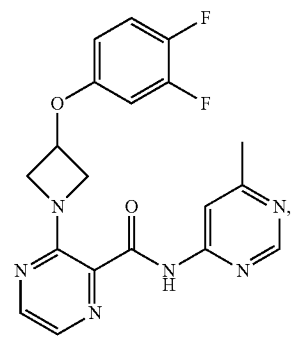 [SMILES: Cc1cc(NC(=O)c2nccnc2N2CC(Oc3ccc(F)c(F)c3)C2)ncn1] |
| XXX | 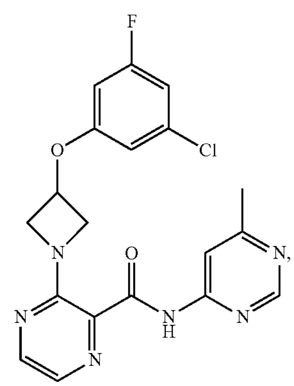 [SMILES: Cc1cc(NC(=O)c2nccnc2N2CC(Oc3cc(F)cc(Cl)c3)C2)ncn1] |
| XXXI | 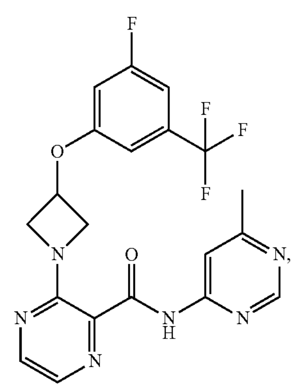 [SMILES: Cc1cc(NC(=O)c2nccnc2N2CC(Oc3cc(F)cc(C(F)(F)F)c3)C2)ncn1] |

| No. | Structure |
|---|---|
| XXXII | 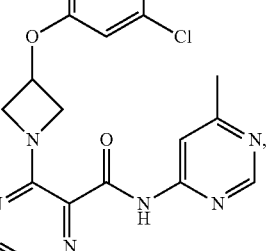 |
| XXXIII | |
| XXXIV | |
| XXXV | |
| No. | Structure |
|---|---|
| XXXVI | 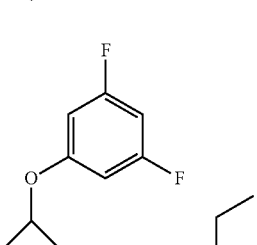 |
| XXXVII | |
| XXXVIII | |
| XXXIX | |

| No. | Structure |
|---|---|
| XL | (structure: 3-chloro-4-fluorophenoxy-azetidine linked to pyrazine-2-carboxamide N-(6-ethylpyrimidin-4-yl)) |
| XLI | (structure: 3-chloro-4,5-difluorophenoxy-azetidine linked to pyrazine-2-carboxamide N-(pyrimidin-4-yl)) |
| XLII | (structure: 3,4,5-trifluorophenoxy-azetidine linked to pyrazine-2-carboxamide N-(pyrimidin-4-yl)) |
| XLIII | (structure: 3,4-difluorophenoxy-azetidine linked to pyrazine-2-carboxamide N-(pyrimidin-4-yl)) |
| XLIV | (structure: 3-chloro-4-fluorophenoxy-azetidine linked to pyrazine-2-carboxamide N-(pyrimidin-4-yl)) |
| XLV | (structure: 3-chloro-4-fluorophenoxy-azetidine linked to pyrazine-2-carboxamide N-(6-trifluoromethylpyrimidin-4-yl)), and |
| XLVI | (structure: 3,4-difluorophenoxy-azetidine linked to pyrazine-2-carboxamide N-(6-trifluoromethylpyrimidin-4-yl)) | or a pharmaceutically acceptable salt thereof.

8. A pharmaceutically acceptable salt of a compound according to claim 7.

9. A pharmaceutical composition containing at least one compound according to claim 1, or a pharmaceutically acceptable salt thereof together with one or more pharmaceutically acceptable carrier(s).

10. A pharmaceutical composition containing at least one compound according to claim 7, or a pharmaceutically acceptable salt thereof, together with one or more pharmaceutically acceptable carrier(s).

11. A pharmaceutical composition containing at least one pharmaceutically acceptable salt according to claim 8 together with one or more pharmaceutically acceptable carrier(s).

* * * * *